United States Patent
Kohn et al.

(10) Patent No.: US 7,838,672 B2
(45) Date of Patent: Nov. 23, 2010

(54) USE OF FUSED RING-1,2,4-BENZOTRIAZINE DERIVATIVES AS HERBICIDES OR PLANT GROWTH REGULATORS FOR THE CONTROL OF UNDESIRED PLANTS OR VEGETATION, COMPOUNDS AND COMPOSITIONS THEREOF, AND PROCESSES FOR THEIR PREPARATION

(75) Inventors: Arnim Kohn, Wiesbaden (DE); Wolfgang Giencke, Hofheim (DE); Hendrick Helmke, Liederbach (DE); Kenneth Garcia Marques, El Masnou (ES); Thomas Auler, Leichlingen (DE); Martin Hills, Idstein (DE); Gyorgy Hajos, Budapest (HU); Zsuzsanna Riedl, Budapest (HU); Dieter Feucht, Eschborn (DE)

(73) Assignee: Bayer CropScience GmbH (DE)

( * ) Notice: Subject to any disclaimer, the term of this patent is extended or adjusted under 35 U.S.C. 154(b) by 798 days.

(21) Appl. No.: 10/566,311

(22) PCT Filed: Jul. 17, 2004

(86) PCT No.: PCT/EP2004/008010
§ 371 (c)(1), (2), (4) Date: Jan. 27, 2006

(87) PCT Pub. No.: WO2005/014595
PCT Pub. Date: Feb. 17, 2005

(65) Prior Publication Data
US 2007/0042909 A1   Feb. 22, 2007

(30) Foreign Application Priority Data
Jul. 31, 2003   (EP) .................. 03017317

(51) Int. Cl.
C07D 487/04   (2006.01)
A01N 43/90   (2006.01)
A61K 31/53   (2006.01)
(52) U.S. Cl. .................. 544/183; 544/184; 504/228; 514/243
(58) Field of Classification Search .............. 544/183, 544/184; 514/243; 504/228
See application file for complete search history.

(56) References Cited

U.S. PATENT DOCUMENTS
4,316,022 A * 2/1982 Hajos et al. ............... 544/184

FOREIGN PATENT DOCUMENTS
DE 83869 9/1970
DE 3340026 5/1985
EP 0024931 3/1981

OTHER PUBLICATIONS

Messmer et al., Acta Chimica Academiae Scientiarum Hungaricae, Tomus 105(3), Jan. 7, 1980, pp. 189-199, Budapest, Hungary.
Messmer et al., Magyar Kemiai Folyoirat, 1980, pp. 471-476, vol. 86 Issue 10, Budapest, Hungary.
Messmer et al., Journal of Organic Chemistry, vol. 44, No. 11, 1979, pp. 1823-1825.
Sasaki et al., Chemische Berichte, 102 (11), 1969, pp. 3818-3823.
Bartra et al., Tetrahedron Letters, Vo. 28, No. 47, 197, pp. 5941-5944, Great Britain.
Gorjan et al., Monatshefte für Chemie 107 (5), 1976, pp. 1199-1208, Ljubljana, Slovenia(formerly Yugoslavia).
Assad et al, Zeitschrift fur Naturforschung 51A(9): Physical Sciences, 1996, pp. 1012-1018, Tubingen, Germany.
Fos et al., Journal of Organic Chemistry, vol. 50, No. 24, 1985, pp. 4891-4899.
Messmer et al., Magyar Kemiai Folyoirat,1974, pp. 527-530, vol. 80 Issue 12, Budapest, Hungary.
Messmer et al., J. Het. Chem., Aug. 1973, vol. 10, No. 4, pp. 575-578.
Castillon et al, Journal of Organic Chemistry, vol. 47, No. 20, 1982, pp. 3886-3890.

* cited by examiner

*Primary Examiner*—Venkataraman Balasubramanian
(74) *Attorney, Agent, or Firm*—Frommer Lawrence & Haug LLP

(57) ABSTRACT

The use of fused ring-1,2,4-benzotriazine derivatives as herbicides or plant growth regulators for the control of undesired plants or vegetation, compounds and compositions thereof, and processes for their preparation.

The invention relates to the use of a compound of the formula (I) or a salt thereof:

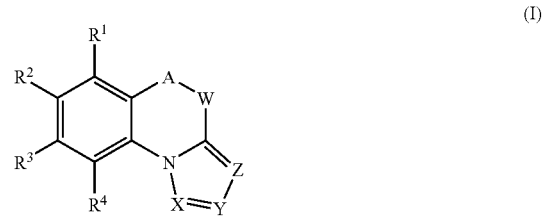

wherein A-W, X, Y, Z, $R^1$, $R^2$, $R^3$ and $R^4$ are defined in the description, as herbicides or plant growth regulators for the control of undesired plants or vegetation, to compounds and compositions thereof, and to processes for their preparation.

17 Claims, No Drawings

USE OF FUSED RING-1,2,4-BENZOTRIAZINE DERIVATIVES AS HERBICIDES OR PLANT GROWTH REGULATORS FOR THE CONTROL OF UNDESIRED PLANTS OR VEGETATION, COMPOUNDS AND COMPOSITIONS THEREOF, AND PROCESSES FOR THEIR PREPARATION

The use of fused ring-1,2,4-benzotriazine derivatives as herbicides or plant growth regulators for the control of undesired plants or vegetation, compounds and compositions thereof, and processes for their preparation.

The invention relates to the use of fused ring-1,2,4-benzotriazine derivatives as herbicides or plant growth regulators for the control of undesired plants or vegetation, to compounds and compositions thereof, and to processes for their preparation.

BACKGROUND OF THE INVENTION

Canadian patent publication number CA 1211444 describes a process for the preparation of imidazo[2,1-c][1,2,4]benzotriazine-2-carboxylic acid derivatives as allergy inhibitors.

US patent publication number U.S. Pat. No. 4,316,022 and Japanese patent publication number JP 56008386 describe benzo-as-triazine derivatives as analgesics.

DETAILED DESCRIPTION OF THE INVENTION

The present invention relates to the use of a compound of the formula (I) or a salt thereof:

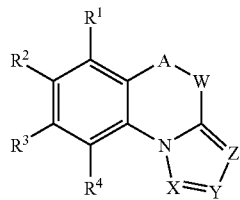

(I)

wherein
A-W is N═N, N$^+$(O$^-$)═N or N$^5$—NR$^6$, wherein A represents the atom or substituted atom shown on the left side of the groups representing A-W;
X is N or CR$^7$;
Y is N or CR$^8$;
Z is N or CR$^9$;
R$^1$, R$^2$, R$^3$ and R$^4$ are each independently H, OH, halogen, nitro, cyano, formyl, amino, carbamoyl, CO$_2$H or sulfamoyl, or benzyl or also phenoxy,
where each of the latter two radicals is unsubstituted or substituted by one or more radicals selected from the group consisting of $(C_1-C_6)$alkyl, $(C_1-C_6)$haloalkyl, halogen, OH, $(C_1-C_6)$alkoxy, also $(C_1-C_6)$haloalkoxy, $(C_1-C_6)$alkyl-S(O)$_n$—, nitro, cyano, amino, $(C_1-C_6)$alkylamino, $(C_1-C_6)$dialkylamino, $(C_1-C_6)$alkoxycarbonyl and CO$_2$H,
or are $(C_1-C_6)$alkyl, $(C_2-C_6)$alkenyl, $(C_2-C_6)$alkynyl, $(C_3-C_6)$cycloalkyl, $(C_3-C_6)$cycloalkyl-$(C_1-C_6)$alkyl-, $(C_1-C_6)$alkoxy, $(C_2-C_6)$alkenyloxy, $(C_2-C_6)$alkynyloxy, $(C_1-C_6)$alkyl-C(═O)O—, $(C_1-C_6)$alkyl-S(O)$_n$—, $(C_1-C_6)$alkylamino, $(C_1-C_6)$dialkylamino, $(C_1-C_6)$alkoxycarbonyl, $(C_1-C_6)$alkylcarbonyl, $(C_1-C_6)$alkylcarbamoyl, $(C_1-C_6)$dialkylcarbamoyl, $(C_1-C_6)$alkylsulfamoyl or $(C_1-C_6)$dialkylsulfamoyl,
where each of the 18 last-mentioned radicals is unsubstituted or substituted by one or more radicals selected from the group consisting of halogen, OH, $(C_1-C_6)$alkoxy, $(C_1-C_6)$alkyl-S(O)$_n$— and in the case of cyclic radicals also $(C_1-C_6)$alkyl and $(C_1-C_6)$haloalkyl;
R$^5$ and R$^6$ are each independently H, $(C_1-C_6)$alkyl, $(C_1-C_6)$haloalkyl, $(C_2-C_6)$alkenyl, $(C_2-C_6)$alkynyl, formyl, $(C_1-C_6)$alkylcarbonyl, $(C_2-C_6)$alkenylcarbonyl, COR$^{10}$, $(C_1-C_6)$alkoxycarbonyl, $(C_1-C_6)$alkyl-SO$_2$—, $(C_1-C_6)$alkoxy-$(C_1-C_6)$alkyl- or R$^{10}$;
R$^7$, R$^8$ and R$^9$ are each independently H, halogen, nitro, cyano, S(O)$_n$R$^{10}$, S(O)$_n$CH$_2$CO$_2$R$^{11}$, S(O)$_n$CH$_2$CO$_2$N[(C$_1$-C$_6$)alkyl]$_2$, S(O)$_n$CH$_2$CONR$^{12}$R$^{13}$, S(O)$_n$CH$_2$CONR$^{14}$NR$^{15}$ formyl, carbamoyl, OH, SH, R$^{10}$, NR$^{16}$R$^{17}$, 1,3-dioxolan-2-yl, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkyl-S(O)$_n$—, $(C_1-C_6)$alkoxycarbonyl, $(C_1-C_6)$alkylcarbonyl, $(C_1-C_6)$alkylcarbamoyl or $(C_1-C_6)$dialkylcarbamoyl, where each of the 10 last-mentioned radicals is unsubstituted or substituted by one or more radicals selected from the group consisting of halogen, OH, $(C_1-C_6)$alkoxy, $(C_1-C_6)$alkyl-S(O)$_n$— and in the case of cyclic radicals also $(C_1-C_6)$alkyl and $(C_1-C_6)$haloalkyl;
R$^{10}$ is (CH$_2$)$_m$phenyl unsubstituted or substituted by one or more radicals selected from the group consisting of halogen, $(C_1-C_6)$alkyl, $(C_1-C_6)$haloalkyl, $(C_1-C_6)$alkoxy, $(C_1-C_6)$haloalkoxy, nitro, cyano, $(C_1-C_6)$alkyl-S(O)$_n$—, $(C_1-C_6)$haloalkyl-S(O)$_n$—, amino, $(C_1-C_6)$alkylamino, $(C_1-C_6)$dialkylamino, $(C_1-C_6)$alkylcarbonyl, carbamoyl, $(C_1-C_6)$alkylcarbamoyl, $(C_1-C_6)$dialkylcarbamoyl, sulfamoyl, $(C_1-C_6)$alkylsulfamoyl and $(C_1-C_6)$dialkylsulfamoyl;
R$^{11}$ is H or $(C_1-C_6)$alkyl;
R$^{12}$ and R$^{13}$, or R$^{16}$ and R$^{17}$ are each independently H, $(C_1-C_6)$alkyl or R$^{10}$; or R$^{12}$ and R$^{13}$, or R$^{16}$ and R$^{17}$ together with the respective attached N atom form a five- or six-membered saturated ring which optionally contains an additional hetero atom in the ring which is selected from O, S and N, the ring being unsubstituted or substituted by one or more radicals selected from halogen, $(C_1-C_6)$alkyl and $(C_1-C_6)$haloalkyl;
R$^{14}$ and R$^{15}$ are each independently H or $(C_1-C_6)$alkyl;
n is 0, 1 or 2 in each of the occurrences; and
m is 0 or 1;

as a herbicide or plant growth regulator.

The invention also encompasses any stereoisomer, enantiomer, geometric isomer, tautomers and mixtures and salts thereof, if respective functional groups are present. In particular compounds of formula (I) wherein X, Y and Z are each N, of formula (Ia) can exist in certain cases as the open chain azide tautomer form of formula (Ib):

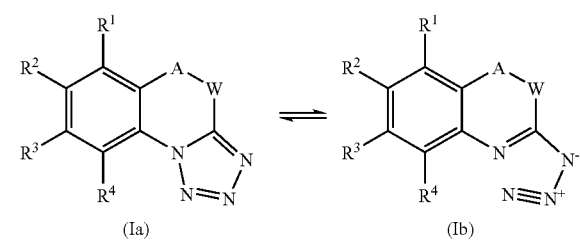

The tautomeric equilibrium between the azido form (Ib) and the ring closed compounds (1a) is described by Messmer, Hajos, Neszmelyi and Parkanyi in J. Org. Chem. (1984), 49(17), 3199-203; Messmer, Hajos, Tamas and Neszmelyi in J. Org. Chem. (1979), 44(11), 1823-5; Castillon, Melendez, Pascual and Vilarrasa in J. Org. Chem. (1982), 47(20), 3886-90; and by Asaad and El Ashry in Zeitschrift für Naturforschung A: Physical Sciences (1996), 51(9),1012-1018.

Typical tautomer forms which may also exist are shown below as formulae (Ic), (Id), (Ie) and (If):

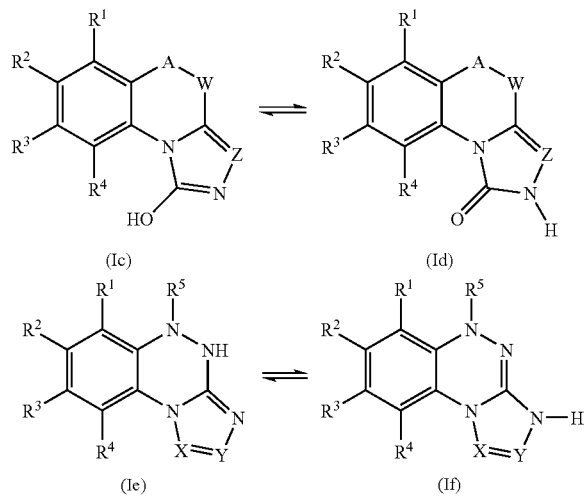

(Ic) (Id)

(Ie) (If)

In the present patent specification, including the accompanying claims, the aforementioned substituents have the following meanings:

Halogen means fluorine, chlorine, bromine or iodine.

The term "halo" before the name of a radical means that this radical is partially or completely halogenated, that is to say, substituted by F, Cl, Br, or I, in any combination.

The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$(C_1-C_6)$alkoxy-$(C_1-C_6)$alkyl-" means $(C_1-C_6)$alkyl which is substituted by $(C_1-C_6)$alkoxy.

"$(C_1-C_6)$Alkoxy" means an alkoxy group whose carbon chain has the meaning given under the expression "$(C_1-C_6)$ alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$ Alkenyl" accordingly denotes, for example, the vinyl, allyl, 2-methyl-2-propenyl, 2-butenyl, pentenyl, 2-methylpentenyl or the hexenyl group.

"$(C_2-C_6)$Alkynyl" means an unbranched or branched non-cyclic carbon chain having a number of carbon atoms which corresponds to this stated range and which contains one triple bond which can be located in any position of the respective unsaturated radical. "$(C_2-C_6)$Alkynyl" accordingly denotes, for example, the propargyl, 1-methyl-2-propynyl, 2-butynyl or 3-butynyl group.

"$(C_3-C_6)$Cycloalkyl" denotes monocyclic alkyl radicals, such as the cyclopropyl, cyclobutyl, cyclopentyl or cyclohexyl radical. $S(O)_n$ means S, SO or $SO_2$ depending upon the value of n.

The expression "one or more radicals selected from the group consisting of" in the definition is to be understood as meaning in each case one or more identical or different radicals selected from the stated group of radicals, unless specific limitations are defined expressly.

Compounds of the stated formula (I) according to the invention or their salts in which individual radicals have one of the preferred meanings which have already been stated or are stated hereinbelow and particularly those shown in the Tables which appear hereinbelow, or in particular those in which two or more of the preferred meanings which have already been stated or which are stated hereinbelow are combined, are of particular interest, mainly because of the more potent herbicidal action, better selectivity and/or greater ease of preparation.

Of particular interest for the use as herbicides or plant growth regulators in the invention are compounds of formula (I) where a radical selected from the group of radicals $R^1$, $R^2$, $R^3$, $R^4$, A, W, X, Y and Z is preferably defined as set forth below, wherein the definition of the radical is independent from the definitions of the other radicals of said group. Preferred compounds of formula (I) contain a combination of radicals of said group which comprise two or more preferred meanings set forth below.

In the following preferred definitions it is generally to be understood that where symbols are not specifically defined they are to be as previously defined in the description.

Preferably A-W is N=N, $N^+(O^-)$=N or NH—NH.

Preferably $R^1$, $R^2$, $R^3$ and $R^4$ are each independently H, OH, halogen, nitro, cyano, formyl, amino, carbamoyl, $CO_2H$ or sulfamoyl, or benzyl or also phenoxy,
  where each of the latter two radicals is unsubstituted or substituted by one or more radicals selected from the group consisting of $(C_1-C_4)$alkyl, $(C_1-C_4)$haloalkyl, halogen, OH, $(C_1-C_4)$alkoxy, also $(C_1-C_4)$haloalkoxy, $(C_1-C_4)$alkyl-$S(O)_n$—, nitro, cyano, amino, $(C_1-C_4)$ alkylamino, $(C_1-C_4)$dialkylamino, $(C_1-C_4)$alkoxycarbonyl and $CO_2H$,
or are $(C_1-C_4)$alkyl, $(C_2-C_4)$alkenyl, $(C_2-C_4)$alkynyl, $(C_3-C_6)$ cycloalkyl, $(C_3-C_6)$cycloalkyl-$(C_1-C_4)$alkyl-, $(C_1-C_4)$ alkoxy, $(C_2-C_4)$alkenyloxy, $(C_2-C_4)$alkynyloxy, $(C_1-C_4)$ alkyl-C(=O)O—, $(C_1-C_4)$alkyl-$S(O)_n$—, $(C_1-C_4)$ alkylamino, $(C_1-C_4)$dialkylamino, $(C_1-C_4)$ alkoxycarbonyl, $(C_1-C_4)$alkylcarbonyl, $(C_1-C_4)$ alkylcarbamoyl, $(C_1-C_4)$dialkylcarbamoyl, $(C_1-C_4)$ alkylsulfamoyl or $(C_1-C_4)$dialkylsulfamoyl,
  where each of the 18 last-mentioned radicals is unsubstituted or substituted by one or more radicals selected from the group consisting of halogen, OH, $(C_1-C_4)$ alkoxy, $(C_1-C_4)$alkyl-$S(O)_n$— and in the case of cyclic radicals also $(C_1-C_6)$alkyl and $(C_1-C_6)$haloalkyl.

More preferably $R^1$, $R^2$, $R^3$ and $R^4$ are each independently H, $(C_1-C_4)$alkyl, $(C_1-C_4)$haloalkyl, $(C_1-C_4)$alkoxy, OH, halogen, nitro, cyano, $(C_1-C_4)$alkyl-$S(O)_n$—, $(C_1-C_4)$haloalkyl-$S(O)_n$—, amino, $(C_1-C_4)$alkylamino, $(C_1-C_4)$dialkylamino, ($C_1$-$C_4$)alkoxycarbonyl, formyl, ($C_1$-$C_4$)alkylcarbonyl, carbamoyl, ($C_1$-$C_4$)alkylcarbamoyl or ($C_1$-$C_4$)dialkylcarbamoyl.

Preferably X is N or $CR^7$ wherein $R^7$ is H, halogen, nitro, cyano, $S(O)_nR^{10}$, $S(O)_nCH_2CO_2R^{11}$, $S(O)_nCH_2CONR^{12}R^{13}$, $S(O)_nCH_2CONR^{14}NR^{15}$, formyl, carbamoyl, OH, SH, $R^{10}$, $NR^{16}R^{17}$, 1,3-dioxolan-2-yl, ($C_1$-$C_4$)alkyl, ($C_3$-$C_6$)cycloalkyl, ($C_2$-$C_4$)alkenyl, ($C_2$-$C_4$)alkynyl, ($C_1$-$C_4$)alkoxy, ($C_1$-$C_4$)alkyl-$S(O)_n$—, ($C_1$-$C_4$)alkoxycarbonyl, ($C_1$-$C_4$)alkylcarbonyl, ($C_1$-$C_4$)alkylcarbamoyl, ($C_1$-$C_4$)dialkylcarbamoyl, where each of the 10 last-mentioned radicals is unsubstituted or substituted by one or more radicals selected from the group consisting of halogen, OH, ($C_1$-$C_4$)alkoxy and ($C_1$-$C_4$)alkyl-$S(O)_n$—; in which $R^{10}$ is $(CH_2)_m$phenyl unsubstituted or substituted by one or more radicals selected from the group consisting of halogen, ($C_1$-$C_4$)alkyl, ($C_1$-$C_4$)haloalkyl, ($C_1$-$C_4$)alkoxy, ($C_1$-$C_4$)haloalkoxy, nitro, cyano, ($C_1$-$C_4$)alkyl-$S(O)_n$—, ($C_1$-$C_4$)haloalkyl-$S(O)_n$—, amino, ($C_1$-$C_4$)alkylamino, ($C_1$-$C_4$)dialkylamino, ($C_1$-$C_4$)alkylcarbonyl, carbamoyl, ($C_1$-$C_4$)alkylcarbamoyl, ($C_1$-$C_4$)dialkylcarbamoyl, sulfamoyl, ($C_1$-$C_4$)alkylsulfamoyl and ($C_1$-$C_4$)dialkylsulfamoyl;

$R^{11}$ is H or ($C_1$-$C_4$)alkyl;

$R^{12}$ and $R^{13}$, or $R^{16}$ and $R^{17}$ are each independently H, (Cl-$C_4$)alkyl or $R^{10}$; or $R^{12}$ and $R^{13}$, or $R^{16}$ and $R^{17}$ together with the respective attached N atom form a five- or six-membered saturated ring which optionally contains an additional hetero atom in the ring which is selected from O,S and N, the ring being unsubstituted or substituted by one or more radicals selected from halogen, ($C_1$-$C_4$)alkyl and ($C_1$-$C_4$)haloalkyl; and $R^{14}$ and $R^{15}$ are each independently H or ($C_1$-$C_4$)alkyl.

More preferably X is N or $CR^7$ wherein $R^7$ is H, ($C_1$-$C_4$)alkyl, ($C_1$-$C_4$)haloalkyl, ($C_1$-$C_4$)alkoxy, halogen, nitro, cyano, ($C_1$-$C_4$)alkyl-$S(O)_n$—, ($C_1$-$C_4$)haloalkyl-$S(O)_n$—, ($C_1$-$C_4$)alkoxycarbonyl, ($C_1$-$C_4$)alkylcarbonyl, OH, SH or $R^{10}$; in which $R^{10}$ is phenyl unsubstituted or substituted by one or more radicals selected from the group consisting of halogen, ($C_1$-$C_4$)alkyl, ($C_1$-$C_4$)haloalkyl, ($C_1$-$C_4$)alkoxy, nitro, cyano and ($C_1$-$C_4$)alkyl-$S(O)_n$—.

Preferably Y and Z are each N.

A preferred class of compounds of formula (I) for the use as herbicides or plant growth regulators in the invention are those in which:

A-W is N=N, $N^+(O^-)$=N or NH—NH;

$R^1$, $R^2$, $R^3$ and $R^4$ are each independently H, OH, halogen, nitro, cyano, formyl, amino, carbamoyl, $CO_2H$ or sulfamoyl, or benzyl or also phenoxy,
  where each of the latter two radicals is unsubstituted or substituted by one or more radicals selected from the group consisting of ($C_1$-$C_4$)alkyl, ($C_1$-$C_4$)haloalkyl, halogen, OH, ($C_1$-$C_4$)alkoxy, also ($C_1$-$C_4$)haloalkoxy, ($C_1$-$C_4$)alkyl-$S(O)_n$—, nitro, cyano, amino, ($C_1$-$C_4$)alkylamino, ($C_1$-$C_4$)dialkylamino, ($C_1$-$C_4$)alkoxycarbonyl and $CO_2H$, or are ($C_1$-$C_4$)alkyl, ($C_2$-$C_4$)alkenyl, ($C_2$-$C_4$)alkynyl, ($C_3$-$C_6$)cycloalkyl, ($C_3$-$C_6$)cycloalkyl-($C_1$-$C_4$)alkyl-, ($C_1$-$C_4$)alkoxy, ($C_2$-$C_4$)alkenyloxy, ($C_2$-$C_4$)alkynyloxy, ($C_1$-$C_4$)alkyl-$S(O)_n$—, ($C_1$-$C_4$)alkylamino, ($C_1$-$C_4$)dialkylamino, ($C_1$-$C_4$)alkoxycarbonyl, ($C_1$-$C_4$)alkylcarbonyl, ($C_1$-$C_4$)alkylcarbamoyl, ($C_1$-$C_4$)dialkylcarbamoyl, ($C_1$-$C_4$)alkylsulfamoyl or ($C_1$-$C_4$)dialkylsulfamoyl,
  where each of the 18 last-mentioned radicals is unsubstituted or substituted by one or more radicals selected from the group consisting of halogen, OH, ($C_1$-$C_4$)alkoxy, ($C_1$-$C_4$)alkyl-$S(O)_n$— and in the case of cyclic radicals also ($C_1$-$C_6$)alkyl and ($C_1$-$C_6$)haloalkyl;

X is N or $CR^7$;

$R^7$ is H, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy, halogen, nitro, cyano, ($C_1$-$C_4$)alkyl-$S(O)_n$—, ($C_1$-$C_4$)haloalkyl-$S(O)_n$—, $S(O)_nR^{10}$, $S(O)_nCH_2CO_2R^{11}$, $S(O)_nCH_2CO_2N[(C_1$-$C_4$)alkyl]_2$, $S(O)_nCH_2CONR^{12}R^{13}$, $S(O)_nCH_2CONR^{14}NR^{15}$, ($C_1$-$C_4$)alkoxycarbonyl, formyl, ($C_1$-$C_4$)alkylcarbonyl, ($C_1$-$C_4$)haloalkylcarbonyl, carbamoyl, ($C_1$-$C_4$)alkylcarbamoyl, ($C_1$-$C_4$)dialkylcarbamoyl, OH, SH, $R^{10}$, $NR^{16}R^{17}$ or 1,3-dioxolan-2-yl; in which $R^{10}$ is $(CH_2)_m$phenyl unsubstituted or substituted by one or more radicals selected from the group consisting of halogen, ($C_1$-$C_4$)alkyl, ($C_1$-$C_4$)haloalkyl, ($C_1$-$C_4$)alkoxy, ($C_1$-$C_4$)haloalkoxy, nitro, cyano, ($C_1$-$C_4$)alkyl-$S(O)_n$—, ($C_1$-$C_4$)haloalkyl-$S(O)_n$—, amino, ($C_1$-$C_4$)alkylamino, ($C_1$-$C_4$)dialkylamino, ($C_1$-$C_4$)alkylcarbonyl, carbamoyl, ($C_1$-$C_4$)alkylcarbamoyl, ($C_1$-$C_4$)dialkylcarbamoyl, sulfamoyl, ($C_1$-$C_4$)alkylsulfamoyl and ($C_1$-$C_4$)dialkylsulfamoyl;

$R^{11}$ is H or ($C_1$-$C_4$)alkyl;

$R^{12}$ and $R^{13}$, or $R^{16}$ and $R^{17}$ are each independently H, ($C_1$-$C_4$)alkyl or $R^{10}$; or $R^{12}$ and $R^{13}$, or $R^{16}$ and $R^{17}$ together with the respective attached N atom form a five- or six-membered saturated ring which optionally contains an additional hetero atom in the ring which is selected from O,S and N, the ring being unsubstituted or substituted by one or more radicals selected from halogen, ($C_1$-$C_4$)alkyl and ($C_1$-$C_4$)haloalkyl; and $R^{14}$ and $R^{15}$ are each independently H or ($C_1$-$C_4$)alkyl; and Y and Z are each N.

A more preferred class of compounds of formula (I) for the use as herbicides or plant growth regulators in the invention are those in which:

A-W is N=N, $N^+(O^-)$=N or NH—NH;

$R^1$, $R^2$, $R^3$ and $R^4$ are each independently H, ($C_1$-$C_4$)alkyl, ($C_1$-$C_4$)haloalkyl, ($C_1$-$C_4$)alkoxy, OH, halogen, nitro, cyano, ($C_1$-$C_4$)alkyl-$S(O)_n$—, ($C_1$-$C_4$)haloalkyl-$S(O)_n$—, amino, ($C_1$-$C_4$)alkylamino, ($C_1$-$C_4$)dialkylamino, ($C_1$-$C_4$)alkoxycarbonyl, formyl, ($C_1$-$C_4$)alkylcarbonyl, carbamoyl, ($C_1$-$C_4$)alkylcarbamoyl or ($C_1$-$C_4$)dialkylcarbamoyl;

X is N or $CR^7$ wherein $R^7$ is H, ($C_1$-$C_4$)alkyl, ($C_1$-$C_4$)haloalkyl, ($C_1$-$C_4$)alkoxy, halogen, nitro, cyano, ($C_1$-$C_4$)alkyl-$S(O)_n$—, ($C_1$-$C_4$)haloalkyl-$S(O)_n$—, ($C_1$-$C_4$)alkoxycarbonyl, ($C_1$-$C_4$)alkylcarbonyl, OH, SH or $R^{10}$; in which $R^{10}$ is phenyl unsubstituted or substituted by one or more radicals selected from the group consisting of halogen, ($C_1$-$C_4$)alkyl, ($C_1$-$C_4$)haloalkyl, ($C_1$-$C_4$)alkoxy, nitro, cyano and ($C_1$-$C_4$)alkyl-$S(O)_n$—; and Y and Z are each N.

A further preferred class of compounds for the use as herbicides or plant growth regulators in the invention, is of formula (Ij) or (Ik), as depicted hereinafter, in which:

A-W is N=N, $N^+(O^-)$=N or $N^5$—$NR^6$;

$R^1$, $R^2$, $R^3$ and $R^4$ are each independently H, ($C_1$-$C_4$)alkyl, ($C_1$-$C_4$)haloalkyl, ($C_1$-$C_4$)alkoxy or halogen;

$R^5$ and $R^6$ are each independently H, ($C_1$-$C_4$)alkyl, ($C_2$-$C_4$)alkenyl, ($C_1$-$C_4$)alkylcarbonyl, $COR^{10}$, ($C_1$-$C_4$)alkoxy-($C_1$-$C_4$)alkyl- or $R^{10}$;

X is N or $CR^7$, in which $R^7$ is H, ($C_1$-$C_4$)alkyl, ($C_1$-$C_4$)haloalkyl, ($C_1$-$C_4$)alkoxy, halogen, nitro, cyano, ($C_1$-$C_4$)alkyl-$S(O)_n$—, $S(O)_nCH_2CO_2R^{11}$, $S(O)_nCH_2CONR^{12}R^{13}$, $S(O)_nCH_2CONR^{14}NR^{15}$, ($C_1$-$C_4$)alkoxycarbonyl, ($C_1$-$C_4$)alkylcarbonyl, ($C_1$-$C_4$)dialkylcarbamoyl, SH, $R^{10}$ or $NR^{16}R^{17}$;

$R^{10}$ is $(CH_2)_m$phenyl unsubstituted or substituted by one or more halogen radicals;

$R^{11}$ is H;

$R^{12}$ and $R^{13}$ are each $(C_1$-$C_4)$alkyl; or $R^{12}$ and $R^{13}$ together with the attached N atom form a morpholine ring;

$R^{14}$ and $R^{15}$ are each H;

$R^{16}$ is H;

$R^{17}$ is CH$_2$phenyl; and

Y and Z are each N.

Especially preferred compounds of formula (I) for the use as herbicides or plant growth regulators in the invention are those in which:

A-W is N=N, N$^+$(O$^-$)=N or NH—NH;

$R^1$, $R^2$, $R^3$ and $R^4$ are each independently H, $(C_1$-$C_4)$alkyl, $(C_1$-$C_4)$haloalkyl, $(C_1$-$C_4)$alkoxy or halogen;

X is N or CR$^7$, in which $R^7$ is H, $(C_1$-$C_4)$alkyl, $(C_1$-$C_4)$haloalkyl, $(C_1$-$C_4)$alkoxy, halogen, nitro, cyano, $(C_1$-$C_4)$alkyl-S(O)$_n$— or $R^{10}$; and $R^{10}$ is $(CH_2)_m$phenyl unsubstituted or substituted by one or more halogen radicals.

Some of the compounds of formula (I) are new, and a further feature of the invention relates to the new compounds.

A preferred class of novel compounds are of formula (Ii):

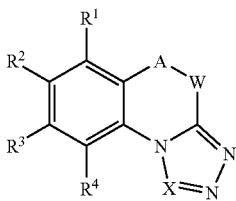

wherein:

A-W is N=N, N$^+$(O$^-$)=N or NH—NH, in which A represents the atom or substituted atom shown on the left side of the groups representing A-W;

X is N or CR$^7$;

$R^1$, $R^2$, $R^3$ and $R^4$ are as defined above;

$R^7$ is H, $(C_1$-$C_6)$alkyl, $(C_1$-$C_6)$haloalkyl, $(C_2$-$C_6)$alkenyl, $(C_2$-$C_6)$alkynyl, $(C_1$-$C_6)$alkoxy, $(C_1$-$C_6)$haloalkoxy, halogen, nitro, cyano, $(C_1$-$C_6)$alkyl-S(O)$_n$—, $(C_1$-$C_6)$haloalkyl-S(O)$_n$—, $(C_1$-$C_6)$alkoxycarbonyl, formyl, $(C_1$-$C_6)$alkylcarbonyl, $(C_1$-$C_6)$haloalkylcarbonyl, carbamoyl, $(C_1$-$C_6)$alkylcarbamoyl, $(C_1$-$C_6)$dialkylcarbamoyl, NR$^{16}$R$^{17}$ or 1,3-dioxolan-2-yl; and $R^{16}$ and $R^{17}$ are each independently H, $(C_1$-$C_6)$alkyl or $R^{10}$, wherein $R^{10}$ is as defined above; with the exclusion of compounds wherein:

i) A-W is N=N; $R^1$, $R^2$, $R^3$ and $R^4$ are each H; and X is CBr, CSO$_2$Me, CSMe, CMe or CH;

ii) A-W is N=N; $R^1$, $R^3$ and $R^4$ are each H; $R^2$ is Cl; and X is CH;

iii) A-W is N=N; $R^2$, $R^3$ and $R^4$ are each H; $R^1$ is OH; and X is CH;

iv) A-W is N$^+$(O$^-$)=N; $R^1$, $R^2$, $R^3$ and $R^4$ are each H; and X is CH;

v) A-W is NH—NH; $R^1$, $R^2$, $R^3$ and $R^4$ are each H; and X is CSMe or CH;

vi) A-W is NH—NH; $R^1$, $R^3$ and $R^4$ are each H; $R^2$ is Me; and X is CH;

vii) A-W is N=N; $R^1$, $R^2$ and $R^4$ are each H; $R^3$ is OMe; and X is N;

viii) A-W is N=N; $R^1$, $R^3$ and $R^4$ are each H; $R^2$ is OMe, Me or H; and X is N;

ix) A-W is N=N; $R^1$ and $R^3$ are each H; $R^2$ and $R^4$ are each Me; and X is N;

x) A-W is N$^+$(O$^-$)=N; $R^1$, $R^3$ and $R^4$ are each H; $R^2$ is Me or OMe; and X is N;

xi) A-W is N$^+$(O$^-$)=N; $R^1$ and $R^3$ are each H; $R^2$ and $R^4$ are each Me; and X is N; and xii) A-W is NH—NH; $R^1$, $R^2$, $R^3$ and $R^4$ are each H; and X is N.

The above compounds i) to xii) are specifically excluded because they are known, as disclosed in the following references. Their use as a herbicide or plant growth regulator, however, has not been reported:

E. Gy. T. Gyogyszervegyeszeti Gyar, in U.S. Pat. No. 4,316,022;

Messmer, Hajos, Benko and Pallos, in Acta Chimica Academiae Scientiarum Hungaricae (1980),105(3),189-99;

Messmer, Hajos, Benko and Pallos, in Magyar Kemiai Folyoirat (1980), 86(10), 471-6;

Messmer, Hajos, Tamas and Neszmelyi, in J. Org. Chem. (1979),44(11),1823-5;

Sasaki and Murata, in Chemische Berichte (1969), 102(11), 3818-23;

Gorjan, Klemenc, Staric, Stanovnik and Tisler, in Monatshefte für Chemie (1976), 107(5), 1199-208;

Bartra, Urpi and Vilarrasa, in Tetrahedron Letters (1987), 28(47), 5941-4;

Asaad and El Ashry, in Zeitschrift für Naturforschung A: Physical Sciences (1996), 51(9), 1012-1018;

Fos, Vilarrasa and Fernandez, in Journal of Organic Chemistry (1985), 50(24), 4894-9;

Messmer, Hajos, Benko and Pallos, in Magyar Kemiai Folyoirat (1974), 80(12), 527-30;

Messmer, Hajos, Benko and Pallos, in J. Het. Chem. (1973), 10(4), 575-8; Castillon, Pascual and Vilarrasa, in J. Org. Chem. (1982), 47(20), 3886-90.

Compounds of formula (I) above may be prepared by the application or adaptation of known methods (i.e. methods heretofore used or described in the literature), and as hereinafter described.

In the following description where symbols appearing in formulae are not specifically defined, it is to be understood that they are "as hereinbefore defined" in accordance with the first definition of each symbol in the specification or in the preferred definitions.

It is to be understood that in the descriptions of the following processes the sequences may be performed in different orders, and that suitable protecting groups may be required to achieve the compounds sought.

According to a feature of the present invention compounds of formula (I) where A-W is N=N or N$^+$(O$^-$)=N (preferably where A-W is N=N), and the other values are as defined above, may be prepared by cyclodehydrating the compound of formula (II):

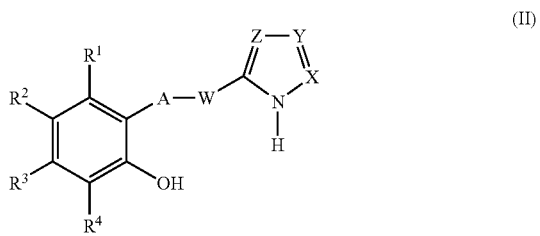

wherein A-W is N=N or N⁺(O⁻)=N, and $R^1$, $R^2$, $R^3$, $R^4$, A, W, X, Y and Z are as defined above, for example as described by Villarrasa and Granados in J. Het. Chem. (1974), 11, 867-872.

The intramolecular condensation is generally performed in situ, by heating in the presence or absence of a solvent such as an alcohol for example methanol or ethanol, or a glycol such as ethylene glycol, or acetic acid or sulfuric acid, at a temperature of from 0° C. to the reflux temperature of the solvent, preferably from 0° C. to 100° C.

According to a further feature of the present invention compounds of formula (I) wherein A-W is N=N, and the other values are as defined above, may also be prepared by the coupling of a diazonium salt of formula (III):

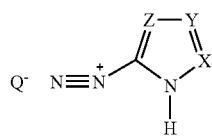

(III)

wherein X, Y and Z are as defined above and Q is a chloride, sulfate or fluoroborate, with a compound of formula (IV):

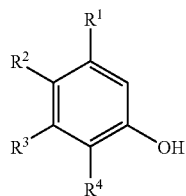

(IV)

wherein $R^1$, $R^2$, $R^3$ and $R^4$ are as defined above, to give an azo intermediate of formula (II) wherein A-W is N=N, followed by the above described cyclodehydration.

In order to avoid the competing coupling reacting which may occur when $R^2$ is H, then the $R^2$ group may be replaced by a blocking group such as $SO_3H$, which can subsequently be removed by known procedures.

The diazonium salts of formula (III) are generally prepared in situ by the diazotisation reaction of a compound of formula (V):

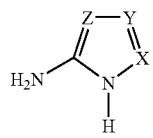

(V)

wherein X, Y and Z are as defined above, using a nitrite salt generally an alkali metal nitrite, preferably sodium nitrite, in a mineral acid, for example aqueous hydrochloric acid, sulfuric acid or phosphoric acid, optionally with a co-solvent such as acetic acid, at a temperature of from −20° C. to 100° C., preferably 0° C. to 20° C.

According to a further feature of the present invention compounds of formula (I) wherein A-W is $N^5$—$NR^6$; $R^1$, $R^2$, $R^3$; $R^4$, $R^6$, X, Y and Z are as defined above, and $R^5$ is as defined in formula (I) with the exclusion of H, may be prepared by the alkylation, acylation or sulfonylation of the corresponding compound of formula (I) wherein $R^5$ is H, with a compound of formula (VI):

$$R^5\text{-L} \qquad (VI)$$

wherein $R^5$ is as defined above with the exclusion of H, and L is a leaving group. For alkylations, where $R^5$ is $(C_1\text{-}C_6)$alkyl, $(C_1\text{-}C_6)$haloalkyl, $(C_2\text{-}C_6)$alkenyl, $(C_2\text{-}C_6)$alkynyl, $(C_1\text{-}C_6)$alkoxy-$(C_1\text{-}C_6)$alkyl- or $R^{10}$, L is preferably halogen, alkylsulfonyloxy or arylsulfonyloxy (more preferably chlorine, bromine, iodine, methylsulfonyloxy or p-toluenesulfonyloxy). A base is optionally present in the reaction which is generally performed in an inert solvent such as tetrahydrofuran, dioxan, acetonitrile, toluene, diethyl ether, dichloromethane, dimethylsulfoxide or N,N-dimethylformamide, at a temperature of from −30° C. to 200° C., preferably at 20° C. to 100° C. The base is generally an alkali metal hydroxide such as potassium hydroxide, an alkali metal hydride such as sodium hydride, an alkali metal carbonate such as potassium carbonate or sodium carbonate, an alkali metal alkoxide such as sodium methoxide, an alkaline earth metal carbonate such as calcium carbonate, or an organic base such as a tertiary amine, for example triethylamine or ethyldiisopropylamine, or pyridine, or 1,8-diazabicyclo[5.4.0]undec-7-en (DBU). For acylations, where $R^5$ is formyl, $(C_1\text{-}C_6)$alkylcarbonyl, $(C_2\text{-}C_6)$alkenylcarbonyl, $COR^{10}$ or $(C_1\text{-}C_6)$alkoxycarbonyl, (VI) is preferably an acid halide where L is preferably chlorine or bromine (more preferably chlorine), or an acid anhydride where L is $R^5$—$CO_2$—. A base is optionally present in the the reaction, which is generally performed using similar bases, solvents and temperatures as employed for the alkylations.

For sulfonylations, where $R^5$ is $SO_2(C_1\text{-}C_6)$alkyl, (VI) is preferably a sulfonyl halide where L is preferably chlorine or bromine (more preferably chlorine). A base is optionally present in the the reaction, which is generally performed using similar bases, solvents and temperatures as employed for the alkylations.

According to a further feature of the present invention compounds of formula (I) wherein A-W is $N^5$—$NR^6$; $R^1$, $R^2$, $R^3$; $R^4$, $R^5$, X, Y and Z are as defined above, and $R^6$ is as defined in formula (I) with the exclusion of H, may be prepared by the alkylation, acylation or sulfonylation of the corresponding compound of formula (I) wherein $R^6$ is H, with a compound of formula (VII):

$$R^6\text{-L} \qquad (VII)$$

wherein $R^6$ is as defined above with the exclusion of H, and L is a leaving group. The process may be performed using similar conditions as employed for the above processes which use the compound of formula (VI).

The above alkylation, acylation or sulfonylation processes may be adapted to prepare a desired combination of $R^5$ and $R^6$ values, by starting from the corresponding compounds of formula (I) in which $R^5$ and $R^6$ are each H, and performing the alkylation, acylation or sulfonylation reactions in a sequential manner. Suitable protecting agents well known in the art may also be used to effect an efficient preparation of certain combinations of $R^5$ and $R^6$.

According to a further feature of the present invention compounds of formula (I) wherein A-W is $N^5$—$NR^6$, $R^5$ and $R^6$ are each H, and the other values are as defined above, may be prepared by the reduction of the corresponding compound of formula (I) wherein A-W is N=N.

Reductions are generally performed using a reducing agent such as sodium dithionite, in a solvent such as water, alcohols such as methanol or ethanol, or N,N-dimethylformamide, or using a complex metal hydride such as sodium borohydride or lithium aluminium hydride, in a solvent such as tetrahydrofuran, diethyl ether, dioxan, N,N-dimethylformamide or dimethylsulfoxide, at a temperature of from 0° C. to 100° C. A base such as a metal carbonate, trialkylamine or pyridine is optionally present in the reaction.

Reduction may also be achieved by hydrogenation using hydrogen or hydrogen producing reagents, generally in the presence of a catalyst such as palladium, ruthenium or rhodium, in a solvent such as methanol, ethanol, water, tetrahydrofuran or ethyl acetate, at a temperature of from 0° C. to 100° C., and at atmospheric pressure or up to 300 bar.

According to a further feature of the present invention compounds of formula (I) wherein A-W is N=N, and the other values are as defined above, may be prepared by the reduction of the corresponding compound of formula (I) wherein A-W is $N^+(O^-)$=N.

The reaction may be performed using similar conditions described above for the reduction of compounds wherein A-W is N=N, to give compounds wherein A-W is NH—NH. By controlling the amount of reducing or hydrogenating agent and choice of reaction time and/or temperature the over-reduction to compounds wherein A-W is NH—NH can be avoided or minimised.

According to a further feature of the present invention compounds of formula (I) wherein A-W is $N^5$—$NR^6$, $R^5$ and $R^6$ are each H, and the other values are as defined above, may also be prepared by the reduction of the corresponding compound of formula (I) wherein A-W is $N^+(O^-)$=N.

The reaction may be performed using similar conditions described above for the preparation of compounds wherein A-W is N=N, but generally by using an increased amount of reducing or hydrogenating agent, longer reaction time and/or increased reaction temperature.

According to a further feature of the present invention compounds of formula (I) wherein A-W is N=N or $N^+(O^-)$=N, X is $CR^7$, Y and Z are each N, and the other values are as defined above, may be prepared by the reaction of a compound of formula (VIII):

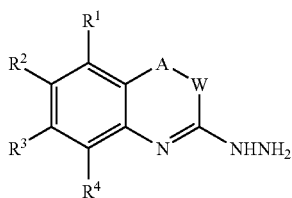

(VIII)

wherein A-W is N=N or $N^+(O^-)$=N, $R^7$ is H, $(C_1-C_6)$alkyl, $(C_1-C_6)$haloalkyl, $(C_2-C_6)$alkenyl, $(C_2-C_6)$alkynyl or $R^{10}$, and $R^1$, $R^2$, $R^3$ and $R^4$ are as defined above, with a carboxylic acid or an equivalent thereof of formula (IX) or (X):

$R^7COL^1$            (IX)

$R^7C(OR)_3$            (X)

wherein $R^7$ is H, $(C_1-C_6)$alkyl, $(C_1-C_6)$haloalkyl, $(C_2-C_6)$alkenyl, $(C_2-C_6)$alkynyl or $R^{10}$, and $L^1$ is H or a leaving group, generally halogen and preferably chlorine, or $L^1$ is alkoxy or —$OCOR^7$, and R is $(C_1-C_6)$alkyl preferably methyl or ethyl.

The reaction is generally performed using an inert solvent, for example benzene, toluene, xylene or decaline, or using equimolecular amounts or an excess of reagent (IX) or (X) in the absence of a solvent, optionally in the presence of a dehydrating agent such as sulfuric acid or polyphosphoric acid, at a temperature of from 0° C. to 250° C., for example as described by Messmer, Hajos, Benko and Pallos in Acta Chimica Academiae Scientiarum Hungaricae (1980), 103(2), 123-133.

According to a further feature of the present invention compounds of formula (I) wherein A-W is N=N or $N^+$ ($O^-$)=N, X is $CR^7$, Y and Z are each N, and the other values are as defined above, may also be prepared by the cyclisation of a compound of formula (XI):

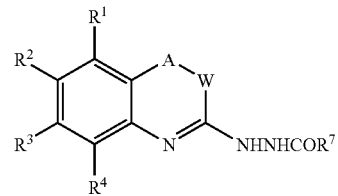

(XI)

wherein A-W is N=N or $N^+(O^-)$=N, $R^7$ is H, $(C_1-C_6)$alkyl, $(C_1-C_6)$haloalkyl, $(C_2-C_6)$alkenyl, $(C_2-C_6)$alkynyl or $R^{10}$, and $R^1$, $R^2$, $R^3$ and $R^4$ are as defined above.

The reaction is generally performed in the presence of a dehydrating agent such as sulfuric acid or polyphosphoric acid, or an orthoester for example ethyl orthoformate, or an anhydride, for example acetic anhydride, or by treatment with a halogenating agent such as phosphoryl chloride, a phosphorus pentahalide, a phosphorus trihalide, a triphenylphosphine dihalide, phosgene or phenylsulfonyl chloride. The reaction is generally performed using an inert solvent, for example acetonitrile, acetone or tetrachloromethane, optionally in the presence of a base, which may be an organic base such as a tertiary amine, for example triethylamine or ethyldiisopropylamine, or pyridine, or 1,8-diazabicyclo[5.4.0]undec-7-en (DBU), or an inorganic base such as an alkali metal carbonate, for example potassium carbonate or sodium carbonate, at a temperature of from −20° C. to 180° C., for example as described by Wamhof and Zahran in Synthesis (1987), 876.

According to a further feature of the present invention compounds of formula (Ia), wherein A-W is N=N or $N^+(O^-)$ =N, and $R^1$, $R^2$, $R^3$ and $R^4$ are as defined above, are generally in tautomeric equilibria with the corresponding azido form of formula (Ib), and may be prepared by the reaction of a compound of formula (XII):

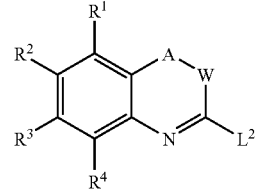

(XII)

wherein A-W is N=N or $N^+(O^-)$=N, $R^1$, $R^2$, $R^3$ and $R^4$ are as defined above, and $L^2$ is a leaving group, generally halogen, alkylsulfonyl, alkylsulfenyl or alkylsulfinyl, or an alkyl-, haloalkyl- or arylsulfonyloxy group (preferably chlorine), with a metal azide of formula (XIII):

$M-N_3$            (XIII)

wherein M is an alkali metal such as sodium azide or lithium azide. The reaction is generally performed using an inert solvent, for example N,N-dimethylformamide, dimethylsulfoxide, tetrahydrofuran, ethyl acetate or dioxan, at a temperature of from −20° C. to 200° C., following general methods described in the literature as for example by Biffin, Miller and Paul in Patai, "The Chemistry of the Azido Group", pp. 57-119, Interscience, New York, 1971.

Alternatively, the corresponding azido compounds of general formula (IB) wherein A-W is N=N or $N^+(O^-)$=N, and $R^1$, $R^2$, $R^3$ and $R^4$ are as defined above, may be prepared by the reaction of the corresponding compound of general formula (VIII) with nitrous acid according to the general procedure described by Messmer, Hajos, 25 Benko and Pallos in J. Het. Chem. (1973), 10(4), 575-8.

According to a further feature of the present invention compounds of formula (I) wherein A-W is $N^+(O^-)$=N, and the other values are as defined above, may be prepared by the oxidation of the corresponding compound of formula (I) in which A-W is N=N. The reaction is generally performed using an oxidant such as a peracid for example m-chloroperbenzoic acid, or a hydroperoxide, in an inert solvent, for example water, tetrachloromethane, chloroform, trifluoroacetic acid, acetic acid or trifluoroacetic anhydride, at a temperature of from −30° C. to 120° C., following general methods as described in "Methoden der Organischen Chemie" Bd. IV/1a, pp. 304-313, 4. Edition; Georg Thieme Verlag, Stuttgart New York ISBN-3-13-200704-8 (1981).

Intermediates of formula (II) where A-W is $N^+(O^-)$=N, may be prepared from the corresponding compounds in which A-W is N=N, using the above described methods for obtaining the corresponding compounds of formula (I).

Intermediates of formula (VIII) may be prepared by the reaction of compounds of formula (XII) with hydrazine hydrate, or a salt thereof such as the hydrochloride salt according to known methods.

Intermediates of formula (XI) may be prepared from intermediates of formula (VIII) according to known methods, for example as described by Sasaki, Murata and Masayoshi in Chem. Ber. (1969),102(11), 3818-3823.

The following acids, for example, are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures from 0 to 100° C., and they can be isolated in a known manner, for example by filtration, and, if appropriate, purified by washing with an inert organic solvent.

The base addition salts of the compounds of the formula (I) are preferably prepared in inert polar solvents such as, for example, water, methanol or acetone at temperature from 0 to 100° C. Examples of suitable bases for preparing the salts according to the invention are alkali metal carbonates, such as potassium carbonate, alkali metal and alkaline earth metal hydroxides, for example NaOH or KOH, alkali metal and alkaline earth metal hydrides, for example NaH, alkali metal and alkaline earth metal alkoxides, for example sodium methoxide, potassium tert-butoxide, or ammonia or ethanolamine. Quaternary ammonium salts can be obtained, for example, by salt exchange or condensation with quaternary ammonium salts of the formula $[NRR'R''R''']^+U^-$ where R, R', R'' and R''' independently of one another are $(C_1-C_4)$alkyl, phenyl or-benzyl and $U^-$ is an anion, for example $Cl^-$ or $OH^-$ Certain compounds of formula (II) are novel and as such form a further feature of the invention.

Compounds of formula (III), (IV), (V), (VI), (VII), (IX), (X), (XII) and (XIII) are known or may be prepared according to known methods.

A collection of compounds of formula (I) which can be synthesized by the abovementioned processes can additionally be prepared in parallel fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallel fashion, a series of commercially available apparatuses can be used as they are available from, for example, Stem Corporation, Woodrolfe Road, Tollesbury, Essex, CM9 8SE, England or H+P Labortechnik GmbH, Bruckmannring 28, 85764 Oberschleissheim, Germany. To carry out the parallel purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operation has to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds of formula (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998. The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131-5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds of formula (I) in the form of substance collections or substance libraries. Subject matter of the present invention are therefore also libraries of the compounds of formula (I) which contain at least two compounds of formula (I), and of their precursors.

The following non-limiting Examples illustrate the preparation of the compounds of formula (I).

A. CHEMICAL EXAMPLES

In the Examples which follow, quantities (also percentages) are weight based unless stated otherwise.

Example A1

7-Methoxy-1-methyl[1,2,4]triazolo[3,4-c][1,2,4]benzotriazine

A mixture of 3-hydrazino-7-methoxy-1,2,4-benzotriazine (0.5 g, 2.62 mmol) and 1,1,1-triethoxyethane (4.24 g, 26.15 mmol) was heated at 145° C. for 3 h, and the ethanol formed during the reaction was distilled off continuously. After cooling in a refrigerator for 12 h, the solid filtered off and washed with ether to give 7-methoxy-1-methyl[1,2,4]triazolo[3,4-c][1,2,4]benzotriazine (Compound Number 1, 0.5 g, 88% yield), 1H-NMR (300 MHz; CDCl$_3$): 8.14 ppm (d, 1H, H-9); 8.14 ppm (d, 1H, H-9); 7.62 ppm (dd, 1H, H-8); 4.05 ppm (s, 3H, OMe); 3.19 ppm (s, 1H, CH$_3$) (Compound no. 1 in table 1).

By proceeding in a similar manner starting from the appropriate starting materials the following compounds were also prepared:

7-methoxy-1-ethyl[1,2,4]triazolo[3,4-c][1,2,4]benzotriazine (Compound Number 2), 1H-NMR (300 MHz; DMSO): 8.19 ppm (d, 1H, H-6); 8.05 ppm (d, 1H, H-9); 7.59 ppm (dd, 1H, H-8); 4.06 (s, 3H, OCH$_3$); 3.49 ppm (q, 2H, CH$_2$); 1.69 ppm (t, 3H, CH$_3$) [1,2,4]triazolo[3,4-c][1,2,4]benzotriazine (Compound Number 3), m.p. 259-261° C.; and 7,9-dichloro[1,2,4]triazolo[3,4-c][1,2,4]benzotriazine (Compound Number 4), 1H-NMR (300 MHz; DMSO): 10.43 ppm (s, 1H, H-1); 8.95 ppm and 8.52 ppm (two d, each 1H, H-6 and H-8).

Example A2

7-Bromo[1,2,4]triazolo[3,4-c][1,2,4]benzotriazine-5-oxide

A mixture of 7-bromo-3-hydrazino-1,2,4-benzotriazine 1-oxide (1 g, 3.91 mmol) and 1,1,1-triethoxymethane (6.24 g, 42.08 mmol) was heated to 145° C. for 3 h, and the ethanol formed during the reaction was continuously distilled off. After cooling in a refrigerator for 12 h, the solid filtered off and washed with ether to give 7-bromo[1,2,4]triazolo[3,4-c][1,2,4]benzotriazine-5-oxide, (Compound Number 5, 0.68 g, 63% yield), 1H-NMR (300 MHz; DMSO): 9.95 ppm (s,1H, H-1); 8.60 ppm (d,1H, H-6); 8.47 ppm (d, 1H, H-9) and 8.38 ppm (dd,1H, H-8).

Example A3

4,5-Dihydro[[1,2,4]triazolo[3,4-c][1,2,4]benzotriazine

Ethanol (3 ml) was added dropwise to a suspension of [1,2,4]triazolo[3,4-c][1,2,4]benzotriazine (1.3 g, 7.6 mmol) and sodium dithionite (1.55 g, 8.9 mmol) in water (20 ml). The reaction mixture was stirred for 3 h. The precipitate was filtered off and washed with ether to give 4,5-dihydro[[1,2,4]triazolo[3,4-c][1,2,4]benzotriazine, (Compound Number 6, 1.16 g, 88% yield), 1H-NMR (300 MHz; DMSO): 8.97 ppm (s, 1H, H-1); 7.80 ppm (broad s, 1H, N-H); 7.55 ppm (d,1H, H-9); 7.48 ppm (s, 1H, NH); 7.13 and 7.02 (two dd, each 1H, H-7 and H-8) and 6.93 ppm (d, 1H, H-6).

The compounds of formula (Ij) to (Iq) shown in the following Tables 1 to 8 are preferred for the use as herbicides or plant growth regulators in the invention, and are obtained by, or analogously to, the above Examples A1 to A3 or the above-described general methods.

The following abbreviations are used in the Tables 1 to 8:
"Me" means methyl, "Et" means ethyl, "nPr" means n-propyl, "iPr" means isopropyl, "nBu" means n-butyl, "OMe" means methoxy, "OEt" means ethoxy, "Ph" means phenyl, "OPh" means phenoxy and "CO-3F-Ph" means a 3-fluorobenzoyl radical.

"Cpd" means Compound Number. Compound numbers are given for reference purposes only.

"mp." means melting point (in ° C.)

"(Ref.)" means that reference is made to example no. or other data such as NMR data at the end of the respective table.

Characterising data for Compound Numbers 1 to 6 are shown in the above Examples A1 to A3.

TABLE 1

Compounds of formula (Ij)

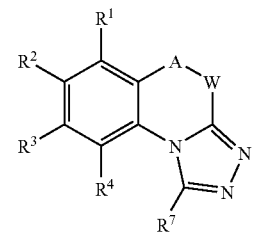

(Ij)

| Cpd | R$^1$ | R$^2$ | R$^3$ | R$^4$ | -A-W- | R$^7$ | mp. ° C. (Ref.) |
|---|---|---|---|---|---|---|---|
| 1 | H | OMe | H | H | —N=N— | Me | (see A1) |
| 2 | H | OMe | H | H | —N=N— | Et | 307 |
| 3 | H | H | H | H | —N=N— | H | 259-261 |
| 4 | H | Cl | H | Cl | —N=N— | H | (see A2) |
| 5 | H | Br | H | H | —N$^+$(O$^-$)=N— | H | (see A3) |
| 6 | H | H | H | H | —NH—NH— | H | |
| 7 | H | H | H | H | —NH—NH— | SCH$_2$C(O)NHNH$_2$ | |
| 8 | H | H | H | H | —NH—NH— | SCH$_2$CO$_2$H | |
| 9 | H | H | H | H | —NH—NH— | SCH$_2$C(O)NEt$_2$ | |
| 10 | H | OMe | H | H | —N=N— | SH | |
| 11 | H | Me | H | H | —NH—NH— | SCH$_2$C(O)N-morpholinyl | |

TABLE 1-continued

Compounds of formula (Ij)

$$\text{(Ij)}$$

[Structure: benzene ring fused to triazole via A-W bridge, with substituents $R^1$, $R^2$, $R^3$, $R^4$ on benzene ring and $R^7$ on triazole]

| Cpd | $R^1$ | $R^2$ | $R^3$ | $R^4$ | -A-W- | $R^7$ | mp. °C. (Ref.) |
|---|---|---|---|---|---|---|---|
| 12 | H | Me | H | H | —NH—NH— | $SCH_2C(O)NEt_2$ | |
| 13 | H | Me | H | H | —[N(CH$_2$OMe)]$_2$— | $S—CH_2C(O)NEt_2$ | |
| 14 | H | H | H | H | —N=N— | $NH—CH_2Ph$ | |
| 15 | H | H | H | H | —NH—NH— | $SCH_2C(O)N$-morpholinyl | |
| 16 | H | Cl | H | H | —NH—NH— | $SCH_2CO_2H$ | |
| 17 | H | H | H | H | —[N(CO-3F-Ph)]$_2$— | H | |
| 18 | H | H | H | H | —N=N— | $S—CH_2COOH$ | 251-253 |
| 19 | H | H | H | H | —N=N— | $SCH_2C(O)N$-morpholinyl | 214-216 |
| 20 | H | H | H | H | —N=N— | $SCH_2C(O)NEt_2$ | |
| 21 | H | H | H | H | —N=N— | $SCH_2CO_2H$ | |
| 22 | H | Cl | H | H | —N=N— | $SCH_2C(O)NEt_2$ | |
| 23 | H | Me | H | H | —N=N— | $SCH_2C(O)NEt_2$ | |
| 24 | H | Me | H | H | —N=N— | $SCH_2C(O)N$-morpholinyl | |
| 25 | H | Me | H | H | —N=N— | $SCH_2CO_2H$ | |
| 26 | H | OMe | H | H | —N=N— | $SCH_2C(O)N$-morpholinyl | |
| 27 | H | OMe | H | H | —N=N— | $SCH_2CO_2H$ | |
| 28 | H | OMe | H | H | —N=N— | $SCH_2C(O)NEt_2$ | |
| 29 | H | Cl | H | H | —N=N— | SH | 243-245 |
| 30 | H | Me | H | H | —NH—NH— | H | |
| 31 | H | Cl | H | H | —NH—NH— | H | |
| 32 | H | Me | H | H | —N=N— | H | |
| 33 | H | H | H | H | —NH—NH— | SH | 283 |
| 34 | H | H | H | H | —[N(CO-4Br-Ph)]$_2$— | H | |
| 35 | H | Cl | H | H | —N=N— | H | 253-254 |
| 36 | H | H | H | H | —N$^+$(O$^-$)=N— | SH | |
| 37 | H | Br | H | H | —N$^+$(O$^-$)=N— | Me | |
| 38 | H | OMe | H | H | —N=N— | H | 210-211 |
| 39 | H | H | H | H | —N=N— | $SO_2Me$ | 211 |
| 40 | H | H | H | H | —N$^+$(O$^-$)=N— | H | 298-300 (NMR) |
| 41 | H | OMe | H | H | —N=N— | Ph | (NMR) |
| 42 | H | OMe | H | H | —NH—NH— | H | |
| 43 | H | H | H | H | —N=N— | $CF_3$ | (NMR) |
| 44 | H | H | H | H | —NH—NH— | $CF_3$ | |
| 45 | H | OMe | H | H | —N=N— | $CF_3$ | (NMR) |
| 46 | H | OMe | H | H | —NH—NH— | $CF_3$ | |
| 47 | H | H | H | H | —N=N— | Ph | 240-241 |
| 48 | H | H | H | H | —NH—NH— | Ph | |
| 49 | H | OMe | H | H | —NH—NH— | Ph | |
| 50 | H | H | H | H | —N=N— | OMe | |
| 51 | H | H | H | H | —NH—NH— | OMe | |
| 52 | H | OMe | H | H | —N=N— | OMe | |
| 53 | H | OMe | H | H | —NH—NH— | OMe | |
| 54 | H | H | H | H | —N=N— | OEt | (NMR) |
| 55 | H | H | H | H | —NH—NH— | OEt | |
| 56 | H | OMe | H | H | —N=N— | OEt | |
| 57 | H | OMe | H | H | —NH—NH— | OEt | |
| 58 | H | H | H | H | —[N(CH$_2$CH=CH$_2$)]$_2$— | H | |
| 59 | H | OMe | H | H | —[N(CH$_2$CH=CH$_2$)]$_2$— | H | |
| 60 | H | Cl | H | H | —[N(CH$_2$CH=CH$_2$)]$_2$— | H | |
| 61 | H | H | H | H | —[N(CH$_2$Ph)]$_2$— | H | |
| 62 | H | OMe | H | H | —[N(CH$_2$Ph)]$_2$— | H | |
| 63 | H | Cl | H | H | —[N(CH$_2$Ph)]$_2$— | H | |
| 64 | H | H | H | H | —[N(CH$_2$OMe)]$_2$— | H | |
| 65 | H | OMe | H | H | —[N(CH$_2$OMe)]$_2$— | H | |
| 66 | H | H | H | H | —NMe—NMe— | H | |
| 67 | H | OMe | H | H | —[N(COMe)]$_2$— | H | |
| 68 | H | H | H | H | —[N(COMe)]$_2$— | H | |
| 69 | H | $CF_3$ | H | H | —N=N— | H | |
| 70 | H | $CF_3$ | H | H | —NH—NH— | H | |
| 71 | H | Br | H | H | —N=N— | H | |

TABLE 1-continued

Compounds of formula (Ij)

| Cpd | R¹ | R² | R³ | R⁴ | -A-W- | R⁷ | mp. °C. (Ref.) |
|---|---|---|---|---|---|---|---|
| 72 | H | Br | H | H | —NH—NH— | H | |
| 73 | H | H | Cl | H | —N=N— | H | (NMR) |
| 74 | H | H | Cl | H | —NH—NH— | H | |
| 75 | H | H | H | H | —N=N— | Me | 271-273 |
| 76 | H | H | H | H | —NH—NH— | Me | |
| 77 | H | H | H | H | —N⁺(O⁻)N— | Me | |
| 78 | H | Cl | H | H | —N=N— | Me | |
| 79 | H | Cl | H | H | —NH—NH— | Me | |
| 80 | H | Cl | H | H | —N⁺(O⁻)=N— | Me | |
| 81 | H | H | H | H | —N=N— | Et | 249 |
| 82 | H | H | H | H | —NH—NH— | Et | |
| 83 | H | H | H | H | —N⁺(O⁻)=N— | Et | |
| 84 | H | Cl | H | H | —N=N— | Et | |
| 85 | H | Cl | H | H | —NH—NH— | Et | |
| 86 | H | Cl | H | H | —N⁺(O⁻)=N— | Et | |
| 87 | H | H | H | H | —N=N— | iPr | |
| 88 | H | H | H | H | —NH—NH— | iPr | |
| 89 | H | H | H | H | —N⁺(O⁻)=N— | iPr | |
| 90 | H | H | H | H | —N=N— | Br | |
| 91 | H | Cl | H | H | —NH—NH— | iPr | |
| 92 | H | Cl | H | H | —N⁺(O⁻)=N— | iPr | |
| 93 | H | H | H | H | —N=N— | SMe | 271-273 |
| 94 | H | H | H | H | —NH—NH— | SMe | |
| 95 | H | H | H | H | —N⁺(O⁻)=N— | SMe | |
| 96 | H | Cl | H | H | —N=N— | SMe | |
| 97 | H | Cl | H | H | —NH—NH— | SMe | |
| 98 | H | Cl | H | H | —N⁺(O⁻)=N— | SMe | |
| 99 | H | H | H | H | —N=N— | Cl | |
| 100 | H | H | H | H | —NH—NH— | Cl | |
| 101 | H | H | H | H | —N⁺(O⁻)=N— | Cl | |
| 102 | H | Cl | H | H | —N=N— | Cl | |
| 103 | H | Cl | H | H | —NH—NH— | Cl | |
| 104 | H | Cl | H | H | —N⁺(O⁻)=N— | Cl | |
| 105 | H | H | H | H | —N=N— | NMe₂ | |
| 106 | H | H | H | H | —NH—NH— | NMe₂ | |
| 107 | H | H | H | H | —N⁺(O⁻)=N— | NMe₂ | |
| 108 | H | Cl | H | H | —N=N— | NMe₂ | |
| 109 | H | Cl | H | H | —NH—NH— | NMe₂ | |
| 110 | H | Cl | H | H | —N⁺(O⁻)=N— | NMe₂ | |
| 111 | H | H | H | H | —N=N— | CO₂Me | |
| 112 | H | H | H | H | —NH—NH— | CO₂Me | |
| 113 | H | H | H | H | —N⁺(O⁻)=N— | CO₂Me | |
| 114 | H | Cl | H | H | —N=N— | CO₂Me | |
| 115 | H | Cl | H | H | —NH—NH— | CO₂Me | |
| 116 | H | Cl | H | H | —N⁺(O⁻)=N— | CO₂Me | |
| 117 | H | H | H | H | —N=N— | COMe | |
| 118 | H | H | H | H | —NH—NH— | COMe | |
| 119 | H | H | H | H | —N⁺(O⁻)=N— | COMe | |
| 120 | H | Cl | H | H | —N=N— | COMe | |
| 121 | H | Cl | H | H | —NH—NH— | COMe | |
| 122 | H | Cl | H | H | —N⁺(O⁻)=N— | COMe | |
| 123 | H | H | H | H | —N=N— | CONMe₂ | |
| 124 | H | H | H | H | —NH—NH— | CONMe₂ | |
| 125 | H | H | H | H | —N⁺(O⁻)=N— | CONMe₂ | |

TABLE 1-continued

Compounds of formula (Ij)

(Ij)

| Cpd | R¹ | R² | R³ | R⁴ | -A-W- | R⁷ | mp. °C. (Ref.) |
|---|---|---|---|---|---|---|---|
| 126 | H | Cl | H | H | —N=N— | $CONMe_2$ | |
| 127 | H | Cl | H | H | —NH—NH— | $CONMe_2$ | |
| 128 | H | Cl | H | H | —N⁺(O⁻)=N— | $CONMe_2$ | |
| 129 | H | H | H | H | —N=N— | $CH_2Ph$ | |
| 130 | H | H | H | H | —NH—NH— | $CH_2Ph$ | |
| 131 | H | H | H | H | —N⁺(O⁻)=N— | $CH_2Ph$ | |
| 132 | H | Cl | H | H | —N=N— | $CH_2Ph$ | |
| 133 | H | Cl | H | H | —NH—NH— | $CH_2Ph$ | |
| 134 | H | Cl | H | H | —N⁺(O⁻)=N— | $CH_2Ph$ | |
| 135 | H | H | H | H | —N=N— | CN | |
| 136 | H | H | H | H | —NH—NH— | CN | |
| 137 | H | H | H | H | —N⁺(O⁻)=N— | CN | |
| 138 | H | Cl | H | H | —N=N— | CN | |
| 139 | H | Cl | H | H | —NH—NH— | CN | |
| 140 | H | Cl | H | H | —N⁺(O⁻)=N— | CN | |
| 141 | H | H | H | H | —N=N— | $NO_2$ | |
| 142 | H | H | H | H | —NH—NH— | $NO_2$ | |
| 143 | H | H | H | H | —N⁺(O⁻)=N— | $NO_2$ | |
| 144 | H | Cl | H | H | —N=N— | $NO_2$ | |
| 145 | OAc | H | H | H | —N=N— | H | 180 |
| 146 | OH | H | H | H | —N=N— | H | 276-278 |
| 147 | H | OMe | H | H | —N=N— | SMe | (NMR) |
| 148 | H | OMe | H | H | —NH—NH— | Me | (NMR) |
| 149 | H | H | H | H | —N=N— | nPr | (NMR) |
| 150 | H | OMe | H | H | —N=N— | $SO_2Me$ | (NMR) |
| 151 | H | OMe | H | H | —N=N— | nPr | (NMR) |
| 152 | H | $CF_3$ | H | H | —N=N— | OEt | (NMR) |
| 153 | H | OMe | H | H | —N=N— | nBu | (NMR) |

Additional data as to compounds of table 1:

Compound no. 40: $^1$H-NMR (300 MHz; DMSO): 9.32 ppm (s, 1H, H-1), 8.48 ppm (m, 2H, H-6 and H-9), 8.15 and 7.80 ppm (two m, each 1H, H-7 and H-8);

Compound no. 41: $^1$H-NMR (300 MHz; DMSO): 7.82 and 7.01 ppm (two dd, each 1H, H-6 and H-9), 8.64 ppm and 7.43 (two m, 1H, H-7 and H-8), 7.60 ppm (m, 5H, Ph), 4.03 ppm (s, 3H, OMe;

Compound no. 43: $^1$H-NMR (300 MHz; CDCl$_3$): 8.93 and 8.25 ppm (two dd, each 1H, H-6 and H-9), 8.18 ppm and 8.05 (two m, 1H, H-7 and H-8)

Compound no. 45: $^1$H-NMR (300 MHz; CDCl$_3$): 8.25 (d, 1H, H-6), 8.19 ppm (d, 1H, H-9), 7.72 (dd, 1H, H-8), 4.09 s, 3H, OMe);

Compound no. 73: $^1$H-NMR (300 MHz; DMSO): 9.82 (s, 1H, 1-H), 8.78 ppm (d, 1H, H-9), 8.44 ppm (d, 1H, H-6), 7.83 ppm (dd, H, H-7);

Compound no. 147: $^1$H-NMR (300 MHz; CDCl$_3$): 8.4 ppm (d, 1H, H-9), 8.11 ppm (d, 1H, H-6), 7.56 ppm (dd, 1H, H-8), 4.03 ppm (s, 3H, OMe), 3.01 (s, 3H, SMe);

Compound no. 148: $^1$H-NMR (300 MHz; DMSO): 7.73 ppm (dd, 1H, H-8), 7.59 ppm (s, 1H, NH), 7.41 ppm (d, 1H, H-9), 6.60 ppm (s, 1H, H-6), 6.58 (s, 1H, NH), 3.74 (s, 3H, OMe), 2.59 (s, 3H, Me)

Compound no. 149: $^1$H-NMR (300 MHz; DMSO): 8.75 and 8.39 ppm (two dd, each 1H, H-6 and H-9), 8.14 ppm and 7.93 (two m, 1H, H-7 and H-8), 4.34 ppm (t, 2H, CH$_2$), 1.95 ppm (tq, 2H, CH$_2$), 1.10 (t, 3H, CH$_3$)

Compound no. 150: $^1$H-NMR (300 MHz; DMSO): 8.68 ppm (d, 1H, H-9), 8.39 ppm (d, 1H, H-6), 7.95 ppm (dd, 1H, H-8), 4.08 and 3.92 ppm (two s, each 3H, OMe and SO$_2$Me)

Compound no. 151: $^1$H-NMR (300 MHz; CDCl$_3$): 8.18 ppm (d, 1H, H-6), 8.03 ppm (d, 1H, H-9), 7.59 ppm (dd, 1H, H-8), 4.08 ppm (s, 3H, OMe), 3.22 ppm (t, 2H, CH$_2$), 2.09 (t,q; 2H, CH$_2$), 1.19 ppm (t, 3H, CH$_3$)

Compound no. 152: $^1$H-NMR (300 MHz; CDCl$_3$): 8.93 ppm (d, 1H, H-6), 8.45 ppm (d, 1H, H-9), 8.13 ppm (dd, 1H, H-8), 4.98 ppm (q, 2H, CH$_2$), 1.68 (t, 3H, Me)

Compound no. 153: $^1$H-NMR (300 MHz; DMSO): 8.29 ppm (d, 1H, H-9), 8.22 ppm (d, 1H, H-6), 7.72 ppm (dd, 1H, H-8), 4.02 ppm (s, 3H, OMe), 3.44 ppm (t, 2H, CH$_2$), 1.93 ppm and 1.52 ppm (two m; each 2H, CH$_2$), 0.96 ppm (t, 3H, CH$_3$)

TABLE 2

Compounds of formula (Ik)

(Ik)

| Cpd | R¹ | R² | R³ | R⁴ | -A-W- | mp. °C. |
|---|---|---|---|---|---|---|
| 147 | H | H | H | H | —N=N— | 115-117 |
| 148 | H | H | H | H | —NH—NH— | 194 |
| 149 | H | OMe | H | H | —NH—NH— | |
| 150 | H | Me | H | H | —NH—NH— | |
| 151 | H | Me | H | H | —[N(CH$_2$OMe)]$_2$— | |
| 152 | H | Cl | H | H | —NH—NH— | |
| 153 | H | H | H | H | —[(N(CO-3-F-Ph)]$_2$— | |
| 154 | H | Cl | H | H | —N=N— | |
| 155 | H | Me | H | H | —N=N— | |
| 156 | H | OMe | H | H | —N=N— | |
| 157 | H | H | H | H | —[N(CO-4-Br-Ph)]$_2$— | |
| 158 | H | Cl | H | Cl | —N=N— | |
| 159 | H | Br | H | H | —N$^+$(O$^-$)=N— | |
| 160 | H | H | H | H | —[N(CH$_2$CH=CH$_2$)]$_2$— | |
| 161 | H | OMe | H | H | —[N(CH$_2$CH=CH$_2$)]$_2$— | |
| 162 | H | Cl | H | H | —[N(CH$_2$CH=CH$_2$)]$_2$— | |
| 163 | H | H | H | H | —[N(CH$_2$Ph)]$_2$— | |
| 164 | H | OMe | H | H | —[N(CH$_2$Ph)]$_2$— | |
| 165 | H | Cl | H | H | —[N(CH$_2$Ph)]$_2$— | |
| 166 | H | H | H | H | —[N(CH$_2$OMe)]$_2$— | |
| 167 | H | OMe | H | H | —[N(CH$_2$OMe)]$_2$— | |
| 168 | H | H | H | H | —NMe—NMe— | |
| 169 | H | OMe | H | H | —[N(COMe)]$_2$— | |
| 170 | H | H | H | H | —[N(COMe)]$_2$— | |
| 171 | H | CF$_3$ | H | H | —N=N— | |
| 172 | H | CF$_3$ | H | H | —NH—NH— | |
| 173 | H | Br | H | H | —N=N— | |
| 174 | H | Br | H | H | —NH—NH— | |
| 175 | H | H | Cl | H | —N=N— | |
| 176 | H | H | Cl | H | —NH—NH— | |
| 177 | H | H | H | H | —N$^+$(O$^-$)=N— | |
| 178 | H | H | H | H | —N$^+$(O$^-$)=N— | |

TABLE 3

Compounds of formula (IL)

(IL)

| Cpd | R¹ | R² | R³ | R⁴ | -A-W- | R⁸ | mp. °C. (Ref.) |
|---|---|---|---|---|---|---|---|
| 179 | H | H | H | H | —N=N— | H | |
| 180 | H | Me | H | H | —NH—NH— | H | |
| 181 | H | Cl | H | H | —NH—NH— | H | |
| 182 | H | Me | H | H | —N=N— | H | 230-231 (NMR) |
| | H | H | H | H | —NH—NH— | H | |
| 184 | H | Cl | H | H | —N=N— | H | |
| 185 | H | Cl | H | Cl | —N=N— | H | |

TABLE 3-continued

Compounds of formula (IL)

(IL)

| Cpd | R¹ | R² | R³ | R⁴ | -A-W- | R⁸ | mp. ° C. (Ref.) |
|---|---|---|---|---|---|---|---|
| 186 | H | Br | H | H | —N⁺(O⁻)=N— | H | |
| 187 | H | OMe | H | H | —N=N— | H | 210-211 (NMR) |
| 188 | H | OMe | H | H | —NN— | Me | |
| 189 | H | OMe | H | H | —N=N— | Et | |
| 190 | H | OMe | H | H | —N=N— | Ph | |
| 191 | H | OMe | H | H | —NH—NH— | H | |
| 192 | H | H | H | H | —N=N— | CF₃ | |
| 193 | H | H | H | H | —NH—NH— | CF₃ | |
| 194 | H | OMe | H | H | —N=N— | CF₃ | |
| 195 | H | OMe | H | H | —NH—NH— | CF₃ | |
| 196 | H | H | H | H | —N=N— | Ph | |
| 197 | H | H | H | H | —NH—NH— | Ph | |
| 198 | H | OMe | H | H | —NH—NH— | Ph | |
| 199 | H | H | H | H | —N=N— | OMe | |
| 200 | H | H | H | H | —NH—NH— | OMe | |
| 201 | H | OMe | H | H | —N=N— | OMe | |
| 202 | H | OMe | H | H | —NH—NH— | OMe | |
| 203 | H | H | H | H | —N=N— | OEt | |
| 204 | H | H | H | H | —NH—NH— | OEt | |
| 205 | H | OMe | H | H | —N=N— | OEt | |
| 206 | H | OMe | H | H | —NH—NH— | OEt | |
| 207 | H | H | H | H | —NMe-NMe- | H | |
| 208 | H | OMe | H | H | —[N(COMe)]₂— | H | |
| 209 | H | H | H | H | —[N(COMe)]₂— | H | |
| 210 | H | CF₃ | H | H | —N=N— | H | |
| 211 | H | CF₃ | H | H | —NH—NH— | H | |
| 212 | H | Br | H | H | —N=N— | H | |
| 213 | H | Br | H | H | —NH—NH— | H | |
| 214 | H | H | Cl | H | —N=N— | H | |
| 215 | H | H | Cl | H | —NH—NH— | H | |
| 216 | H | H | H | H | —N=N— | Me | |
| 217 | H | H | H | H | —NH—NH— | Me | |
| 218 | H | H | H | H | —N⁺(O⁻)=N— | Me | |
| 219 | H | Cl | H | H | —N=N— | Me | |
| 220 | H | Cl | H | H | —NH—NH— | Me | |
| 221 | H | Cl | H | H | —N⁺(O⁻)=N— | Me | |
| 222 | H | H | H | H | —N=N— | Et | |
| 223 | H | H | H | H | —NH—NH— | Et | |
| 224 | H | H | H | H | —N⁺(O⁻)=N— | Et | |
| 225 | H | Cl | H | H | —N=N— | Et | |
| 226 | H | Cl | H | H | —NH—NH— | Et | |
| 227 | H | Cl | H | H | —N⁺(O⁻)=N— | Et | |
| 228 | H | Me | H | Me | —N=N— | H | 225-227 |
| 229 | H | H | H | H | —NH—NH— | iPr | |
| 230 | H | H | H | H | —N⁺(O⁻)=N— | iPr | |
| 231 | H | Cl | H | H | —N=N— | iPr | |
| 232 | H | Cl | H | H | —NH—NH— | iPr | |
| 233 | H | Cl | H | H | —N⁺(O⁻)=N— | iPr | |
| 234 | H | H | H | H | —N=N— | SMe | |
| 235 | H | H | H | H | —NH—NH— | SMe | |
| 236 | H | H | H | H | —N⁺(O⁻)=N— | SMe | 230-232 |
| 237 | H | Cl | H | H | —N=N— | SMe | |
| 238 | H | Cl | H | H | —NH—NH— | SMe | |
| 239 | H | Cl | H | H | —N⁺(O⁻)=N— | SMe | 200-202 |
| 240 | H | H | H | H | —N=N— | Cl | |
| 241 | H | H | H | H | —NH—NH— | Cl | |
| 242 | H | H | H | H | —N⁺(O⁻)=N— | Cl | |
| 243 | H | Cl | H | H | —N=N— | Cl | |
| 244 | H | Cl | H | H | —NH—NH— | Cl | |

TABLE 3-continued

Compounds of formula (IL)

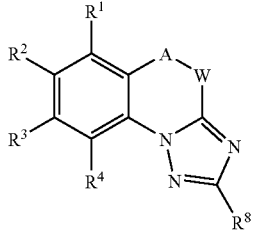

| Cpd | R¹ | R² | R³ | R⁴ | -A-W- | R⁸ | mp. °C. (Ref.) |
|---|---|---|---|---|---|---|---|
| 245 | H | Cl | H | H | —N⁺(O⁻)=N— | Cl | |
| 246 | H | H | H | H | —N=N— | NMe₂ | |
| 247 | H | H | H | H | —NH—NH— | NMe₂ | |
| 248 | H | H | H | H | —N⁺(O⁻)=N— | NMe₂ | |
| 249 | H | Cl | H | H | —N=N— | NMe₂ | |
| 250 | H | Cl | H | H | —NH—NH— | NMe₂ | |
| 251 | H | Cl | H | H | —N⁺(O⁻)=N— | NMe₂ | |
| 252 | H | H | H | H | —N=N— | CO₂Me | |
| 253 | H | H | H | H | —NH—NH— | CO₂Me | |
| 254 | H | H | H | H | —N⁺(O⁻)=N— | CO₂Me | |
| 255 | H | Cl | H | H | —N=N— | CO₂Me | |
| 256 | H | Cl | H | H | —NH—NH— | CO₂Me | |
| 257 | H | Cl | H | H | —N⁺(O⁻)=N— | CO₂Me | |
| 258 | H | H | H | H | —N=N— | COMe | |
| 259 | H | H | H | H | —NH—NH— | COMe | |
| 260 | H | H | H | H | —N⁺(O⁻)=N— | COMe | |
| 261 | H | Cl | H | H | —N=N— | COMe | |
| 262 | H | Cl | H | H | —NH—NH— | COMe | |
| 263 | H | Cl | H | H | —N⁺(O⁻)=N— | COMe | |
| 264 | H | H | H | H | —N=N— | CONMe₂ | |
| 265 | H | H | H | H | —NH—NH— | CONMe₂ | |
| 266 | H | H | H | H | —N⁺(O⁻)=N— | CONMe₂ | |
| 267 | H | Cl | H | H | —N=N— | CONMe₂ | |
| 268 | H | Cl | H | H | —NH—NH— | CONMe₂ | |
| 269 | H | Cl | H | H | —N⁺(O⁻)=N— | CONMe₂ | |
| 270 | H | H | H | H | —N=N— | CH₂Ph | |
| 271 | H | H | H | H | —NH—NH— | CH₂Ph | |
| 272 | H | H | H | H | —N⁺(O⁻)=N— | CH₂Ph | |
| 273 | H | Cl | H | H | —N=N— | CH₂Ph | |
| 274 | H | Cl | H | H | —NH—NH— | CH₂Ph | |
| 275 | H | Cl | H | H | —N⁺(O⁻)=N— | CH₂Ph | |
| 276 | H | H | H | H | —N=N— | CN | |
| 277 | H | H | H | H | —NH—NH— | CN | |
| 278 | H | H | H | H | —N⁺(O⁻)=N— | CN | |
| 279 | H | Cl | H | H | —N=N— | CN | |
| 280 | H | Cl | H | H | —NH—NH— | CN | |
| 281 | H | Cl | H | H | —N⁺(O⁻)=N— | CN | |
| 282 | H | H | H | H | —N=N— | NO₂ | |
| 283 | H | H | H | H | —NH—NH— | NO₂ | |
| 284 | H | H | H | H | —N⁺(O⁻)=N— | NO₂ | |
| 285 | H | Cl | H | H | —N=N— | NO₂ | |
| 286 | H | Cl | H | H | —NH—NH— | NO₂ | |
| 287 | H | Cl | H | H | —N⁺(O⁻)=N— | NO₂ | |
| 288 | H | CF₃ | H | H | —N=N— | H | (NMR) |
| 289 | H | PPh | H | H | —N=N— | H | (NMR) |
| 290 | H | OCF₃ | H | H | —N=N— | H | (NMR) |
| 291 | H | OMe | OMe | H | —N=N— | H | (NMR) |
| 292 | H | OEt | H | H | —N=N— | H | (NMR) |

Additional data as to compouds of table 3:

Compound no. 182: $^1$H-NMR (300 MHz; DMSO): 8.68 ppm (s,1H, H-2), 8.59 ppm (d, 1H, H-6), 8.39 ppm (d, 1H, H-9), 7.93 (dd,1H, H-8), 2.72 ppm (s, 3H, Me)

Compound no. 187: $^1$H-NMR (300 MHz; DMSO): 8.64 ppm (s, 1H, H-2), 8.41 ppm (d, 1H, H-9), 8.17 ppm (d, $_1$H, H-6), 7.77 (dd, 1H, H-8), 4.06 ppm (s, 3H, OMe)

Compound no. 288: $^1$H-NMR (300 MHz; CDCl$_3$): 9.18 ppm (bs, 1H, H-6), 8.79 ppm (s, 1H, H-2), 8.69 ppm (d, 1H, H-9), 8.37(dd, 1H, H-8)

Compound no 289: $^1$H-NMR (300 MHz; CDCl$_3$): 8.65 ppm (s, 1H, H-2), 8.51 ppm (d, 1H, H-9), 8.16 ppm (d, 1H, H-6), 7.88(dd, 1H, H-8), 7.49 (m, 2H, H-3',5'), 7.39 (m, 1H, H-4'), 7.18 (m, 2H, H-2',6')

Compound no. 290: $^1$H-NMR (300 MHz; CDCl$_3$): 8.74 ppm (s, 1H, H-2), 8.71 ppm (bs, 1H, H-6), 8.64 ppm (d, 1H, H-9), 8.04(dd, 1H, H-8)

Compound no 291: $^1$H-NMR (300 MHz; CDCl$_3$): 8.41 ppm (s, 1H, H-2), 8.21 ppm (s, 1H, H-6), 7.83 ppm (s, 1H, H-9), 4.21 and 4.15 (two s, each 3H, 2×OMe)

Compound no. 292: $^1$H-NMR (300 MHz; CDCl$_3$): 8.64 ppm (s, 1H, H-2), 8.41 ppm (d, 1H, H-9), 8.11 ppm (d, 1H, H-6), 7.74 (dd, 1H, H-8), 4.31 ppm (q, 2H, CH$_2$), 2.58 (t, 3H, Me)

TABLE 4

Compounds of formula (Im)

(Im)

| Cpd | R$^1$ | R$^2$ | R$^3$ | R$^4$ | -A-W- | R$^8$ | R$^9$ | mp. °C. (Ref.) |
|---|---|---|---|---|---|---|---|---|
| 288 | H | H | H | H | —N=N— | H | H | 189-190 |
| 289 | H | Me | H | H | —NH—NH— | H | H | |
| 290 | H | Cl | H | H | —NH—NH— | H | H | |
| 291 | H | Me | H | H | —NN— | H | H | 169-171 (NMR) |
| 292 | H | H | H | H | —NH—NH— | H | H | |
| 293 | H | Cl | H | H | —N=N— | H | H | 155-156 |
| 294 | H | Cl | H | Cl | —N=N— | H | H | |
| 295 | H | Br | H | H | —N$^+$(O$^-$)=N— | H | H | |
| 296 | H | OMe | H | H | —N=N— | H | H | 167-169 (NMR) |
| 297 | H | OMe | H | H | —N=N— | Me | H | |
| 298 | H | OMe | H | H | —N=N— | Et | H | |
| 299 | H | OMe | H | H | —N=N— | Ph | H | |
| 300 | H | OMe | H | H | —NH—NH— | H | H | |
| 301 | H | H | H | H | —N=N— | CF$_3$ | H | |
| 302 | H | H | H | H | —NH—NH— | CF$_3$ | H | |
| 303 | H | OMe | H | H | —N=N— | CF$_3$ | H | |
| 304 | H | OMe | H | H | —NH—NH— | CF$_3$ | H | |
| 305 | H | H | H | H | —N=N— | Ph | H | |
| 306 | H | H | H | H | —NH—NH— | Ph | H | |
| 307 | H | OMe | H | H | —NH—NH— | Ph | H | |
| 308 | H | H | H | H | —N=N— | OMe | H | |
| 309 | H | H | H | H | —NH—NH— | OMe | H | |
| 310 | H | OMe | H | H | —N=N— | OMe | H | |
| 311 | H | OMe | H | H | —NH—NH— | OMe | H | |
| 312 | H | H | H | H | —N=N— | OEt | H | |
| 313 | H | H | H | H | —NH—NH— | OEt | H | |
| 314 | H | OMe | H | H | —N=N— | OEt | H | |
| 315 | H | OMe | H | H | —NH—NH— | OEt | H | |
| 316 | H | H | H | H | —NMe-NMe— | H | H | |
| 317 | H | OMe | H | H | —[N(COMe)]$_2$— | H | H | |
| 318 | H | H | H | H | —[N(COMe)]$_2$— | H | H | |
| 319 | H | CF$_3$ | H | H | —N=N— | H | H | |
| 320 | H | CF$_3$ | H | H | —NH—NH— | H | H | |
| 321 | H | Br | H | H | —N=N— | H | H | |
| 322 | H | Br | H | H | —NH—NH— | H | H | |
| 323 | H | H | Cl | H | —N=N— | H | H | |
| 324 | H | H | Cl | H | —NH—NH— | H | H | |
| 325 | H | H | H | H | —N=N— | Me | H | |
| 326 | H | H | H | H | —NH—NH— | Me | H | |
| 327 | H | H | H | H | —N$^+$(O$^-$)=N— | H | H | 148 |

TABLE 4-continued

Compounds of formula (Im)

(Im)

| Cpd | $R^1$ | $R^2$ | $R^3$ | $R^4$ | -A-W- | $R^8$ | $R^9$ | mp. °C. (Ref.) |
|---|---|---|---|---|---|---|---|---|
| 328 | H | Cl | H | H | —N=N— | Me | H | |
| 329 | H | Cl | H | H | —NH—NH— | Me | H | |
| 330 | H | $CF_3$ | H | H | —N$^+$(O$^-$)=N— | H | H | 148 |
| 331 | H | H | H | H | —N=N— | Et | H | |
| 332 | H | H | H | H | —NH—NH— | Et | H | |
| 333 | H | H | H | H | —N$^+$(O$^-$)=N— | Et | H | |
| 334 | H | Cl | H | H | —N=N— | Et | H | |
| 335 | H | Cl | H | H | —NH—NH— | Et | H | |
| 336 | H | Cl | H | H | —N$^+$(O$^-$)=N— | Et | H | |
| 337 | H | H | H | H | —N=N— | iPr | H | |
| 338 | H | H | H | H | —NH—NH— | iPr | H | |
| 339 | H | H | H | H | —N$^+$(O$^-$)=N— | iPr | H | |
| 340 | H | Cl | H | H | —N=N— | iPr | H | |
| 341 | H | Cl | H | H | —NH—NH— | iPr | H | |
| 342 | H | Cl | H | H | —N$^+$(O$^-$)=N— | iPr | H | |
| 343 | H | H | H | H | —N=N— | SMe | H | |
| 344 | H | H | H | H | —NH—NH— | SMe | H | |
| 345 | H | H | H | H | —N$^+$(O$^-$)=N— | SMe | H | |
| 346 | H | Cl | H | H | —N=N— | SMe | H | |
| 347 | H | Cl | H | H | —NH—NH— | SMe | H | |
| 348 | H | Cl | H | H | —N$^+$(O$^-$)=N— | SMe | H | |
| 349 | H | H | H | H | —N=N— | Cl | H | |
| 350 | H | H | H | H | —NH—NH— | Cl | H | |
| 351 | H | H | H | H | —N$^+$(O$^-$)=N— | Cl | H | |
| 352 | H | Cl | H | H | —N=N— | Cl | H | |
| 353 | H | Cl | H | H | —NH—NH— | Cl | H | |
| 354 | H | Cl | H | H | —N$^+$(O$^-$)=N— | Cl | H | |
| 355 | H | H | H | H | —N=N— | $NMe_2$ | H | |
| 356 | H | H | H | H | —NH—NH— | $NMe_2$ | H | |
| 357 | H | H | H | H | —N$^+$(O$^-$)=N— | $NMe_2$ | H | |
| 358 | H | Cl | H | H | —N=N— | $NMe_2$ | H | |
| 359 | H | Cl | H | H | —NH—NH— | $NMe_2$ | H | |
| 360 | H | Cl | H | H | —N$^+$(O$^-$)=N— | $NMe_2$ | H | |
| 361 | H | H | H | H | —N=N— | $CO_2Me$ | OH | |
| 362 | H | H | H | H | —NH—NH— | $CO_2Me$ | H | |
| 363 | H | H | H | H | —N$^+$(O$^-$)N— | $CO_2Me$ | H | |
| 364 | H | Cl | H | H | —N=N— | $CO_2Me$ | OH | |
| 365 | H | Cl | H | H | —NH—NH— | $CO_2Me$ | H | |
| 366 | H | Cl | H | H | —N$^+$(O$^-$)=N— | $CO_2Me$ | H | |
| 367 | H | H | H | H | —N=N— | COMe | H | |
| 368 | H | H | H | H | —NH—NH— | COMe | H | |
| 369 | H | H | H | H | —N$^+$(O$^-$)=N— | COMe | H | |
| 370 | H | Cl | H | H | —N=N— | COMe | H | |
| 371 | H | Cl | H | H | —NH—NH— | COMe | H | |
| 372 | H | Cl | H | H | —N$^+$(O$^-$)=N— | COMe | H | |
| 373 | H | H | H | H | —N=N— | $CONMe_2$ | H | |
| 374 | H | H | H | H | —NH—NH— | $CONMe_2$ | H | |
| 375 | H | H | H | H | —N$^+$(O$^-$)=N— | $CONMe_2$ | H | |
| 376 | H | Cl | H | H | —N=N— | $CONMe_2$ | H | |
| 377 | H | Cl | H | H | —NH—NH— | $CONMe_2$ | H | |
| 378 | H | Cl | H | H | —N$^+$(O$^-$)=N— | $CONMe_2$ | H | |
| 379 | H | H | H | H | —N=N— | $CH_2Ph$ | H | |
| 380 | H | H | H | H | —NH—NH— | $CH_2Ph$ | H | |
| 381 | H | H | H | H | —N$^+$(O$^-$)=N— | $CH_2Ph$ | H | |
| 382 | H | Cl | H | H | —N=N— | $CH_2Ph$ | H | |
| 383 | H | Cl | H | H | —NH—NH— | $CH_2Ph$ | H | |
| 384 | H | Cl | H | H | —N$^+$(O$^-$)=N— | $CH_2Ph$ | H | |
| 385 | H | H | H | H | —N=N— | CN | H | |
| 386 | H | H | H | H | —NH—NH— | CN | H | |
| 387 | H | H | H | H | —N$^+$(O$^-$)=N— | CN | H | |

TABLE 4-continued

Compounds of formula (Im)

(Im)

| Cpd | R¹ | R² | R³ | R⁴ | -A-W- | R⁸ | R⁹ | mp. °C. (Ref.) |
|---|---|---|---|---|---|---|---|---|
| 388 | H | Cl | H | H | —N=N— | CN | H | |
| 389 | H | Cl | H | H | —NH—NH— | CN | H | |
| 390 | H | Cl | H | H | —N⁺(O⁻)=N— | CN | H | |
| 391 | H | H | H | H | —N=N— | NO₂ | H | |
| 392 | H | H | H | H | —NH—NH— | NO₂ | H | |
| 393 | H | H | H | H | —N⁺(O⁻)=N— | NO₂ | H | |
| 394 | H | Cl | H | H | —N=N— | NO₂ | H | |
| 395 | H | Cl | H | H | —NH—NH— | NO₂ | H | |
| 396 | H | Cl | H | H | —N⁺(O⁻)=N— | NO₂ | H | |
| 397 | H | OMe | H | H | —N=N— | H | Me | |
| 398 | H | OMe | H | H | —N=N— | H | Et | |
| 399 | H | OMe | H | H | —N=N— | H | Ph | |
| 400 | H | H | H | H | —N⁺N— | H | CF₃ | |
| 401 | H | H | H | H | —NH—NH— | H | CF₃ | |
| 402 | H | OMe | H | H | —N=N— | H | CF₃ | |
| 403 | H | OMe | H | H | —NH—NH— | H | CF₃ | |
| 404 | H | H | H | H | —N=N— | H | Ph | |
| 405 | H | H | H | H | —NH—NH— | H | Ph | |
| 406 | H | H | H | H | —N⁺(O⁻)=N— | H | Ph | |
| 407 | H | H | H | H | —N=N— | H | OMe | |
| 408 | H | H | H | H | —NH—NH— | H | OMe | |
| 409 | H | OMe | H | H | —N=N— | H | OMe | |
| 410 | H | OMe | H | H | —NH—NH— | H | OMe | |
| 411 | H | H | H | H | —N=N— | H | OEt | |
| 412 | H | H | H | H | —NH—NH— | H | OEt | |
| 413 | H | OMe | H | H | —N=N— | H | OEt | |
| 414 | H | OMe | H | H | —NH—NH— | H | OEt | |
| 415 | H | H | H | H | —N=N— | H | Me | |
| 416 | H | H | H | H | —NH—NH— | H | Me | |
| 417 | H | H | H | H | —N⁺(O⁻)=N— | H | Me | |
| 418 | H | Cl | H | H | —N=N— | H | Me | |
| 419 | H | Cl | H | H | —NH—NH— | H | Me | |
| 420 | H | Cl | H | H | —N⁺(O⁻)=N— | H | Me | |
| 421 | H | H | H | H | —N=N— | H | Et | |
| 422 | H | H | H | H | —NH—NH— | H | Et | |
| 423 | H | H | H | H | —N⁺(O⁻)=N— | H | Et | |
| 424 | H | Cl | H | H | —N=N— | H | Et | |
| 425 | H | Cl | H | H | —NH—NH— | H | Et | |
| 426 | H | Cl | H | H | —N⁺(O⁻)=N— | H | Et | |
| 427 | H | H | H | H | —N=N— | H | iPr | |
| 428 | H | H | H | H | —NH—NH— | H | iPr | |
| 429 | H | H | H | H | —N⁺(O⁻)=N— | H | iPr | |
| 430 | H | Cl | H | H | —N=N— | H | iPr | |
| 431 | H | Cl | H | H | —NH—NH— | H | iPr | |
| 432 | H | Cl | H | H | —N⁺(O⁻)=N— | H | iPr | |
| 433 | H | H | H | H | —N=N— | H | SMe | |
| 434 | H | H | H | H | —NH—NH— | H | SMe | |
| 435 | H | H | H | H | —N⁺(O⁻)=N— | H | SMe | |
| 436 | H | Cl | H | H | —N=N— | H | SMe | |
| 437 | H | Cl | H | H | —NH—NH— | H | SMe | |
| 438 | H | Cl | H | H | —N⁺(O⁻)=N— | H | SMe | |
| 439 | H | H | H | H | —N=N— | H | Cl | |
| 440 | H | H | H | H | —NH—NH— | H | Cl | |
| 441 | H | H | H | H | —N⁺(O⁻)=N— | H | Cl | |
| 442 | H | Cl | H | H | —N=N— | H | Cl | |
| 443 | H | Cl | H | H | —NH—NH— | H | Cl | |
| 444 | H | Cl | H | H | —N⁺(O⁻)=N— | H | Cl | |
| 445 | H | H | H | H | —N=N— | H | NMe₂ | |
| 446 | H | H | H | H | —NH—NH— | H | NMe₂ | |
| 447 | H | H | H | H | —N⁺(O⁻)=N— | H | NMe₂ | |

TABLE 4-continued

Compounds of formula (Im)

(Im)

| Cpd | R¹ | R² | R³ | R⁴ | -A-W- | R⁸ | R⁹ | mp. °C. (Ref.) |
|---|---|---|---|---|---|---|---|---|
| 448 | H | Cl | H | H | —N=N— | H | $NMe_2$ | |
| 449 | H | Cl | H | H | —NH—NH— | H | $NMe_2$ | |
| 450 | H | Cl | H | H | —N⁺(O⁻)=N— | H | $NMe_2$ | |
| 451 | H | H | H | H | —N=N— | H | $CO_2Me$ | |
| 452 | H | H | H | H | —NH—NH— | H | $CO_2Me$ | |
| 453 | H | H | H | H | —N⁺(O⁻)=N— | H | $CO_2Me$ | |
| 454 | H | Cl | H | H | —N=N— | H | $CO_2Me$ | |
| 455 | H | Cl | H | H | —NH—NH— | H | $CO_2Me$ | |
| 456 | H | Cl | H | H | —N⁺(O⁻)=N— | H | $CO_2Me$ | |
| 457 | H | H | H | H | —N=N— | H | COMe | |
| 458 | H | H | H | H | —NH—NH— | H | COMe | |
| 459 | H | H | H | H | —N⁺(O⁻)=N— | H | COMe | |
| 460 | H | Cl | H | H | —N=N— | H | COMe | |
| 461 | H | Cl | H | H | —NH—NH— | H | COMe | |
| 462 | H | Cl | H | H | —N⁺(O⁻)=N— | H | COMe | |
| 463 | H | H | H | H | —N=N— | H | $CONMe_2$ | |
| 464 | H | H | H | H | —NH—NH— | H | $CONMe_2$ | |
| 465 | H | H | H | H | —N⁺(O⁻)=N— | H | $CONH_2$ | |
| 466 | H | Cl | H | H | —N=N— | H | $CONMe_2$ | |
| 467 | H | Cl | H | H | —NH—NH— | H | $CONMe_2$ | |
| 468 | H | Cl | H | H | —N⁺(O⁻)=N— | $CH_3$ | $CONMe_2$ | |
| 469 | H | H | H | H | —N=N— | H | $CH_2Ph$ | |
| 470 | H | H | H | H | —NH—NH— | H | $CH_2Ph$ | |
| 471 | H | H | H | H | —N⁺(O⁻)=N— | H | $CH_2Ph$ | |
| 472 | H | Cl | H | H | —N=N— | H | $CH_2Ph$ | |
| 473 | H | Cl | H | H | —NH—NH— | H | $CH_2Ph$ | |
| 474 | H | Cl | H | H | —N⁺(O⁻)=N— | H | $CH_2Ph$ | |
| 475 | H | H | H | H | —N=N— | H | CN | |
| 476 | H | H | H | H | —NH—NH— | H | CN | |
| 477 | H | H | H | H | —N⁺(O⁻)=N— | H | CN | |
| 478 | H | $CF_3$ | H | H | —N=N— | H | CN | 158 |
| 479 | H | Cl | H | H | —NH—NH— | H | CN | |
| 480 | H | Cl | H | H | —N⁺(O⁻)=N— | H | CN | |
| 481 | H | H | H | H | —N=N— | H | $NO_2$ | |
| 482 | H | H | H | H | —NH—NH— | H | $NO_2$ | |
| 483 | H | H | H | H | —N⁺(O⁻)=N— | H | $NO_2$ | |
| 484 | H | Cl | H | H | —N=N— | H | $NO_2$ | |
| 485 | H | Cl | H | H | —NH—NH— | H | $NO_2$ | |
| 486 | H | Cl | H | H | —N⁺(O⁻)=N— | H | $NO_2$ | |
| 487 | Me | H | Me | H | —N=N— | H | $CO_2H$ | 290 |
| 488 | Me | H | Me | H | —N=N— | H | $CO_2Et$ | 128 |
| 489 | Me | H | Me | H | —N=N— | H | $SCH_2Ph$ | |
| 490 | H | H | H | H | —N=N— | Me | Me | |
| 491 | H | H | H | H | —NH—NH— | Me | Me | |
| 492 | H | H | H | H | —N⁺(O⁻)N— | Me | Me | |
| 493 | H | Me | H | H | —N=N— | H | Br | (NMR) |

Additional data as to compounds of table 4:

Compound no. 291: $^1$H-NMR (300 MHz; CDCl$_3$): 8.40 ppm (d, 1H, H-6), 8.34 (d, 1H, H-9) 8.19 and 7.39 ppm (two d, each 1H, H-2 and H-3), 7.75 ppm (dd, 1H, H-8), 2.61 (s, 3H, Me)

Compound no. 296: $^1$H-NMR (300 MHz; CDCl$_3$): 8.41 ppm (d, 1H, H-9), 8.19 and 8.00 ppm (two d, each 1H, H-2 and H-3), 7.59 ppm (dd, 1H, H-8), 7.40 (d, 1H, H-6), 4.03 (s, 3H, OMe)

Compound no. 493: $^1$H-NMR (300 MHz; CDCl$_3$): 8.43 ppm (d, 1H, H-6), 8.30 ppm (d, 1H, H-9), 8.15 ppm (s, 1H, H-2), 7.78 ppm (dd, 1H, H-8), 2.64 (s, 3H, Me)

TABLE 5

Compounds of formula (In)

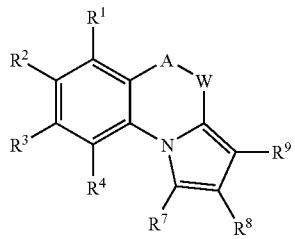

(In)

| Cpd | R$^1$ | R$^2$ | R$^3$ | R$^4$ | -A-W- | R$^7$ | R$^8$ | R$^9$ | mp. ° C. |
|---|---|---|---|---|---|---|---|---|---|
| 493 | H | H | H | H | —N═N— | H | H | H | 221 |
| 494 | H | Me | H | H | —NH—NH— | H | H | H | |
| 495 | H | Cl | H | H | —NH—NH— | H | H | H | |
| 496 | H | Me | H | H | —N═N— | H | H | H | |
| 497 | H | H | H | H | —NH—NH— | H | H | H | |
| 498 | H | Cl | H | H | —N═N— | H | H | H | |
| 499 | H | Cl | H | Cl | —N═N— | H | H | H | |
| 500 | H | Br | H | H | —N$^+$(O$^-$)═N— | H | H | H | |
| 501 | H | OMe | H | H | —NN— | H | H | H | |
| 502 | H | OMe | H | H | —N═N— | Me | H | H | |
| 503 | H | OMe | H | H | —N═N— | Et | H | H | |
| 504 | H | OMe | H | H | —N═N— | Ph | H | H | |
| 505 | H | OMe | H | H | —NH—NH— | H | H | H | |
| 506 | H | H | H | H | —N═N— | CF$_3$ | H | H | |
| 507 | H | H | H | H | —NH—NH— | CF$_3$ | H | H | |
| 508 | H | OMe | H | H | —N═N— | CF$_3$ | H | H | |
| 509 | H | OMe | H | H | —NH—NH— | CF$_3$ | H | | |
| 510 | H | H | H | H | —N═N— | Ph | H | H | |
| 511 | H | H | H | H | —NH—NH— | Ph | H | H | |
| 512 | H | OMe | H | H | —NH—NH— | Ph | H | H | |
| 513 | H | H | H | H | —N═N— | OMe | H | H | |
| 514 | H | H | H | H | —NH—NH— | OMe | H | H | |
| 515 | H | OMe | H | H | —N═N— | OMe | H | H | |
| 516 | H | OMe | H | H | —NH—NH— | OMe | H | H | |
| 517 | H | H | H | H | —N═N— | OEt | H | H | |
| 518 | H | H | H | H | —NH—NH— | OEt | H | H | |
| 519 | H | OMe | H | H | —N═N— | OEt | H | H | |
| 520 | H | OMe | H | H | —NH—NH— | OEt | H | H | |
| 521 | H | H | H | H | —NMe—NMe— | H | H | H | |
| 522 | H | OMe | H | H | —[N(COMe)]$_2$— | H | H | H | |
| 523 | H | H | H | H | —[N(COMe)]$_2$— | H | H | H | |
| 524 | H | CF$_3$ | H | H | —N═N— | H | H | H | |
| 525 | H | CF$_3$ | H | H | —NH—NH— | H | H | H | |
| 526 | H | Br | H | H | —N═N— | H | H | H | |
| 527 | H | Br | H | H | —NH—NH— | H | H | H | |
| 528 | H | H | Cl | H | —N═N— | H | H | H | |
| 529 | H | H | Cl | H | —NH—NH— | H | H | H | |
| 530 | H | H | H | H | —N═N— | Me | H | H | |
| 531 | H | H | H | H | —NH—NH— | Me | H | H | |
| 532 | H | H | H | H | —N$^+$(O$^-$)═N— | Me | H | H | |
| 533 | H | Cl | H | H | —N═N— | Me | H | H | |
| 534 | H | Cl | H | H | —NH—NH— | Me | H | H | |
| 535 | H | Cl | H | H | —N$^+$(O$^-$)═N— | Me | H | H | |
| 536 | H | H | H | H | —N═N— | Et | H | H | |
| 537 | H | H | H | H | —NH—NH— | Et | H | H | |
| 538 | H | H | H | H | —N$^+$(O$^-$)═N— | Et | H | H | |

TABLE 5-continued

Compounds of formula (In)

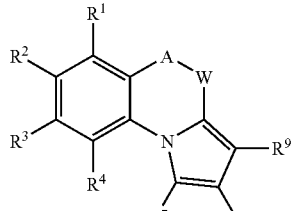

(In)

| Cpd | R¹ | R² | R³ | R⁴ | -A-W- | R⁷ | R⁸ | R⁹ | mp. °C. |
|---|---|---|---|---|---|---|---|---|---|
| 539 | H | Cl | H | H | —N=N— | Et | H | H | |
| 540 | H | Cl | H | H | —NH—NH— | Et | H | H | |
| 541 | H | Cl | H | H | —N⁺(O⁻)=N— | Et | H | H | |
| 542 | H | H | H | H | —N=N— | iPr | H | H | |
| 543 | H | H | H | H | —NH—NH— | iPr | H | H | |
| 544 | H | H | H | H | —N⁺(O⁻)=N— | iPr | H | H | |
| 545 | H | Cl | H | H | —N=N— | iPr | H | H | |
| 546 | H | Cl | H | H | —NH—NH— | iPr | H | H | |
| 547 | H | Cl | H | H | —N⁺(O⁻)=N— | iPr | H | H | |
| 548 | H | H | H | H | —N=N— | SMe | H | H | |
| 549 | H | H | H | H | —NH—NH— | SMe | H | H | |
| 550 | H | H | H | H | —N⁺(O⁻)=N— | SMe | H | H | |
| 551 | H | Cl | H | H | —N=N— | SMe | H | H | |
| 552 | H | Cl | H | H | —NH—NH— | SMe | H | H | |
| 553 | H | Cl | H | H | —N⁺(O)=N— | SMe | H | H | |
| 554 | H | H | H | H | —N=N— | Cl | H | H | |
| 555 | H | H | H | H | —NH—NH— | Cl | H | H | |
| 556 | H | H | H | H | —N⁺(O⁻)=N— | Cl | H | H | |
| 557 | H | Cl | H | H | —N=N— | Cl | H | H | |
| 558 | H | Cl | H | H | —NH—NH— | Cl | H | H | |
| 559 | H | Cl | H | H | —N⁺(O⁻)=N— | Cl | H | H | |
| 560 | H | H | H | H | —N=N— | NMe₂ | H | H | |
| 561 | H | H | H | H | —NH—NH— | NMe₂ | H | H | |
| 562 | H | H | H | H | —N⁺(O⁻)=N— | NMe₂ | H | H | |
| 563 | H | Cl | H | H | —N=N— | NMe₂ | H | H | |
| 564 | H | Cl | H | H | —NH—NH— | NMe₂ | H | H | |
| 565 | H | Cl | H | H | —N⁺(O⁻)=N— | NMe₂ | H | H | |
| 566 | H | H | H | H | —N=N— | CO₂Me | H | H | |
| 567 | H | H | H | H | —NH—NH— | CO₂Me | H | H | |
| 568 | H | H | H | H | —N⁺(O⁻)=N— | CO₂Me | H | H | |
| 569 | H | Cl | H | H | —N=N— | CO₂Me | H | H | |
| 570 | H | Cl | H | H | —NH—NH— | CO₂Me | H | H | |
| 571 | H | Cl | H | H | —N⁺(O⁻)=N— | CO₂Me | H | H | |
| 572 | H | H | H | H | —N=N— | COMe | H | H | |
| 573 | H | H | H | H | —NH—NH— | COMe | H | H | |
| 574 | H | H | H | H | —N⁺(O⁻)=N— | COMe | H | H | |
| 575 | H | Cl | H | H | —N=N— | COMe | H | H | |
| 576 | H | Cl | H | H | —NH—NH— | COMe | H | H | |
| 577 | H | Cl | H | H | —N(O⁻)=N— | COMe | H | H | |
| 578 | H | H | H | H | —N=N— | CONMe₂ | H | H | |
| 579 | H | H | H | H | —NH—NH— | CONMe₂ | H | H | |
| 580 | H | H | H | H | —N⁺(O⁻)=N— | CONMe₂ | H | H | |
| 581 | H | Cl | H | H | —N=N— | CONMe₂ | H | H | |
| 582 | H | Cl | H | H | —NH—NH— | CONMe₂ | H | H | |
| 583 | H | Cl | H | H | —N⁺(O⁻)=N— | CONMe₂ | H | H | |
| 584 | H | H | H | H | —N=N— | CH₂Ph | H | H | |
| 585 | H | H | H | H | —NH—NH— | CH₂Ph | H | H | |
| 586 | H | H | H | H | —N⁺(O⁻)=N— | CH₂Ph | H | H | |
| 587 | H | Cl | H | H | —N=N— | CH₂Ph | H | H | |
| 588 | H | Cl | H | H | —NH—NH— | CH₂Ph | H | H | |
| 589 | H | Cl | H | H | —N⁺(O⁻)=N— | CH₂Ph | H | H | |
| 590 | H | H | H | H | —N=N— | CN | H | H | |
| 591 | H | H | H | H | —NH—NH— | CN | H | H | |
| 592 | H | H | H | H | —N⁺(O⁻)=N— | CN | H | H | |
| 593 | H | Cl | H | H | —N=N— | CN | H | H | |
| 594 | H | Cl | H | H | —NH—NH— | CN | H | H | |
| 595 | H | Cl | H | H | —N⁺(O⁻)=N— | CN | H | H | |
| 596 | H | H | H | H | —N=N— | NO₂ | H | H | |
| 597 | H | H | H | H | —NH—NH— | NO₂ | H | H | |
| 598 | H | H | H | H | —N⁺(O⁻)=N— | NO₂ | H | H | |
| 599 | H | Cl | H | H | —N=N— | NO₂ | H | H | |

TABLE 5-continued

Compounds of formula (In)

$$\text{(In)}$$

| Cpd | R¹ | R² | R³ | R⁴ | -A-W- | R⁷ | R⁸ | R⁹ | mp. °C. |
|---|---|---|---|---|---|---|---|---|---|
| 600 | H | Cl | H | H | —NH—NH— | NO₂ | H | H | |
| 601 | H | Cl | H | H | —N⁺(O⁻)=N— | NO₂ | H | H | |
| 602 | H | OMe | H | H | —N=N— | H | Me | H | |
| 603 | H | OMe | H | H | —N=N— | H | Et | H | |
| 604 | H | OMe | H | H | —N=N— | H | Ph | H | |
| 605 | H | H | H | H | —N=N— | H | CF₃ | H | |
| 606 | H | H | H | H | —NH—NH— | H | CF₃ | H | |
| 607 | H | OMe | H | H | —N=N— | H | CF₃ | H | |
| 608 | H | OMe | H | H | —NH—NH— | H | CF₃ | H | |
| 609 | H | H | H | H | —N=N— | H | Ph | H | |
| 610 | H | H | H | H | —NH—NH— | H | Ph | H | |
| 611 | H | OMe | H | H | —NH—NH— | H | Ph | H | |
| 612 | H | H | H | H | —N=N— | H | OMe | H | |
| 613 | H | H | H | H | —NH—NH— | H | OMe | H | |
| 614 | H | OMe | H | H | —N=N— | H | OMe | H | |
| 615 | H | OMe | H | H | —NH—NH— | H | OMe | H | |
| 616 | H | H | H | H | —N=N— | H | OEt | H | |
| 617 | H | H | H | H | —NH—NH— | H | OEt | H | |
| 618 | H | OMe | H | H | —N=N— | H | OEt | H | |
| 619 | H | OMe | H | H | —NH—NH— | H | OEt | H | |
| 620 | H | OMe | H | H | —N=N— | H | Me | H | |
| 621 | H | OMe | H | H | —N=N— | H | Et | H | |
| 622 | H | OMe | H | H | —N=N— | H | Ph | H | |
| 623 | H | H | H | H | —N=N— | H | CF₃ | H | |
| 624 | H | H | H | H | —NH—NH— | H | CF₃ | H | |
| 625 | H | OMe | H | H | —N=N— | H | CF₃ | H | |
| 626 | H | OMe | H | H | —NH—NH— | H | CF₃ | H | |
| 627 | H | H | H | H | —N=N— | H | Ph | H | |
| 628 | H | H | H | H | —NH—NH— | H | Ph | H | |
| 629 | H | OMe | H | H | —NH—NH— | H | Ph | H | |
| 630 | H | H | H | H | —N=N— | H | OMe | H | |
| 631 | H | H | H | H | —NH—NH— | H | OMe | H | |
| 632 | H | OMe | H | H | —N=N— | H | OMe | H | |
| 633 | H | OMe | H | H | —NH—NH— | H | OMe | H | |
| 634 | H | H | H | H | —N=N— | H | OEt | H | |
| 635 | H | H | H | H | —NH—NH— | H | OEt | H | |
| 636 | H | OMe | H | H | —N=N— | H | OEt | H | |
| 637 | H | OMe | H | H | —NH—NH— | H | OEt | H | |
| 638 | H | H | H | H | —N=N— | H | Me | H | |
| 639 | H | H | H | H | —NH—NH— | H | Me | H | |
| 640 | H | H | H | H | —N⁺(O⁻)=N— | H | Me | H | |
| 641 | H | Cl | H | H | —N=N— | H | Me | H | |
| 642 | H | Cl | H | H | —NH—NH— | H | Me | H | |
| 643 | H | Cl | H | H | —N⁺(O⁻)=N— | H | Me | H | |
| 644 | H | H | H | H | —N=N— | H | Et | H | |
| 645 | H | H | H | H | —NH—NH— | H | Et | H | |
| 646 | H | H | H | H | —N⁺(O⁻)=N— | H | Et | H | |
| 647 | H | Cl | H | H | —N=N— | H | Et | H | |
| 648 | H | Cl | H | H | —NH—NH— | H | Et | H | |
| 649 | H | Cl | H | H | —N⁺(O⁻)=N— | H | Et | H | |
| 650 | H | H | H | H | —N=N— | H | iPr | H | |
| 651 | H | H | H | H | —NH—NH— | H | iPr | H | |
| 652 | H | H | H | H | —N⁺(O⁻)=N— | H | iPr | H | |
| 653 | H | Cl | H | H | —N=N— | H | iPr | H | |
| 654 | H | Cl | H | H | —NH—NH— | H | iPr | H | |
| 655 | H | Cl | H | H | —N⁺(O⁻)=N— | H | iPr | H | |
| 656 | H | H | H | H | —N=N— | H | SMe | H | |
| 657 | H | H | H | H | —NH—NH— | H | SMe | H | |
| 658 | H | H | H | H | —N⁺(O⁻)=N— | H | SMe | H | |
| 659 | H | Cl | H | H | —N=N— | H | SMe | H | |
| 660 | H | Cl | H | H | —NH—NH— | H | SMe | H | |

TABLE 5-continued

Compounds of formula (In)

(In)

| Cpd | R¹ | R² | R³ | R⁴ | -A-W- | R⁷ | R⁸ | R⁹ | mp. ° C. |
|---|---|---|---|---|---|---|---|---|---|
| 661 | H | Cl | H | H | —N⁺(O⁻)=N— | H | SMe | H | |
| 662 | H | H | H | H | —N=N— | H | Cl | H | |
| 663 | H | H | H | H | —NH—NH— | H | Cl | H | |
| 664 | H | H | H | H | —N⁺(O⁻)=N— | H | Cl | H | |
| 665 | H | Cl | H | H | —N=N— | H | Cl | H | |
| 666 | H | Cl | H | H | —NH—NH— | H | Cl | H | |
| 667 | H | Cl | H | H | —N⁺(O⁻)=N— | H | Cl | H | |
| 668 | H | H | H | H | —N=N— | H | NMe₂ | H | |
| 669 | H | H | H | H | —NH—NH— | H | NMe₂ | H | |
| 670 | H | H | H | H | —N⁺(O⁻)=N— | H | NMe₂ | H | |
| 671 | H | Cl | H | H | —N=N— | H | NMe₂ | H | |
| 672 | H | Cl | H | H | —NH—NH— | H | NMe₂ | H | |
| 673 | H | Cl | H | H | —N⁺(O⁻)=N— | H | NMe₂ | H | |
| 674 | H | H | H | H | —N=N— | H | CO₂Me | H | |
| 675 | H | H | H | H | —NH—NH— | H | CO₂Me | H | |
| 676 | H | H | H | H | —N⁺(O⁻)=N— | H | CO₂Me | H | |
| 677 | H | Cl | H | H | —N=N— | H | CO₂Me | H | |
| 678 | H | Cl | H | H | —NH—NH— | H | CO₂Me | H | |
| 679 | H | Cl | H | H | —N⁺(O⁻)=N— | H | CO₂Me | H | |
| 680 | H | H | H | H | —N=N— | H | COMe | H | |
| 681 | H | H | H | H | —NH—NH— | H | COMe | H | |
| 682 | H | H | H | H | —N⁺(O⁻)=N— | H | COMe | H | |
| 683 | H | Cl | H | H | —N=N— | H | COMe | H | |
| 684 | H | Cl | H | H | —NH—NH— | H | COMe | H | |
| 685 | H | Cl | H | H | —N⁺(O⁻)=N— | H | COMe | H | |
| 686 | H | H | H | H | —N=N— | H | CONMe₂ | H | |
| 687 | H | H | H | H | —NH—NH— | H | CONMe₂ | H | |
| 688 | H | H | H | H | —N⁺(O⁻)=N— | H | CONMe₂ | H | |
| 689 | H | Cl | H | H | —N=N— | H | CONMe₂ | H | |
| 690 | H | Cl | H | H | —NH—NH— | H | CONMe₂ | H | |
| 691 | H | Cl | H | H | —N⁺(O⁻)=N— | H | CONMe₂ | H | |
| 692 | H | H | H | H | —N=N— | H | CH₂Ph | H | |
| 693 | H | H | H | H | —NH—NH— | H | CH₂Ph | H | |
| 694 | H | H | H | H | —N⁺(O⁻)=N— | H | CH₂Ph | H | |
| 695 | H | Cl | H | H | —N=N— | H | CH₂Ph | H | |
| 696 | H | Cl | H | H | —NH—NH— | H | CH₂Ph | H | |
| 697 | H | Cl | H | H | —N⁺(O⁻)=N— | H | CH₂Ph | H | |
| 698 | H | H | H | H | —N=N— | H | CN | H | |
| 699 | H | H | H | H | —NH—NH— | H | CN | H | |
| 700 | H | H | H | H | —N⁺(O⁻)=N— | H | CN | H | |
| 701 | H | Cl | H | H | —N=N— | H | CN | H | |
| 702 | H | Cl | H | H | —NH—NH— | H | CN | H | |
| 703 | H | Cl | H | H | —N⁺(O⁻)=N— | H | CN | H | |
| 704 | H | H | H | H | —N=N— | H | NO₂ | H | |
| 705 | H | H | H | H | —NH—NH— | H | NO₂ | H | |
| 706 | H | H | H | H | —N⁺(O⁻)=N— | H | NO₂ | H | |
| 707 | H | Cl | H | H | —N=N— | H | NO₂ | H | |
| 708 | H | Cl | H | H | —NH—NH— | H | NO₂ | H | |
| 709 | H | Cl | H | H | —N⁺(O⁻)=N— | H | NO₂ | H | |
| 710 | H | OMe | H | H | —N=N— | H | H | Me | |
| 711 | H | OMe | H | H | —N=N— | H | H | Et | |
| 712 | H | OMe | H | H | —N=N— | H | H | Ph | |
| 713 | H | H | H | H | —N=N— | H | H | CF₃ | |
| 714 | H | H | H | H | —NH—NH— | H | H | CF₃ | |
| 715 | H | OMe | H | H | —N=N— | H | H | CF₃ | |
| 716 | H | OMe | H | H | —NH—NH— | H | H | CF₃ | |
| 717 | H | H | H | H | —N=N— | H | H | Ph | |
| 718 | H | H | H | H | —NH—NH— | H | H | Ph | |
| 719 | H | OMe | H | H | —NH—NH— | H | H | Ph | |
| 720 | H | H | H | H | —N=N— | H | H | OMe | |
| 721 | H | H | H | H | —NH—NH— | H | H | OMe | |

TABLE 5-continued

Compounds of formula (In)

$$\text{(In)}$$

| Cpd | R¹ | R² | R³ | R⁴ | -A-W- | R⁷ | R⁸ | R⁹ | mp. ° C. |
|---|---|---|---|---|---|---|---|---|---|
| 722 | H | OMe | H | H | —N=N— | H | H | OMe | |
| 723 | H | OMe | H | H | —NH—NH— | H | H | OMe | |
| 724 | H | H | H | H | —N=N— | H | H | OEt | |
| 725 | H | H | H | H | —NH—NH— | H | H | OEt | |
| 726 | H | OMe | H | H | —N=N— | H | H | OEt | |
| 727 | H | OMe | H | H | —NH—NH— | H | H | OEt | |
| 728 | H | H | H | H | —N=N— | H | H | Me | |
| 729 | H | H | H | H | —NH—NH— | H | H | Me | |
| 730 | H | H | H | H | —N⁺(O⁻)=N— | H | H | Me | |
| 731 | H | Cl | H | H | —N=N— | H | H | Me | |
| 732 | H | Cl | H | H | —NH—NH— | H | H | Me | |
| 733 | H | Cl | H | H | —N⁺(O⁻)=N— | H | H | Me | |
| 734 | H | H | H | H | —N=N— | H | H | Et | |
| 735 | H | H | H | H | —NH—NH— | H | H | Et | |
| 736 | H | H | H | H | —N⁺(O⁻)=N— | H | H | Et | |
| 737 | H | Cl | H | H | —N=N— | H | H | Et | |
| 738 | H | Cl | H | H | —NH—NH— | H | H | Et | |
| 739 | H | Cl | H | H | —N⁺(O⁻)=N— | H | H | Et | |
| 740 | H | H | H | H | —N=N— | H | H | iPr | |
| 741 | H | H | H | H | —NH—NH— | H | H | iPr | |
| 742 | H | H | H | H | —N⁺(O⁻)=N— | H | H | iPr | |
| 743 | H | Cl | H | H | —N=N— | H | H | iPr | |
| 744 | H | Cl | H | H | —NH—NH— | H | H | iPr | |
| 745 | H | Cl | H | H | —N⁺(O⁻)=N— | H | H | iPr | |
| 746 | H | H | H | H | —N=N— | H | H | SMe | |
| 747 | H | H | H | H | —NH—NH— | H | H | SMe | |
| 748 | H | H | H | H | —N⁺(O⁻)=N— | H | H | SMe | |
| 749 | H | Cl | H | H | —N=N— | H | H | SMe | |
| 750 | H | Cl | H | H | —NH—NH— | H | H | SMe | |
| 751 | H | Cl | H | H | —N⁺(O⁻)=N— | H | H | SMe | |
| 752 | H | H | H | H | —N=N— | H | H | Cl | |
| 753 | H | H | H | H | —NH—NH— | H | H | Cl | |
| 754 | H | H | H | H | —N⁺(O⁻)=N— | H | H | Cl | |
| 755 | H | Cl | H | H | —N=N— | H | H | Cl | |
| 756 | H | Cl | H | H | —NH—NH— | H | H | Cl | |
| 757 | H | Cl | H | H | —N⁺(O⁻)=N— | H | H | Cl | |
| 758 | H | H | H | H | —N=N— | H | H | NMe₂ | |
| 759 | H | H | H | H | —NH—NH— | H | H | NMe₂ | |
| 760 | H | H | H | H | —N⁺(O⁻)=N— | H | H | NMe₂ | |
| 761 | H | Cl | H | H | —N=N— | H | H | NMe₂ | |
| 762 | H | Cl | H | H | —NH—NH— | H | H | NMe₂ | |
| 763 | H | Cl | H | H | —N⁺(O⁻)=N— | H | H | NMe₂ | |
| 764 | H | H | H | H | —N=N— | H | H | CO₂Me | |
| 765 | H | H | H | H | —NH—NH— | H | H | CO₂Me | |
| 766 | H | H | H | H | —N⁺(O⁻)=N— | H | H | CO₂Me | |
| 767 | H | Cl | H | H | —N=N— | H | H | CO₂Me | |
| 768 | H | Cl | H | H | —NH—NH— | H | H | CO₂Me | |
| 769 | H | Cl | H | H | —N⁺(O⁻)=N— | H | H | CO₂Me | |
| 770 | H | H | H | H | —N=N— | H | H | COMe | |
| 771 | H | H | H | H | —NH—NH— | H | H | COMe | |
| 772 | H | H | H | H | —N⁺(O⁻)=N— | H | H | COMe | |
| 773 | H | Cl | H | H | —N=N— | H | H | COMe | |
| 774 | H | Cl | H | H | —NH—NH— | H | H | COMe | |
| 775 | H | Cl | H | H | —N⁺(O⁻)=N— | H | H | COMe | |
| 776 | H | H | H | H | —N=N— | H | H | CONMe₂ | |
| 777 | H | H | H | H | —NH—NH— | H | H | CONMe₂ | |
| 778 | H | H | H | H | —N⁺(O⁻)=N— | H | H | CONMe₂ | |
| 779 | H | Cl | H | H | —N=N— | H | H | CONMe₂ | |
| 780 | H | Cl | H | H | —NH—NH— | H | H | CONMe₂ | |
| 781 | H | Cl | H | H | —N⁺(O⁻)=N— | H | H | CONMe₂ | |
| 782 | H | H | H | H | —N=N— | H | H | CH₂Ph | |

TABLE 5-continued

Compounds of formula (In)

(In)

| Cpd | R¹ | R² | R³ | R⁴ | -A-W- | R⁷ | R⁸ | R⁹ | mp. °C. |
|---|---|---|---|---|---|---|---|---|---|
| 783 | H | H | H | H | —NH—NH— | H | H | $CH_2Ph$ | |
| 784 | H | H | H | H | —N⁺(O⁻)=N— | H | H | $CH_2Ph$ | |
| 785 | H | Cl | H | H | —N=N— | H | H | $CH_2Ph$ | |
| 786 | H | Cl | H | H | —NH—NH— | H | H | $CH_2Ph$ | |
| 787 | H | Cl | H | H | —N⁺(O⁻)=N— | H | H | $CH_2Ph$ | |
| 788 | H | H | H | H | —N=N— | H | H | CN | |
| 789 | H | H | H | H | —NH—NH— | H | H | CN | |
| 790 | H | H | H | H | —N⁺(O⁻)=N— | H | H | CN | |
| 791 | H | Cl | H | H | —N=N— | H | H | CN | |
| 792 | H | Cl | H | H | —NH—NH— | H | H | CN | |
| 793 | H | Cl | H | H | —N⁺(O⁻)=N— | H | H | CN | |
| 794 | H | H | H | H | —N=N— | H | H | $NO_2$ | |
| 795 | H | H | H | H | —NH—NH— | H | H | $NO_2$ | |
| 796 | H | H | H | H | —N⁺(O⁻)=N— | H | H | $NO_2$ | |
| 797 | H | Cl | H | H | —N=N— | H | H | $NO_2$ | |
| 798 | H | Cl | H | H | —NH—NH— | H | H | $NO_2$ | |
| 799 | H | Cl | H | H | —N⁺(O⁻)=N— | H | H | $NO_2$ | |
| 800 | H | H | H | H | —N=N— | Me | Me | Me | |
| 801 | H | H | H | H | —NH—NH— | Me | Me | Me | |
| 802 | H | H | H | H | —N⁺(O⁻)=N— | Me | Me | Me | |

TABLE 6

Compounds of formula (Io)

(Io)

| Cpd | R¹ | R² | R³ | R⁴ | —A—W— | R⁷ | R⁸ | mp. °C. |
|---|---|---|---|---|---|---|---|---|
| 803 | H | H | H | H | —N=N— | H | H | |
| 804 | H | Me | H | H | —NH—NH— | H | H | |
| 805 | H | Cl | H | H | —NH—NH— | H | H | |
| 806 | H | Me | H | H | —N=N— | H | H | |
| 807 | H | H | H | H | —NH—NH— | H | H | |
| 808 | H | Cl | H | H | —N=N— | H | H | |
| 809 | H | Cl | H | Cl | —N=N— | H | H | |
| 810 | H | Br | H | H | —N⁺(O⁻)=N— | H | H | |
| 811 | H | OMe | H | H | —N=N— | H | H | |
| 812 | H | OMe | H | H | —N=N— | Me | H | |
| 813 | H | OMe | H | H | —N=N— | Et | H | |
| 814 | H | OMe | H | H | —N=N— | Ph | H | |
| 815 | H | OMe | H | H | —NH—NH— | H | H | |
| 816 | H | H | H | H | —N=N— | $CF_3$ | H | |
| 817 | H | H | H | H | —NH—NH— | $CF_3$ | H | |
| 818 | H | OMe | H | H | —N=N— | $CF_3$ | H | |
| 819 | H | OMe | H | H | —NH—NH— | $CF_3$ | H | |
| 820 | H | H | H | H | —N=N— | Ph | H | |

TABLE 6-continued

Compounds of formula (Io)

(Io)

| Cpd | R¹ | R² | R³ | R⁴ | —A—W— | R⁷ | R⁸ | mp. °C. |
|---|---|---|---|---|---|---|---|---|
| 821 | H | H | H | H | —NH—NH— | Ph | H | |
| 822 | H | OMe | H | H | —NH—NH— | Ph | H | |
| 823 | H | H | H | H | —N=N— | OMe | H | |
| 824 | H | H | H | H | —NH—NH— | OMe | H | |
| 825 | H | OMe | H | H | —N=N— | OMe | H | |
| 826 | H | OMe | H | H | —NH—NH— | OMe | H | |
| 827 | H | H | H | H | —N=N— | OEt | H | |
| 828 | H | H | H | H | —NH—NH— | OEt | H | |
| 829 | H | OMe | H | H | —N=N— | OEt | H | |
| 830 | H | OMe | H | H | —NH—NH— | OEt | H | |
| 831 | H | H | H | H | —NMe—NMe— | H | H | |
| 832 | H | OMe | H | H | —[N(COMe)]₂— | H | H | |
| 833 | H | H | H | H | —[N(COMe)]₂— | H | H | |
| 834 | H | CF₃ | H | H | —N=N— | H | H | |
| 835 | H | CF₃ | H | H | —NH—NH— | H | H | |
| 836 | H | Br | H | H | —N=N— | H | H | |
| 837 | H | Br | H | H | —NH—NH— | H | H | |
| 838 | H | H | Cl | H | —N=N— | H | H | |
| 839 | H | H | Cl | H | —NH—NH— | H | H | |
| 840 | H | H | H | H | —N=N— | Me | H | |
| 841 | H | H | H | H | —NH—NH— | Me | H | |
| 842 | H | H | H | H | —N⁺(O⁻)=N— | Me | H | |
| 843 | H | Cl | H | H | —N=N— | Me | H | |
| 844 | H | Cl | H | H | —NH—NH— | Me | H | |
| 845 | H | Cl | H | H | —N⁺(O⁻)=N— | Me | H | |
| 846 | H | H | H | H | —N=N— | Et | H | |
| 847 | H | H | H | H | —NH—NH— | Et | H | |
| 848 | H | H | H | H | —N⁺(O⁻)=N— | Et | H | |
| 849 | H | Cl | H | H | —N=N— | Et | H | |
| 850 | H | Cl | H | H | —NH—NH— | Et | H | |
| 851 | H | Cl | H | H | —N⁺(O⁻)=N— | Et | H | |
| 852 | H | H | H | H | —N=N— | iPr | H | |
| 853 | H | H | H | H | —NH—NH— | iPr | H | |
| 854 | H | H | H | H | —N⁺(O⁻)=N— | iPr | H | |
| 855 | H | Cl | H | H | —N=N— | iPr | H | |
| 856 | H | Cl | H | H | —NH—NH— | iPr | H | |
| 857 | H | Cl | H | H | —N⁺(O⁻)=N— | iPr | H | |
| 858 | H | H | H | H | —N=N— | SMe | H | |
| 859 | H | H | H | H | —NH—NH— | SMe | H | |
| 860 | H | H | H | H | —N⁺(O⁻)=N— | SMe | H | |
| 861 | H | Cl | H | H | —N=N— | SMe | H | |
| 862 | H | Cl | H | H | —NH—NH— | SMe | H | |
| 863 | H | Cl | H | H | —N⁺(O⁻)=N— | SMe | H | |
| 864 | H | H | H | H | —N=N— | Cl | H | |
| 865 | H | H | H | H | —NH—NH— | Cl | H | |
| 866 | H | H | H | H | —N⁺(O⁻)=N— | Cl | H | |
| 867 | H | Cl | H | H | —N=N— | Cl | H | |
| 868 | H | Cl | H | H | —NH—NH— | Cl | H | |
| 869 | H | Cl | H | H | —N⁺(O⁻)=N— | Cl | H | |
| 870 | H | H | H | H | —N=N— | NMe₂ | H | |
| 871 | H | H | H | H | —NH—NH— | NMe₂ | H | |
| 872 | H | H | H | H | —N⁺(O⁻)=N— | NMe₂ | H | |
| 873 | H | Cl | H | H | —N=N— | NMe₂ | H | |
| 874 | H | Cl | H | H | —NH—NH— | NMe₂ | H | |
| 875 | H | Cl | H | H | —N⁺(O⁻)=N— | NMe₂ | H | |
| 876 | H | H | H | H | —N=N— | CO₂Me | H | |
| 877 | H | H | H | H | —NH—NH— | CO₂Me | H | |
| 878 | H | H | H | H | —N⁺(O⁻)=N— | CO₂Me | H | |
| 879 | H | Cl | H | H | —N=N— | CO₂Me | H | |
| 880 | H | Cl | H | H | —NH—NH— | CO₂Me | H | |
| 881 | H | Cl | H | H | —N⁺(O⁻)=N— | CO₂Me | H | |

TABLE 6-continued

Compounds of formula (Io)

(Io)

| Cpd | R¹ | R² | R³ | R⁴ | —A—W— | R⁷ | R⁸ | mp. ° C. |
|---|---|---|---|---|---|---|---|---|
| 882 | H | H | H | H | —N=N— | COMe | H | |
| 883 | H | H | H | H | —NH—NH— | COMe | H | |
| 884 | H | H | H | H | —N⁺(O⁻)=N— | COMe | H | |
| 885 | H | Cl | H | H | —N=N— | COMe | H | |
| 886 | H | Cl | H | H | —NH—NH— | COMe | H | |
| 887 | H | Cl | H | H | —N⁺(O⁻)=N— | COMe | H | |
| 888 | H | H | H | H | —N=N— | CONMe₂ | H | |
| 889 | H | H | H | H | —NH—NH— | CONMe₂ | H | |
| 890 | H | H | H | H | —N⁺(O⁻)=N— | CONMe₂ | H | |
| 891 | H | Cl | H | H | —N=N— | CONMe₂ | H | |
| 892 | H | Cl | H | H | —NH—NH— | CONMe₂ | H | |
| 893 | H | Cl | H | H | —N⁺(O⁻)=N— | CONMe₂ | H | |
| 894 | H | H | H | H | —N=N— | CH₂Ph | H | |
| 895 | H | H | H | H | —NH—NH— | CH₂Ph | H | |
| 896 | H | H | H | H | —N⁺(O⁻)=N— | CH₂Ph | H | |
| 897 | H | Cl | H | H | —N=N— | CH₂Ph | H | |
| 898 | H | Cl | H | H | —NH—NH— | CH₂Ph | H | |
| 899 | H | Cl | H | H | —N⁺(O⁻)=N— | CH₂Ph | H | |
| 900 | H | H | H | H | —N=N— | CN | H | |
| 901 | H | H | H | H | —NH—NH— | CN | H | |
| 902 | H | H | H | H | —N⁺(O⁻)=N— | CN | H | |
| 903 | H | Cl | H | H | —N=N— | CN | H | |
| 904 | H | Cl | H | H | —NH—NH— | CN | H | |
| 905 | H | Cl | H | H | —N⁺(O⁻)=N— | CN | H | |
| 906 | H | H | H | H | —N=N— | NO₂ | H | |
| 907 | H | H | H | H | —NH—NH— | NO₂ | H | |
| 908 | H | H | H | H | —N⁺(O⁻)=N— | NO₂ | H | |
| 909 | H | Cl | H | H | —N=N— | NO₂ | H | |
| 910 | H | Cl | H | H | —NH—NH— | NO₂ | H | |
| 911 | H | Cl | H | H | —N⁺(O⁻)=N— | NO₂ | H | |
| 912 | H | OMe | H | H | —N=N— | H | Me | |
| 913 | H | OMe | H | H | —N=N— | H | Et | |
| 914 | H | OMe | H | H | —N=N— | H | Ph | |
| 915 | H | H | H | H | —N=N— | H | CF₃ | |
| 916 | H | H | H | H | —NH—NH— | H | CF₃ | |
| 917 | H | OMe | H | H | —N=N— | H | CF₃ | |
| 918 | H | OMe | H | H | —NH—NH— | H | CF₃ | |
| 919 | H | H | H | H | —N=N— | H | Ph | |
| 920 | H | H | H | H | —NH—NH— | H | Ph | |
| 921 | H | OMe | H | H | —NH—NH— | H | Ph | |
| 922 | H | H | H | H | —N=N— | H | OMe | |
| 923 | H | H | H | H | —NH—NH— | H | OMe | |
| 924 | H | OMe | H | H | —N=N— | H | OMe | |
| 925 | H | OMe | H | H | —NH—NH— | H | OMe | |
| 926 | H | H | H | H | —N=N— | H | OEt | |
| 927 | H | H | H | H | —NH—NH— | H | OEt | |
| 928 | H | OMe | H | H | —N=N— | H | OEt | |
| 929 | H | OMe | H | H | —NH—NH— | H | OEt | |
| 930 | H | H | H | H | —N=N— | H | Me | |
| 931 | H | H | H | H | —NH—NH— | H | Me | |
| 932 | H | H | H | H | —N⁺(O⁻)=N— | H | Me | |
| 933 | H | Cl | H | H | —N=N— | H | Me | |
| 934 | H | Cl | H | H | —NH—NH— | H | Me | |
| 935 | H | Cl | H | H | —N⁺(O⁻)=N— | H | Me | |
| 936 | H | H | H | H | —N=N— | H | Et | |
| 937 | H | H | H | H | —NH—NH— | H | Et | |
| 938 | H | H | H | H | —N⁺(O⁻)=N— | H | Et | |
| 939 | H | Cl | H | H | —N=N— | H | Et | |
| 940 | H | Cl | H | H | —NH—NH— | H | Et | |
| 941 | H | Cl | H | H | —N⁺(O⁻)=N— | H | Et | |
| 942 | H | H | H | H | —N=N— | H | iPr | |

TABLE 6-continued

Compounds of formula (Io)

(Io)

| Cpd | R¹ | R² | R³ | R⁴ | —A—W— | R⁷ | R⁸ | mp. °C. |
|---|---|---|---|---|---|---|---|---|
| 943 | H | H | H | H | —NH—NH— | H | iPr | |
| 944 | H | H | H | H | —N⁺(O⁻)=N— | H | iPr | |
| 945 | H | Cl | H | H | —N=N— | H | iPr | |
| 946 | H | Cl | H | H | —NH—NH— | H | iPr | |
| 947 | H | Cl | H | H | —N⁺(O⁻)N— | H | iPr | |
| 948 | H | H | H | H | —N=N— | H | SMe | |
| 949 | H | H | H | H | —NH—NH— | H | SMe | |
| 950 | H | H | H | H | —N⁺(O⁻)=N— | H | SMe | |
| 951 | H | Cl | H | H | —N=N— | H | SMe | |
| 952 | H | Cl | H | H | —NH—NH— | H | SMe | |
| 953 | H | Cl | H | H | —N⁺(O⁻)=N— | H | SMe | |
| 954 | H | H | H | H | —N=N— | H | Cl | |
| 955 | H | H | H | H | —NH—NH— | H | Cl | |
| 956 | H | H | H | H | —N⁺(O⁻)=N— | H | Cl | |
| 957 | H | Cl | H | H | —N=N— | H | Cl | |
| 958 | H | Cl | H | H | —NH—NH— | H | Cl | |
| 959 | H | Cl | H | H | —N⁺(O⁻)=N— | H | Cl | |
| 960 | H | H | H | H | —N=N— | H | NMe₂ | |
| 961 | H | H | H | H | —NH—NH— | H | NMe₂ | |
| 962 | H | H | H | H | —N⁺(O⁻)=N— | H | NMe₂ | |
| 963 | H | Cl | H | H | —N=N— | H | NMe₂ | |
| 964 | H | Cl | H | H | —NH—NH— | H | NMe₂ | |
| 965 | H | Cl | H | H | —N⁺(O⁻)=N— | H | NMe₂ | |
| 966 | H | H | H | H | —N=N— | H | CO₂Me | |
| 967 | H | H | H | H | —NH—NH— | H | CO₂Me | |
| 968 | H | H | H | H | —N⁺(O⁻)=N— | H | CO₂Me | |
| 969 | H | Cl | H | H | —N=N— | H | CO₂Me | |
| 970 | H | Cl | H | H | —NH—NH— | H | CO₂Me | |
| 971 | H | Cl | H | H | —N⁺(O⁻)=N— | H | CO₂Me | |
| 972 | H | H | H | H | —N=N— | H | COMe | |
| 973 | H | H | H | H | —NH—NH— | H | COMe | |
| 974 | H | H | H | H | —N⁺(O⁻)=N— | H | COMe | |
| 975 | H | Cl | H | H | —N=N— | H | COMe | |
| 976 | H | Cl | H | H | —NH—NH— | H | COMe | |
| 977 | H | Cl | H | H | —N⁺(O⁻)=N— | H | COMe | |
| 978 | H | H | H | H | —N=N— | H | CONMe₂ | |
| 979 | H | H | H | H | —NH—NH— | H | CONMe₂ | |
| 980 | H | H | H | H | —N⁺(O⁻)N— | H | CONMe₂ | |
| 981 | H | Cl | H | H | —N=N— | H | CONMe₂ | |
| 982 | H | Cl | H | H | —NH—NH— | H | CONMe₂ | |
| 983 | H | Cl | H | H | —N⁺(O⁻)=N— | H | CONMe₂ | |
| 984 | H | H | H | H | —N=N— | H | CH₂Ph | |
| 985 | H | H | H | H | —NH—NH— | H | CH₂Ph | |
| 986 | H | H | H | H | —N⁺(O⁻)=N— | H | CH₂Ph | |
| 987 | H | Cl | H | H | —N=N— | H | CH₂Ph | |
| 988 | H | Cl | H | H | —NH—NH— | H | CH₂Ph | |
| 989 | H | Cl | H | H | —N⁺(O⁻)=N— | H | CH₂Ph | |
| 990 | H | H | H | H | —N=N— | H | CN | |
| 991 | H | H | H | H | —NH—NH— | H | CN | |
| 992 | H | H | H | H | —N⁺(O⁻)=N— | H | CN | |
| 993 | H | Cl | H | H | —N=N— | H | CN | |
| 994 | H | Cl | H | H | —NH—NH— | H | CN | |
| 995 | H | Cl | H | H | —N⁺(O⁻)=N— | H | CN | |
| 996 | H | H | H | H | —N=N— | H | NO₂ | |
| 997 | H | H | H | H | —NH—NH— | H | NO₂ | |
| 998 | H | H | H | H | —N⁺(O⁻)=N— | H | NO₂ | |
| 999 | H | Cl | H | H | —N=N— | H | NO₂ | |
| 1000 | H | Cl | H | H | —NH—NH— | H | NO₂ | |
| 1001 | H | Cl | H | H | —N⁺(O⁻)=N— | H | NO₂ | |

TABLE 6-continued

Compounds of formula (Io)

| Cpd | R¹ | R² | R³ | R⁴ | —A—W— | R⁷ | R⁸ | mp. °C. |
|---|---|---|---|---|---|---|---|---|
| 1002 | H | H | H | H | —N=N— | Me | Me | |
| 1003 | H | H | H | H | —NH—NH— | Me | Me | |
| 1004 | H | H | H | H | —N⁺(O⁻)=N— | Me | Me | |

TABLE 7

Compounds of formula (Ip)

| Cpd | R¹ | R² | R³ | R⁴ | —A—W— | R⁹ | mp. °C. |
|---|---|---|---|---|---|---|---|
| 1005 | H | H | H | H | —N=N— | H | |
| 1006 | H | Me | H | H | —NH—NH— | H | |
| 1007 | H | Cl | H | H | —NH—NH— | H | |
| 1008 | H | Me | H | H | —N=N— | H | |
| 1009 | H | H | H | H | —NH—NH— | H | |
| 1010 | H | Cl | H | H | —N=N— | H | |
| 1011 | H | Cl | H | Cl | —N=N— | H | |
| 1012 | H | Br | H | H | —N⁺(O⁻)=N— | H | |
| 1013 | H | OMe | H | H | —N=N— | H | |
| 1014 | H | OMe | H | H | —N=N— | Me | |
| 1015 | H | OMe | H | H | —N=N— | Et | |
| 1016 | H | OMe | H | H | —N=N— | Ph | |
| 1017 | H | OMe | H | H | —NH—NH— | H | |
| 1018 | H | H | H | H | —N=N— | CF₃ | |
| 1019 | H | H | H | H | —NH—NH— | CF₃ | |
| 1020 | H | OMe | H | H | —N=N— | CF₃ | |
| 1021 | H | OMe | H | H | —NH—NH— | CF₃ | |
| 1022 | H | H | H | H | —N=N— | Ph | |
| 1023 | H | H | H | H | —NH—NH— | Ph | |
| 1024 | H | OMe | H | H | —NH—NH— | Ph | |
| 1025 | H | H | H | H | —N=N— | OMe | |
| 1026 | H | H | H | H | —NH—NH— | OMe | |
| 1027 | H | OMe | H | H | —N=N— | OMe | |
| 1028 | H | OMe | H | H | —NH—NH— | OMe | |
| 1029 | H | H | H | H | —N=N— | OEt | |
| 1030 | H | H | H | H | —NH—NH— | OEt | |
| 1031 | H | OMe | H | H | —N=N— | OEt | |
| 1032 | H | OMe | H | H | —NH—NH— | OEt | |
| 1033 | H | H | H | H | —NMe—NMe— | H | |
| 1034 | H | OMe | H | H | —[N(COMe)]₂— | H | |
| 1035 | H | H | H | H | —[N(COMe)]₂— | H | |
| 1036 | H | CF₃ | H | H | —N=N— | H | |
| 1037 | H | CF₃ | H | H | —NH—NH— | H | |
| 1038 | H | Br | H | H | —N=N— | H | |
| 1039 | H | Br | H | H | —NH—NH— | H | |
| 1040 | H | H | Cl | H | —N=N— | H | |
| 1041 | H | H | Cl | H | —NH—NH— | H | |
| 1042 | H | H | H | H | —N=N— | Me | |
| 1043 | H | H | H | H | —NH—NH— | Me | |
| 1044 | H | H | H | H | —N⁺(O⁻)=N— | Me | |
| 1045 | H | Cl | H | H | —N=N— | Me | |
| 1046 | H | Cl | H | H | —NH—NH— | Me | |
| 1047 | H | Cl | H | H | —N⁺(O⁻)=N— | Me | |
| 1048 | H | H | H | H | —N=N— | Et | |
| 1049 | H | H | H | H | —NH—NH— | Et | |
| 1050 | H | H | H | H | —N⁺(O⁻)=N— | Et | |
| 1051 | H | Cl | H | H | —N=N— | Et | |
| 1052 | H | Cl | H | H | —NH—NH— | Et | |
| 1053 | H | Cl | H | H | —N⁺(O⁻)=N— | Et | |
| 1054 | H | H | H | H | —N=N— | iPr | |
| 1055 | H | H | H | H | —NH—NH— | iPr | |
| 1056 | H | H | H | H | —N⁺(O⁻)=N— | iPr | |
| 1057 | H | Cl | H | H | —N=N— | iPr | |
| 1058 | H | Cl | H | H | —NH—NH— | iPr | |
| 1059 | H | Cl | H | H | —N⁺(O⁻)=N— | iPr | |
| 1060 | H | H | H | H | —N=N— | SMe | |
| 1061 | H | H | H | H | —NH—NH— | SMe | |
| 1062 | H | H | H | H | —N⁺(O⁻)=N— | SMe | |
| 1063 | H | Cl | H | H | —N=N— | SMe | |
| 1064 | H | Cl | H | H | —NH—NH— | SMe | |
| 1065 | H | Cl | H | H | —N⁺(O⁻)=N— | SMe | |
| 1066 | H | H | H | H | —N=N— | Cl | |
| 1067 | H | H | H | H | —NH—NH— | Cl | |
| 1068 | H | H | H | H | —N⁺(O⁻)=N— | Cl | |
| 1069 | H | Cl | H | H | —N=N— | Cl | |
| 1070 | H | Cl | H | H | —NH—NH— | Cl | |
| 1071 | H | Cl | H | H | —N⁺(O⁻)=N— | Cl | |
| 1072 | H | H | H | H | —N=N— | NMe₂ | |
| 1073 | H | H | H | H | —NH—NH— | NMe₂ | |
| 1074 | H | H | H | H | —N⁺(O⁻)=N— | NMe₂ | |

TABLE 7-continued

Compounds of formula (Ip)

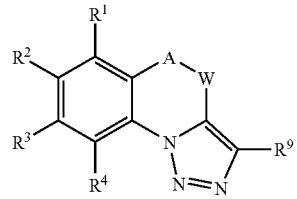

(Ip)

| Cpd | R¹ | R² | R³ | R⁴ | —A—W— | R⁹ | mp. °C. |
|---|---|---|---|---|---|---|---|
| 1075 | H | Cl | H | H | —N=N— | NMe₂ | |
| 1076 | H | Cl | H | H | —NH—NH— | NMe₂ | |
| 1077 | H | Cl | H | H | —N⁺(O⁻)=N— | NMe₂ | |
| 1078 | H | H | H | H | —N=N— | CO₂Me | |
| 1079 | H | H | H | H | —NH—NH— | CO₂Me | |
| 1080 | H | H | H | H | —N⁺(O⁻)=N— | CO₂Me | |
| 1081 | H | Cl | H | H | —N=N— | CO₂Me | |
| 1082 | H | Cl | H | H | —NH—NH— | CO₂Me | |
| 1083 | H | Cl | H | H | —N⁺(O⁻)=N— | CO₂Me | |
| 1084 | H | H | H | H | —N=N— | COMe | |
| 1085 | H | H | H | H | —NH—NH— | COMe | |
| 1086 | H | H | H | H | —N⁺(O⁻)=N— | COMe | |
| 1087 | H | Cl | H | H | —N=N— | COMe | |
| 1088 | H | Cl | H | H | —NH—NH— | COMe | |
| 1089 | H | Cl | H | H | —N⁺(O⁻)=N— | COMe | |
| 1090 | H | H | H | H | —N=N— | CONMe₂ | |
| 1091 | H | H | H | H | —NH—NH— | CONMe₂ | |
| 1092 | H | H | H | H | —N—(O—N— | CONMe₂ | |
| 1093 | H | Cl | H | H | —N=N— | CONMe₂ | |
| 1094 | H | Cl | H | H | —NH—NH— | CONMe₂ | |

TABLE 7-continued

Compounds of formula (Ip)

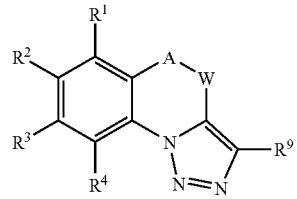

(Ip)

| Cpd | R¹ | R² | R³ | R⁴ | —A—W— | R⁹ | mp. °C. |
|---|---|---|---|---|---|---|---|
| 1095 | H | Cl | H | H | —N⁺(O⁻)=N— | CONMe₂ | |
| 1096 | H | H | H | H | —N=N— | CH₂Ph | |
| 1097 | H | H | H | H | —NH—NH— | CH₂Ph | |
| 1098 | H | H | H | H | —N⁺(O⁻)=N— | CH₂Ph | |
| 1099 | H | Cl | H | H | —N=N— | CH₂Ph | |
| 1100 | H | Cl | H | H | —NH—NH— | CH₂Ph | |
| 1101 | H | Cl | H | H | —N⁺(O⁻)=N— | CH₂Ph | |
| 1102 | H | H | H | H | —N=N— | CN | |
| 1103 | H | H | H | H | —NH—NH— | CN | |
| 1104 | H | H | H | H | —N⁺(O⁻)=N— | CN | |
| 1105 | H | Cl | H | H | —N=N— | ON | |
| 1106 | H | Cl | H | H | —NH—NH— | ON | |
| 1107 | H | Cl | H | H | —N⁺(O⁻)=N— | ON | |
| 1108 | H | H | H | H | —N=N— | NO₂ | |
| 1109 | H | H | H | H | —NH—NH— | NO₂ | |
| 1110 | H | H | H | H | —N⁺(O⁻)=N— | NO₂ | |
| 1111 | H | Cl | H | H | —N=N— | NO₂ | |
| 1112 | H | Cl | H | H | —NH—NH— | NO₂ | |
| 1113 | H | Cl | H | H | —N⁺(O⁻)=N— | NO₂ | |

TABLE 8

Compounds of formula (Iq)

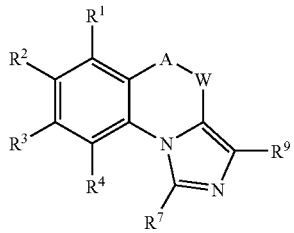

(Iq)

| Cpd | R¹ | R² | R³ | R⁴ | —A—W— | R⁷ | R⁹ | mp. °C. |
|---|---|---|---|---|---|---|---|---|
| 1114 | H | H | H | H | —N=N— | H | H | |
| 1115 | H | Me | H | H | —NH—NH— | H | H | |
| 1116 | H | Cl | H | H | —NH—NH— | H | H | |
| 1117 | H | Me | H | H | —N=N— | H | H | |
| 1118 | H | H | H | H | —NH—NH— | H | H | |
| 1119 | H | Cl | H | H | —N=N— | H | H | |
| 1120 | H | Cl | H | Cl | —N=N— | H | H | |
| 1121 | H | Br | H | H | —N⁺(O⁻)=N— | H | H | |
| 1122 | H | OMe | H | H | —N=N— | H | H | |
| 1123 | H | OMe | H | H | —N=N— | Me | H | |
| 1124 | H | OMe | H | H | —N=N— | Et | H | |
| 1125 | H | OMe | H | H | —N=N— | Ph | H | |
| 1126 | H | OMe | H | H | —NH—NH— | H | H | |
| 1127 | H | H | H | H | —N=N— | CF₃ | H | |
| 1128 | H | H | H | H | —NH—NH— | CF₃ | H | |
| 1129 | H | OMe | H | H | —N=N— | CF₃ | H | |
| 1130 | H | OMe | H | H | —NH—NH— | CF₃ | H | |
| 1131 | H | H | H | H | —N=N— | Ph | H | |
| 1132 | H | H | H | H | —NH—NH— | Ph | H | |

TABLE 8-continued

Compounds of formula (Iq)

| Cpd | R¹ | R² | R³ | R⁴ | —A—W— | R⁷ | R⁹ | mp. °C. |
|---|---|---|---|---|---|---|---|---|
| 1133 | H | OMe | H | H | —NH—NH— | Ph | H | |
| 1134 | H | H | H | H | —N=N— | OMe | H | |
| 1135 | H | H | H | H | —NH—NH— | OMe | H | |
| 1136 | H | OMe | H | H | —N=N— | OMe | H | |
| 1137 | H | OMe | H | H | —NH—NH— | OMe | H | |
| 1138 | H | H | H | H | —N=N— | OEt | H | |
| 1139 | H | H | H | H | —NH—NH— | OEt | H | |
| 1140 | H | OMe | H | H | —N=N— | OEt | H | |
| 1141 | H | OMe | H | H | —NH—NH— | OEt | H | |
| 1142 | H | H | H | H | —NMe—NMe— | H | H | |
| 1143 | H | OMe | H | H | —[N(COMe)]₂— | H | H | |
| 1144 | H | H | H | H | —[N(COMe)]₂— | H | H | |
| 1145 | H | CF₃ | H | H | —N=N— | H | H | |
| 1146 | H | CF₃ | H | H | —NH—NH— | H | H | |
| 1147 | H | Br | H | H | —N=N— | H | H | |
| 1148 | H | Br | H | H | —NH—NH— | H | H | |
| 1149 | H | H | Cl | H | —N=N— | H | H | |
| 1150 | H | H | Cl | H | —NH—NH— | H | H | |
| 1151 | H | H | H | H | —N=N— | Me | H | |
| 1152 | H | H | H | H | —NH—NH— | Me | H | |
| 1153 | H | H | H | H | —N⁺(O⁻)=N— | Me | H | |
| 1154 | H | Cl | H | H | —N=N— | Me | H | |
| 1155 | H | Cl | H | H | —NH—NH— | Me | H | |
| 1156 | H | Cl | H | H | —N⁺(O⁻)=N— | Me | H | |
| 1157 | H | H | H | H | —N=N— | Et | H | |
| 1158 | H | H | H | H | —NH—NH— | Et | H | |
| 1159 | H | H | H | H | —N⁺(O⁻)=N— | Et | H | |
| 1160 | H | Cl | H | H | —N=N— | Et | H | |
| 1161 | H | Cl | H | H | —NH—NH— | Et | H | |
| 1162 | H | Cl | H | H | —N⁺(O⁻)=N— | Et | H | |
| 1163 | H | H | H | H | —N=N— | iPr | H | |
| 1164 | H | H | H | H | —NH—NH— | iPr | H | |
| 1165 | H | H | H | H | —N⁺(O⁻)=N— | iPr | H | |
| 1166 | H | Cl | H | H | —N=N— | iPr | H | |
| 1167 | H | Cl | H | H | —NH—NH— | iPr | H | |
| 1168 | H | Cl | H | H | —N⁺(O⁻)=N— | iPr | H | |
| 1169 | H | H | H | H | —N=N— | SMe | H | |
| 1170 | H | H | H | H | —NH—NH— | SMe | H | |
| 1171 | H | H | H | H | —N⁺(O⁻)=N— | SMe | H | |
| 1172 | H | Cl | H | H | —N=N— | SMe | H | |
| 1173 | H | Cl | H | H | —NH—NH— | SMe | H | |
| 1174 | H | Cl | H | H | —N⁺(O⁻)=N— | SMe | H | |
| 1175 | H | H | H | H | —N=N— | Cl | H | |
| 1176 | H | H | H | H | —NH—NH— | Cl | H | |
| 1177 | H | H | H | H | —N⁺(O⁻)=N— | Cl | H | |
| 1178 | H | Cl | H | H | —N=N— | Cl | H | |
| 1179 | H | Cl | H | H | —NH—NH— | Cl | H | |
| 1180 | H | Cl | H | H | —N⁺(O⁻)=N— | Cl | H | |
| 1181 | H | H | H | H | —N=N— | NMe₂ | H | |
| 1182 | H | H | H | H | —NH—NH— | NMe₂ | H | |
| 1183 | H | H | H | H | —N⁺(O⁻)=N— | NMe₂ | H | |
| 1184 | H | Cl | H | H | —N=N— | NMe₂ | H | |
| 1185 | H | Cl | H | H | —NH—NH— | NMe₂ | H | |
| 1186 | H | Cl | H | H | —N⁺(O⁻)=N— | NMe₂ | H | |
| 1187 | H | H | H | H | —N=N— | CO₂Me | H | |
| 1188 | H | H | H | H | —NH—NH— | CO₂Me | H | |
| 1189 | H | H | H | H | —N⁺(O⁻)=N— | CO₂Me | H | |
| 1190 | H | Cl | H | H | —N=N— | CO₂Me | H | |
| 1191 | H | Cl | H | H | —NH—NH— | CO₂Me | H | |
| 1192 | H | Cl | H | H | —N⁺(O⁻)=N— | CO₂Me | H | |
| 1193 | H | H | H | H | —N=N— | COMe | H | |

TABLE 8-continued

Compounds of formula (Iq)

(Iq)

| Cpd | R¹ | R² | R³ | R⁴ | —A—W— | R⁷ | R⁹ | mp. ° C. |
|---|---|---|---|---|---|---|---|---|
| 1194 | H | H | H | H | —NH—NH— | COMe | H | |
| 1195 | H | H | H | H | —N⁺(O⁻)=N— | COMe | H | |
| 1196 | H | Cl | H | H | —N=N— | COMe | H | |
| 1197 | H | Cl | H | H | —NH—NH— | COMe | H | |
| 1198 | H | Cl | H | H | —N⁺(O⁻)=N— | COMe | H | |
| 1199 | H | H | H | H | —N=N— | CONMe₂ | H | |
| 1200 | H | H | H | H | —NH—NH— | CONMe₂ | H | |
| 1201 | H | H | H | H | —N⁺(O⁻)=N— | CONMe₂ | H | |
| 1202 | H | Cl | H | H | —N—N— | CONMe₂ | H | |
| 1203 | H | Cl | H | H | —NH—NH— | CONMe₂ | H | |
| 1204 | H | Cl | H | H | —N⁺(O⁻)=N— | CONMe₂ | H | |
| 1205 | H | H | H | H | —N=N— | CH₂Ph | H | |
| 1206 | H | H | H | H | —NH—NH— | CH₂Ph | H | |
| 1207 | H | H | H | H | —N⁺(O⁻)=N— | CH₂Ph | H | |
| 1208 | H | Cl | H | H | —N=N— | CH₂Ph | H | |
| 1209 | H | Cl | H | H | —NH—NH— | CH₂Ph | H | |
| 1210 | H | Cl | H | H | —N⁺(O⁻)=N— | CH₂Ph | H | |
| 1211 | H | H | H | H | —N=N— | CN | H | |
| 1212 | H | H | H | H | —NH—NH— | CN | H | |
| 1213 | H | H | H | H | —N⁺(O⁻)=N— | CN | H | |
| 1214 | H | Cl | H | H | —N=N— | CN | H | |
| 1215 | H | Cl | H | H | —NH—NH— | CN | H | |
| 1216 | H | Cl | H | H | —N⁺(O⁻)=N— | CN | H | |
| 1217 | H | H | H | H | —N=N— | NO₂ | H | |
| 1218 | H | H | H | H | —NH—NH— | NO₂ | H | |
| 1219 | H | H | H | H | —N⁺(O⁻)=N— | NO₂ | H | |
| 1220 | H | Cl | H | H | —N=N— | NO₂ | H | |
| 1221 | H | Cl | H | H | —NH—NH— | NO₂ | H | |
| 1222 | H | Cl | H | H | —N⁺(O⁻)=N— | NO₂ | H | |
| 1223 | H | OMe | H | H | —N=N— | H | Me | |
| 1224 | H | OMe | H | H | —N=N— | H | Et | |
| 1225 | H | OMe | H | H | —N=N— | H | Ph | |
| 1226 | H | H | H | H | —N=N— | H | CF₃ | |
| 1227 | H | H | H | H | —NH—NH— | H | CF₃ | |
| 1228 | H | OMe | H | H | —N=N— | H | CF₃ | |
| 1229 | H | OMe | H | H | —NH—NH— | H | CF₃ | |
| 1230 | H | H | H | H | —N=N— | H | Ph | |
| 1231 | H | H | H | H | —NH—NH— | H | Ph | |
| 1232 | H | OMe | H | H | —NH—NH— | H | Ph | |
| 1233 | H | H | H | H | —N=N— | H | OMe | |
| 1234 | H | H | H | H | —NH—NH— | H | OMe | |
| 1235 | H | OMe | H | H | —N=N— | H | OMe | |
| 1236 | H | OMe | H | H | —NH—NH— | H | OMe | |
| 1237 | H | H | H | H | —N=N— | H | OEt | |
| 1238 | H | H | H | H | —NH—NH— | H | OEt | |
| 1239 | H | OMe | H | H | —N=N— | H | OEt | |
| 1240 | H | OMe | H | H | —NH—NH— | H | OEt | |
| 1241 | H | H | H | H | —N=N— | H | Me | |
| 1242 | H | H | H | H | —NH—NH— | H | Me | |
| 1243 | H | H | H | H | —N⁺(O⁻)=N— | H | Me | |
| 1244 | H | Cl | H | H | —N=N— | H | Me | |
| 1245 | H | Cl | H | H | —NH—NH— | H | Me | |
| 1246 | H | Cl | H | H | —N⁺(O⁻)=N— | H | Me | |
| 1247 | H | H | H | H | —N=N— | H | Et | |
| 1248 | H | H | H | H | —NH—NH— | H | Et | |
| 1249 | H | H | H | H | —N⁺(O⁻)=N— | H | Et | |
| 1250 | H | Cl | H | H | —N=N— | H | Et | |
| 1251 | H | Cl | H | H | —NH—NH— | H | Et | |
| 1252 | H | Cl | H | H | —N⁺(O⁻)=N— | H | Et | |
| 1253 | H | H | H | H | —N=N— | H | iPr | |
| 1254 | H | H | H | H | —NH—NH— | H | iPr | |

TABLE 8-continued

Compounds of formula (Iq)

(Iq)

| Cpd | R¹ | R² | R³ | R⁴ | —A—W— | R⁷ | R⁹ | mp. ° C. |
|---|---|---|---|---|---|---|---|---|
| 1255 | H | H | H | H | —N⁺(O⁻)N— | H | Pr | |
| 1256 | H | Cl | H | H | —N=N— | H | iPr | |
| 1257 | H | Cl | H | H | —NH—NH— | H | iPr | |
| 1258 | H | Cl | H | H | —N⁺(O⁻)=N— | H | iPr | |
| 1259 | H | H | H | H | —N=N— | H | SMe | |
| 1260 | H | H | H | H | —NH—NH— | H | SMe | |
| 1261 | H | H | H | H | —N⁺(O⁻)=N— | H | SMe | |
| 1262 | H | Cl | H | H | —N=N— | H | SMe | |
| 1263 | H | Cl | H | H | —NH—NH— | H | SMe | |
| 1264 | H | Cl | H | H | —N⁺(O⁻)=N— | H | SMe | |
| 1265 | H | H | H | H | —N=N— | H | Cl | |
| 1266 | H | H | H | H | —NH—NH— | H | Cl | |
| 1267 | H | H | H | H | —N⁺(O⁻)=N— | H | Cl | |
| 1268 | H | Cl | H | H | —N=N— | H | Cl | |
| 1269 | H | Cl | H | H | —NH—NH— | H | Cl | |
| 1270 | H | Cl | H | H | —N⁺(O⁻)=N— | H | Cl | |
| 1271 | H | H | H | H | —N=N— | H | NMe₂ | |
| 1272 | H | H | H | H | —NH—NH— | H | NMe₂ | |
| 1273 | H | H | H | H | —N⁺(O⁻)=N— | H | NMe₂ | |
| 1274 | H | Cl | H | H | —N=N— | H | NMe₂ | |
| 1275 | H | Cl | H | H | —NH—NH— | H | NMe₂ | |
| 1276 | H | Cl | H | H | —N⁺(O⁻)=N— | H | NMe₂ | |
| 1277 | H | H | H | H | —N=N— | H | CO₂Me | |
| 1278 | H | H | H | H | —NH—NH— | H | CO₂Me | |
| 1279 | H | H | H | H | —N⁺(O⁻)=N— | H | CO₂Me | |
| 1280 | H | Cl | H | H | —N=N— | H | CO₂Me | |
| 1281 | H | Cl | H | H | —NH—NH— | H | CO₂Me | |
| 1282 | H | Cl | H | H | —N⁺(O⁻)=N— | H | CO₂Me | |
| 1283 | H | H | H | H | —N=N— | H | COMe | |
| 1284 | H | H | H | H | —NH—NH— | H | COMe | |
| 1285 | H | H | H | H | —N⁺(O⁻)=N— | H | COMe | |
| 1286 | H | Cl | H | H | —N=N— | H | COMe | |
| 1287 | H | Cl | H | H | —NH—NH— | H | COMe | |
| 1288 | H | Cl | H | H | —N⁺(O⁻)=N— | H | COMe | |
| 1289 | H | H | H | H | —N=N— | H | CONMe₂ | |
| 1290 | H | H | H | H | —NH—NH— | H | CONMe₂ | |
| 1291 | H | H | H | H | —N⁺(O⁻)=N— | H | CONMe₂ | |
| 1292 | H | Cl | H | H | —N=N— | H | CONMe₂ | |
| 1293 | H | Cl | H | H | —NH—NH— | H | CONMe₂ | |
| 1294 | H | Cl | H | H | —N⁺(O⁻)=N— | H | CONMe₂ | |
| 1295 | H | H | H | H | —N=N— | H | CH₂Ph | |
| 1296 | H | H | H | H | —NH—NH— | H | CH₂Ph | |
| 1297 | H | H | H | H | —N⁺(O⁻)=N— | H | CH₂Ph | |
| 1298 | H | Cl | H | H | —N=N— | H | CH₂Ph | |
| 1299 | H | Cl | H | H | —NH—NH— | H | CH₂Ph | |
| 1300 | H | Cl | H | H | —N⁺(O⁻)=N— | H | CH₂Ph | |
| 1301 | H | H | H | H | —N=N— | H | CN | |
| 1302 | H | H | H | H | —NH—NH— | H | CN | |
| 1303 | H | H | H | H | —N⁺(O⁻)=N— | H | CN | |
| 1304 | H | Cl | H | H | —N=N— | H | CN | |
| 1305 | H | Cl | H | H | —NH—NH— | H | CN | |
| 1306 | H | Cl | H | H | —N⁺(O⁻)=N— | H | CN | |
| 1307 | H | H | H | H | —N=N— | H | NO₂ | |
| 1308 | H | H | H | H | —NH—NH— | H | NO₂ | |
| 1309 | H | H | H | H | —N⁺(O⁻)=N— | H | NO₂ | |
| 1310 | H | Cl | H | H | —N=N— | H | NO₂ | |
| 1311 | H | Cl | H | H | —NH—NH— | H | NO₂ | |
| 1312 | H | Cl | H | H | —N⁺(O⁻)=N— | H | NO₂ | |
| 1313 | Me | H | Me | H | —N=N— | H | CO₂H | |
| 1314 | Me | H | Me | H | —N=N— | H | CO₂Et | |
| 1315 | Me | H | Me | H | —N=N— | H | SCH₂Ph | |

TABLE 8-continued

Compounds of formula (Iq)

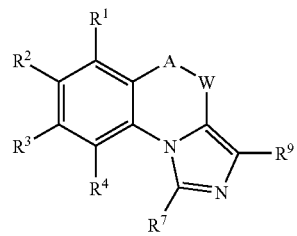

(Iq)

| Cpd | R¹ | R² | R³ | R⁴ | —A—W— | R⁷ | R⁹ | mp. ° C. |
|---|---|---|---|---|---|---|---|---|
| 1316 | H | H | H | H | —N=N— | Me | Me | |
| 1317 | H | H | H | H | —NH—NH— | Me | Me | |
| 1318 | H | H | H | H | —N⁺(O⁻)=N— | Me | Me | |

The compounds of the invention possess valuable herbicidal and plant growth regulatory properties.

According to a further feature of the present invention, there is provided the use as a herbicide or plant growth regulator characterised by a method wherein in the compound of formula (I) or a salt thereof is applied in an effective amount for the control of weeds or for regulating the growth of plants at a plant locus. For this purpose, the said compound is normally used in the form of a herbicidal composition (i.e. in association with compatible diluents or carriers and/or surface active agents suitable for use in herbicidal compositions), for example as hereinafter described. By application to the 'plant locus' is meant application, for example to the plant growing medium, such as soil, as well as to the seeds, emerging seedlings, roots, stems, leaves or other plant parts.

The compounds of the formula (I) and their salts, all termed hereinbelow as compounds of formula (I), have an excellent herbicidal activity against a broad range of economically important monocotyledonous and dicotyledonous harmful plants.

The compounds of formula (I) also act efficiently on perennial weeds which produce shoots from rhizomes, root stocks or other perennial organs and which are difficult to control. In this context, the substances can be applied pre-planting, pre-emergence or post-emergence.

Specifically, examples may be mentioned of some representatives of the monocotyledonous and dicotyledonous weed flora which can be controlled by the compounds of formula (I), without the enumeration being a restriction to certain species.

Amongst the monocotyledonous weed species, those on which the active substances act efficiently are, for example, *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea* and *Cyperus* species from the annual group and, amongst the perennial species, *Agropyron, Cynodon, Imperata* and *Sorghum* and also perennial *Cyperus* species. In the case of dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* amongst the annuals and *Convolvulus, Cirsium, Rumex* and *Artemisia* in the case of the perennial weeds. Herbicidal action is also achieved in the case of dicotyledonous harmful plants such as *Ambrosia, Anthemis, Carduus, Centaurea, Chenopodium, Cirsium, Convolvulus, Datura, Emex, Galeopsis, Galinsoga, Kochia, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

Harmful plants occurring under the specific cultivation conditions of rice, such as, for example, *Sagittaria, Alisma, Eleocharis, Scirpus* and *Cyperus*, are also well controlled by the active substances according to the invention.

If the compounds according to the invention are applied to the soil surface before germination (pre-emergence of the weeds), then the weed seedlings are either prevented completely from emerging or the weeds grow until they have reached the cotyledon stage, but then their growth stops and they finally die completely after three to four weeks have elapsed.

When the active substances are applied post-emergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledonous weeds, some crop plants of economically important crops such as, for example, wheat, barley, rye, triticale, rice, maize, sugar beet, cotton or soybeans (particularly wheat, barley, rice or maize) are damaged only to an insignificant extent or not at all, if an appropriate dosage is applied. For these reasons, the present compounds are in some cases suitable for the selective control of undesired vegetation in stands of agriculturally useful plants or in stands of ornamental plants.

The activity allows to employ the compounds as effective herbicidal active ingredients pre- and post-emergence for controlling broad-leaved weeds and grass weeds at relatively low dosage as a selective herbicide in some crops. Alternatively the compounds can be used effectively at some higher dosage for the control of a broad range of dicotyledonous weeds and monocotyledonous weeds in plantation crops and on uncultivated land and, by means of specific application techniques, also for inter-row treatment in agricultural row crops such as maize, cotton and the like.

The compositions according to the invention can be used to selectively control annual and perennial harmful plants in plantation crops such as oil palm, coconut palm, India-rubber tree, citrus, pineapples, cotton, coffee, cocoa and the like, as well as in fruit production and viticulture. Equally, the combinations according to the invention can be employed in arable crop production using the no-till, or zero-till, method.

Another object of the invention is thus the selective weed control in plantation crops by applying the compounds according to the invention as herbicides.

Alternatively, they can be used as very effective herbicides in a non-selective manner on paths, open spaces and industrial sites and the like to keep these areas free from undesirable vegetation.

The invention thus also relates to a method of controlling undesirable vegetation which comprises applying one or more type A herbicides together with one or more type B herbicides and a type C anionic surfactant to the harmful plants, parts of these plants or the area under cultivation.

In addition, the substances according to the invention have outstanding growth-regulatory properties in crop plants. They engage in the plants' metabolism in a regulatory fashion and can thus be employed for influencing plant constituents in a targeted fashion and for facilitating harvesting, such as, for example, by triggering desiccation and stunted growth. Moreover, they are also suitable for generally controlling and inhibiting undesired vegetative growth without simultaneously killing the plants. Inhibiting vegetative growth plays an important role in many monocotyledonous and dicotyledonous crops since lodging can be reduced, or prevented completely, hereby.

Due to their herbicidal and plant-growth regulatory properties, the compounds of formula (I) can also be employed for controlling harmful plants in crops of known genetically modified plants, or genetically modified plants yet to be developed. As a rule, the transgenic plants are distinguished by particular advantageous properties, for example by resistances to certain pesticides, mainly certain herbicides, resistances to plant diseases or pathogens of plant diseases, such as certain insects or microorganisms such as fungi, bacteria or viruses. Other particular properties relate, for example, to the harvested material with regard to quantity, quality, storage properties, composition and specific constituents. Thus, transgenic plants are known where the starch content is increased or the starch quality is altered or those where the harvested material has a different fatty acid spectrum.

The compounds of formula (I) are preferably employed in economically important transgenic crops of useful plants and ornamentals, for example cereals such as wheat, barley, rye, oats, sorghum and millet, rice, cassava and maize, or else crops of sugar beet, cotton, soya, oil seed rape, potatoes, tomatoes, peas and other vegetables.

The compounds of formula (I) can preferably be employed as herbicides in crops of useful plants which are resistant to the phytotoxic effects of the herbicides or have been rendered thus by means of genetic engineering.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-01 31624). For example, several cases have been described of

- genetic engineering modifications of crop plants with the purpose of modifying the starch synthesized in the plants (for example WO 92/11376, WO 92/14827, WO 91/19806),
- transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659),
- transgenic crop plants, for example cotton, which are capable of producing Bacillus thuringiensis toxins (Bt toxins) which make the plants resistant to specific pests (EP-A-0142924, EP-A-0193259),
- transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments.

For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds of formula (I) can preferably be employed in transgenic crops which are resistant to herbicides from the group of the sulfonylureas, glufosinate-ammonium or glyphosate-isopropylammonium and analogous active substances.

When the compounds of formula (I) are used in transgenic crops, effects other than the herbicidal effects to be observed in other crops are frequently found which are specific for application in the particular transgenic crop, for example an altered or specifically widened weed spectrum which can be controlled, altered application rates which may be employed for application, preferably good combining ability with the herbicides to which the transgenic crop is resistant, and an effect on growth and yield of the transgenic crop plants.

The invention therefore also relates to the use of the compounds of formula (I) as herbicides for controlling harmful plants in transgenic crop plants.

The use according to the invention for controlling harmful plants or for regulating the growth of plants also includes the case where the compounds of formula (I) are only formed in the plant or the soil from a precursor ("prodrug") after its application to the plant.

The compounds of formula (I) can be employed in the conventional preparations as wettable powders, emulsifiable concentrates, sprayable solutions, dusts or granules. The invention therefore also relates to herbicidal and plant-growth-regulating compositions which comprise compounds of formula (I).

According to a further feature of the present invention, there is provided a herbicidal or plant growth regulating composition comprising an effective amount of a compound of formula (I) as defined above or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of the invention]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use (including tank mixtures).

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd. Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonate, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of compounds of formula (I).

The concentration of compounds of formula (I) in wettable powders is, for example, approximately 10 to 90% by weight, the remainder to 100% by weight being composed of customary formulation components. In the case of emulsifiable concentrates, the concentration of compounds of formula (I) can amount to approximately 1 to 90, preferably 5 to 80% by weight. Formulations in the form of dusts usually comprise 1 to 30% by weight of compounds of formula (I), preferably in most cases 5 to 20% by weight of compounds of formula (I), while sprayable solutions comprise approximately 0.05 to 80, preferably 2 to 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise between 1 and 95% by weight of active substance, preferably between 10 and 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or growth regulators, for example as a premix or as tank mixes.

Components which may be employed for the active substances according to the invention in mixed formulations or in tank mix are, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors) and literature cited therein. Herbicides which are known from the literature and which can be mentioned, which can be combined with the compounds of the formula (I), are, for example, the following active substances (Note: the compounds are either designated by the common name according to the International Organization for Standardization (ISO) or using the chemical name, if appropriate together with a customary code number):
acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516 H, i.e. 5-fluoro-2-phenyl-4H-3,1-benzoxazin-4-one; beflubutamid; benazolin(-ethyl); benfluralin; benfuresate; bensulfuron(-methyl); bensulide; bentazone(-sodium); benzobicyclone; benzofenap; benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDM, i.e. 2-chloro-N,N-di-2-propenylacetamide; CDEC, i.e. 2-chloroallyl diethyidithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl), cinmethylin; cinosulfuron; clethodim; clefoxydim, clodinafop and its ester derivatives (for example clodinafop-propargyl); clomazone; clomeprop; cloproxydim; clopyralid; clopyrasulfuron(-methyl); cloransulam(-methyl); cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl;-diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethyl-ethyl)-N-methyl-1H-pyrazole-4-carboxamide;
endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl]ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac(-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; flurochloridone; fluroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate (-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyidymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenopbutyl; pretilachlor; primisulfuron(-methyl); procarbazone (-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy) phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FM C-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl) phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Controlling harmful plants selectively is of particular interest in crops of useful plants and ornamentals. Even though the compounds (I) already exhibit very good to sufficient selectivity in many crops, it is possible, in principle, that symptoms of phytotoxicity occur on the cultivated plants in some crops and especially also in the case of mixtures with other herbicides which are less selective. In this respect, combinations of compounds (I) according to the invention which are of particular interest are those which contain the compounds (I) or their combinations with other herbicides or pesticides and safeners. The safeners, which are employed in such an amount that they act as antidote, reduce the phytotoxic side effects of the herbicides/pesticides employed, for example in economically important crops such as cereals (wheat, barley, rye, maize, rice, sorghum and millet), sugar beet, sugar cane, oilseed rape, cotton and soybeans, preferably cereals. The following groups of compounds are examples of suitable safeners for the compounds (I) and their combinations with further pesticides:

a) compounds of the dichlorophenylpyrazoline-3-carboxylic acid type, preferably compounds such as ethyl 1-(2,4-dichlorophenyl)-5-(ethoxycarbonyl)-5-methyl-2-pyrazoline-3-carboxylate (S1-1) ("Mefenpyr-diethyl", PM, pp. 594-595) and related compounds as they are described in WO 91/07874;

b) dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as they are described in EP-A-333 131 and EP-A-269 806;

c) compounds of the triazolecarboxylic acids type, preferably compounds such as fenchlorazol (and its ethyl ester), i.e. ethyl 1-(2,4-dichlorophenyl)-5-trichloromethyl-(1H)-1,2,4-triazole-3-carboxylate (S1-6), and related compounds (see EP-A-174 562 and EP-A-346 620);

d) compounds of the 5-benzyl- or 5-phenyl-2-isoxazoline-3-carboxylic acid type or the 5,5-diphenyl-2-isoxazoline-3-carboxylic acid, preferably compounds such as ethyl 5-(2, 4-dichlorobenzyl)-2-isoxazoline-3-carboxylate (S1-7) or ethyl 5-phenyl-2-isoxazoline-3-carboxylate (S1-8) and related compounds as they are described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as they are described in German Patent Application (WO-A-95/07897);

e) compounds of the 8-quinolinoxyacetic acid type (S2), preferably 1-methylhexyl-1-yl (5-chloro-8-quinolinoxy)acetate (common name "cloquintocet-mexyl") (S2-1) (see PM, pp.195-196) 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8- quinolinoxy)acetate (S2-5), methyl (5-chloro-8-quinolinoxy)acetate (S2-6), allyl (5-chloro-8-quinolinoxy)acetate (S2-7), 2-(2-propylideneiminooxy)-1-ethyl (5-chloro-8-quinolinoxy)acetate (S2-8), 2-oxoprop-1-yl (5-chloro-8-quinolinoxy)acetate (S2-9), and related compounds as are described in EP-A-86 750, EP-A-94 349 and EP-A-191 736 or EP-A-0 492 366;

f) compounds of the (5-chloro-8-quinolinoxy)malonic acid type, preferably compounds such as diethyl (5-chloro-8-quinolinoxy)malonate, diallyl (5-chloro-8-quinolinoxy) malonate, methylethyl (5-chloro-8-quinolinoxy)malonate and related compounds as are described in EP-A-0 582 198;

g) active substances of the phenoxyacetic or phenoxypropionic acid derivatives type or of the aromatic carboxylic acids type, such as, for example, 2,4-dichlorophenoxyacetic acids (and its esters) (2,4-D), 4-chloro-2-methylphenoxypropionic esters (mecoprop), MCPA or 3,6-dichloro-2-methoxybenzoic acid (and its esters) (dicamba);

h) active substances of the pyrimidines type which are employed in rice as soil-acting safeners, such as, for example, "fenclorim" (PM, pp. 386-387) (=4,6-dichloro-2-phenylpyrimidine), which is also known as safener for pretilachlor in seeded rice;

i) active substances of the dichloroacetamides type, which are frequently employed as pre-emergence safeners (soil-acting safeners), such as, for example, "dichlormid" (PM, pp. 270-271) (=N,N-diallyl-2,2-dichloroacetamide), "R-29148" (=3-dichloroacetyl-2,2,5-trimethyl-1,3-oxazolidine, by Stauffer), "benoxacor" (PM, pp. 74-75) (=4-dichloroacetyl-3,4-dihydro-3-methyl-2H-1,4-benzoxazine), "PPG-1292" (=N-allyl-N-[(1,3-dioxolan-2-yl)methyl]dichloroacetamide by PPG Industries), "DK-24" (=N-allyl-N-[(allylaminocarbonyl)methyl]dichloroacetamide by Sagro-Chem), "AD-67" or "MON 4660" (=3-dichloroacetyl-1-oxa-3-azaspiro[4,5]decane by Nitrokemia and Monsanto, respectively), "diclonon" or "BAS145138" or "LAB145138" (=3-dichloroacetyl-2,5,5-trimethyl-1,3-diazabicyclo[4.3.0]nonane by BASF) and "furilazol" or "MON 13900" (see PM, 482-483) (=(RS)-3-dichloroacetyl-5-(2-furyl)-2,2-dimethyloxazolidine);

j) active substances of the dichloroacetone derivatives type, such as, for example, "MG 191" (CAS Reg. No. 96420-72-3) (=2-dichloromethyl-2-methyl-1,3-dioxolane by Nitrokemia), which is known as safener for maize;

k) active substances of the oxyimino compounds type, which are known as seed treatment products, such as, for example, "oxabetrinil" (PM, pp. 689) (=(Z)-1,3-dioxolan-2-ylmethoxyimino(phenyl)-acetonitrile), which is known as seed-treatment safener for sorghum and millet against metolachlor damage, "fluxofenim" (PM, pp. 467-468) (=1-(4-chlorophenyl)-2,2,2-trifluoro-1-ethanone O-(1,3-dioxolan-2-ylmethyl)oxime, which is known as seed-dressing safener for sorghum and millet against metolachlor damage, and "cyometrinil" or "-CGA-43089" (PM, p.1170) (=(Z)-cyanomethoxy-imino(phenyl)acetonitrile), which is known as seed-treatment safener for sorghum and millet against metolachlor damage;

l) active substances of the thiazolecarboxylic ester type, which are known as seed treatment products, such as, for example, "flurazole" (PM, pp. 450-451) (=benzyl 2-chloro-4-trifluoromethyl-1,3-thiazole-5-carboxylate), which is known as seed-treatment safener for sorghum and millet against alachlor and metolachlor damage;

m) active substances of the naphthalenedicarboxylic acid derivatives type, which are known as seed treatment products, such as, for example, "naphthalic anhydride" (PM, p.1009-1010) (=1,8-naphthalenedicarboxylic anhydride), which is known as seed-treatment safener for maize against thiocarbamate herbicide damage;

n) active substances of the chromanacetic acid derivatives type, such as, for example, "CL 304415" (CAS Reg. No. 31541-57-8) (=2-(4-carboxychroman-4-yl)acetic acid by American Cyanamid), which is known as safener for maize against damage by imidazolinones;

o) active substances which, in addition to a herbicidal action against harmful plants, also exhibit a safener action in connection with crop plants such as rice, such as, for example, "dimepiperate" or "MY-93" (PM, pp. 302-303) (=S-1-methyl-1-phenylethyl piperidine-1-carbothioate), which is known as safener for rice against damage by the herbicide molinate, "daimuron" or"SK 23" (PM, p. 247) (=1-(1-methyl-1-phenylethyl)-3-p-tolylurea), which is known as safener for rice against damage by the herbicide imazosulfuron, "cumyluron"="JC-940" (=3-(2-chlorophenylmethyl)-1-(1-methyl-1-phenyl-ethyl)urea, see JP-A-60087254), which is known as safener for rice against damage by several herbicides, "methoxyphenone" or"NK 049" (=3,3'-dimethyl-4-methoxybenzophenone), which is known as safener for rice against damage by several herbicides, "CSB" (=1-bromo-4-(chloromethylsulfonyl)benzene) (CAS Reg. No. 54091-06-4, by Kumiai), which is known as safener in rice against damage by several herbicides;

p) N-acylsulfonamides of the formula (S3) and their salts

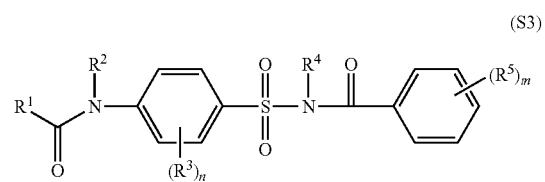

(S3)

as are described in WO-A-97/45016;

q) acylsulfamoylbenzamides of the formula (S4), if appropriate also in salt form,

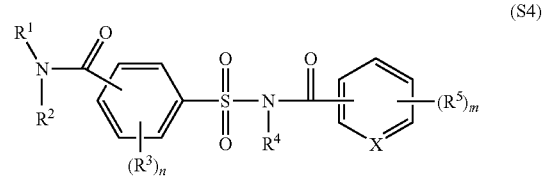

(S4)

as are described in International Application No. PCT/EP98/06097; and r) compounds of the formula (S5),

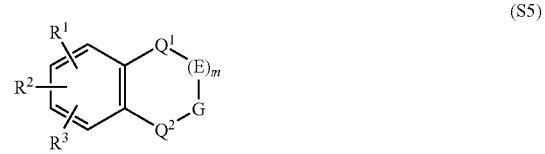

(S5)

as are described in WO-A 98/13 361, including the stereoisomers and the salts conventionally used in agriculture.

Amongst the safeners mentioned, those which are of particular interest are (S1-1) and (S1-9) and (S2-1), in particular (S1-1) and (S1-9).

Some of the safeners are already known as herbicides and therefore simultaneously also display a protective action in connection with the crop plants in addition to the herbicidal action in connection with harmful plants.

The weight ratio of herbicide (mixture) to safener generally depends on the application rate of herbicide and the efficacy of the safener in question; it can vary within wide limits, for example in the range of from 200:1 to 1:200, preferably from 100:1 to 1:100, in particular 20:1 to 1:20. The safeners can be formulated with further herbicides/pesticides, analogously to the compounds (I) or their mixtures, and provided and used as readymix or tank mix together with the herbicides.

For use, the herbicide or herbicide safener formulations, which are present in a customary commercial form, are, if appropriate, diluted in the customary fashion, for example using water in the case of wettable powders, emulsifiable concentrates, dispersions and water-dispersible granules. Preparations in the form of dusts, soil granules, granules for spreading, and sprayable solutions, are usually not diluted further with other inert materials prior to use.

The application rate required of the compounds of the formula (I) varies with, inter alia, the external conditions such as temperature, humidity and the type of the herbicide used. It can vary within wide limits, for example between 0.001 and 10.0 kg/ha or more of active substance, but it is preferably between 0.002 and 3 kg/ha, in particular 0.005 and 1 kg/ha.

B. FORMULATION EXAMPLES a) A dust is obtained by mixing 10 parts by weight of a compound of formula (I) and 90 parts by weight of talc as inert material and grinding the mixture in a hammer mill.

b) A wettable powder which is readily dispersible in water is obtained by mixing 25 parts by weight of a compound of formula (I), 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of formula (I), 75 parts by weight of cyclohexanone as solvent and 10 parts by weight of oxethylated nonylphenol as emulsifier.

e) Water-dispersible granules are obtained by mixing
75 parts by weight of a compound of formula (I),
10 parts by weight of calcium ligno-sulfonate,
5 parts by weight of sodium laurylsulfate,
3 parts by weight of polyvinyl alcohol and
7 parts by weight of kaolin, grinding the mixture in a pinned disk mill and granulating the powder in a fluidized bed by spraying on water as granulation liquid.

f) Alternatively, water-dispersible granules are obtained by homogenizing and precomminuting, on a colloid mill, 25 parts by weight of a compound of formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture on a bead mill and atomizing and drying the resulting suspension in a spray tower by means of a single-substance nozzle.

C. BIOLOGICAL EXAMPLES

Biological Example 1

Pre-emergence Effect on Weeds

Seeds of monocotyledonous and dicotyledonous weeds and/or crops were placed in sandy loam in wood-fibre-pots and covered with soil.

The compounds formulated as wettable powders or emulsifiable concentrates were dissolved and diluted with water containing adjuvant and then applied to the surface of the covering soil at different dose rates at an application volume of 600 or 800 litres water per ha.

After the treatment, the pots were placed in the greenhouse and kept under good growth conditions for the plants.

The herbicidal effect was assessed visually as a percentage figure in comparison with the untreated control three to four weeks after application. 100% Efficacy refers to the complete damage of the assessed plants, 0% efficacy refers to the appearance of the untreated control.

Compound numbers 3, 5, 6, 18, 21, 30, 31, 32, 148 and 487 according to the invention show a very good pre-emergence control of harmful weed species such as *Galium aparine, Abutilon theophrasti, Alopecurus myosuroides, Avena fatua, Ipomoea purpurea, Echinchloa crus-galli, Solanum nigrum* and *Cyperus iria*, when applied at an application rate of 3 kg or less of active ingredient per hectare.

Biological Example 2

Post-emergence Effect on Weeds

Seeds of monocotyledonous and dicotyledonous weeds and/or crops were placed in sandy loam in wood-fibre-pots covered with soil and grown under good greenhouse conditions.

The plants were treated at the one-leaf-stage two to three weeks after sowing.

The compounds, formulated as wettable powders or emulsifiable concentrates were dissolved and diluted with water containing adjuvant and then applied over the top of the plants at different dose rates at an application volume of 600 or 800 litres water per ha.

After the treatment, the pots were placed in the greenhouse and kept under good growth conditions for the plants.

The herbicidal effect was assessed visually as a percentage figure in comparison with the untreated control three to four weeks after application Compound numbers 3, 5, 6, 12, 14, 16, 17, 18, 21, 23, 28, 30, 31, 32, 148 and 487 according to the invention show a very good post-emergence control of the tested weed species such as *Galium aparine, Abutilon theophrasti, Alopecurus myosuroides, Avena fatua, Ipomoea purpurea, Echinchloa crus-*

The invention claimed is:

1. A method of controlling harmful plants or regulating the growth of plants which comprises applying to the plants, to plant seeds or to the area under cultivation an effective amount of one or more compounds of the formula (I) or salts thereof

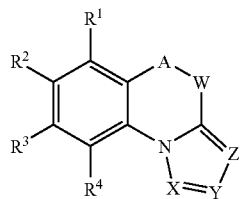

(I)

wherein:
A-W is N=N, N$^+$(O$^-$)=N or NR$^5$—NR$^6$, wherein A represents the atom or substituted atom shown on the left side of the groups representing A-W;
X is N or CR$^7$;
Y is N or CR$^8$;
Z is N or CR$^9$;
R$^1$, R$^2$, R$^3$ and R$^4$ are each independently H, OH, halogen, nitro, cyano, formyl, amino, carbamoyl, CO$_2$H or sulfamoyl, or benzyl or phenoxy,
where each of the latter two radicals is unsubstituted or substituted by one or more radicals selected from the group consisting of (C$_1$-C$_6$)alkyl, (C$_1$-C$_6$)haloalkyl, halogen, OH, (C$_1$-C$_6$)alkoxy, (C$_1$-C$_6$)haloalkoxy, (C$_1$-C$_6$)alkyl-S(O)$_n$—, nitro, cyano, amino, (C$_1$-C$_6$)alkylamino, (C$_1$-C$_6$)dialkylamino, (C$_1$-C$_6$)alkoxycarbonyl and CO$_2$H,
or are (C$_1$-C$_6$)alkyl, (C$_2$-C$_6$)alkenyl, (C$_2$-C$_6$)alkynyl, (C$_3$-C$_6$)cycloalkyl, (C$_3$-C$_6$)cycloalkyl-(C$_1$-C$_6$)alkyl-, (C$_1$-C$_6$)alkoxy, (C$_2$-C$_6$)alkenyloxy, (C$_2$-C$_6$)alkynyloxy, (C$_1$-C$_6$)alkyl-C(=O)O—, (C$_1$-C$_6$)alkyl-S(O)$_n$—, (C$_1$-C$_6$)alkylamino, (C$_1$-C$_6$)dialkylamino, (C$_1$-C$_6$)alkoxycarbonyl, (C$_1$-C$_6$)alkylcarbonyl, (C$_1$-C$_6$)alkylcarbamoyl, (C$_1$-C$_6$)dialkylcarbamoyl, (C$_1$-C$_6$)alkylsulfamoyl or (C$_1$-C$_6$)dialkylsulfamoyl,
where each of the 18 last-mentioned radicals is unsubstituted or substituted by one or more radicals selected from the group consisting of halogen, OH, (C$_1$-C$_6$)alkoxy, (C$_1$-C$_6$)alkyl-S(O)$_n$—and in the case of cyclic radicals also (C$_1$-C$_6$)alkyl and (C$_1$-C$_6$)haloalkyl;
R$^5$ and R$^6$ are each independently H, (C$_1$-C$_6$)alkyl, (C$_1$-C$_6$)haloalkyl, (C$_2$-C$_6$)alkenyl, (C$_2$-C$_6$)alkynyl, formyl, (C$_1$-C$_6$)alkylcarbonyl, (C$_2$-C$_6$)alkenylcarbonyl, COR$^{10}$, (C$_1$-C$_6$)alkoxycarbonyl, (C$_1$-C$_6$)alkyl-SO$_2$—, (C$_1$-C$_6$)alkoxy-(C$_1$-C$_6$)alkyl- or R$^{10}$;
R$^7$, R$^8$ and R$^9$ are each independently H, halogen, nitro, cyano, S(O)$_n$R$^{10}$, S(O)$_n$CH$_2$CO$_2$R$^{11}$, S(O)$_n$CH$_2$CO$_2$N[(C$_1$-C$_6$)alkyl]$_2$, S(O)$_n$CH$_2$CONR$^{12}$NR$^{13}$, S(O)$_n$CH$_2$CONR$^{14}$NR$^{15}$, formyl, carbamoyl, OH, SH, R$^{10}$, NR$^{16}$R$^{17}$, 1,3-dioxolan-2-yl, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkyl-S(O)$_n$—, (C$_1$-C$_6$)alkoxycarbonyl, (C$_1$-C$_6$)alkylcarbonyl, (C$_1$-C$_6$)alkylcarbamoyl or (C$_1$-C$_6$)dialkylcarbamoyl, where each of the 10 last-mentioned radicals is unsubstituted or substituted by one or more radicals selected from the group consisting of halogen, OH, (C$_1$-C$_6$)alkoxy, (C$_1$-C$_6$)alkyl-S(O)$_n$—and in the case of cyclic radicals also (C$_1$-C$_6$)alkyl and (C$_1$-C$_6$)haloalkyl;
R$^{10}$ is (CH$_2$)$_m$phenyl unsubstituted or substituted by one or more radicals selected from the group consisting of halogen, (C$_1$-C$_6$)alkyl, (C$_1$-C$_6$)haloalkyl, (C$_1$-C$_6$)alkoxy, (C$_1$-C$_6$)haloalkoxy, nitro, cyano, (C$_1$-C$_6$)alkyl-S(O)$_n$—, (C$_1$-C$_6$)haloalkyl-S(O)$_n$—, amino, (C$_1$-C$_6$)alkylamino, (C$_1$-C$_6$)dialkylamino, (C$_1$-C$_6$)alkylcarbonyl, carbamoyl, (C$_1$-C$_6$)alkylcarbamoyl, (C$_1$-C$_6$)dialkylcarbamoyl, sulfamoyl, (C$_1$-C$_6$)alkylsulfamoyl and (C$_1$-C$_6$)dialkylsulfamoyl;
R$^{11}$ is H or (C$_1$-C$_6$)alkyl;
R$^{12}$ and R$^{13}$, or R$^{16}$ and R$^{17}$ are each independently H, (C$_1$-C$_6$)alkyl or R$^{10}$; or R$^{12}$ and R$^{13}$, or R$^{16}$ and R$^{17}$ together with the respective attached N atom form a five- or six-membered saturated ring which optionally contains an additional hetero atom in the ring which is selected from 0, S and N, the ring being unsubstituted or substituted by one or more radicals selected from halogen, (C$_1$-C$_6$)alkyl and (C$_1$-C$_6$)haloalkyl;
R$^{14}$ and R$^{15}$ are each independently H or (C$_1$-C$_6$)alkyl;
n is 0, 1 or 2 in each of the occurrences; and
m is 0 or 1;
as a herbicide or plant growth regulator.

2. The method as claimed in claim 1 wherein A-W is A-W is N=N, N$^+$(O$^-$)=N or NH—NH.

3. The method as claimed in claim 1 wherein R$^1$, R$^2$, R$^3$ and R$^4$ are each independently H, OH, halogen, nitro, cyano, formyl, amino, carbamoyl, CO$_2$H or sulfamoyl, or benzyl or phenoxy, where each of the latter two radicals is unsubstituted or substituted by one or more radicals selected from the group consisting of (C$_1$-C$_4$)alkyl, (C$_1$-C$_4$)haloalkyl, halogen, OH, (C$_1$-C$_4$)alkoxy, (C$_1$-C$_4$)haloalkoxy, (C$_1$-C$_4$)alkyl-S(O)—, nitro, cyano, amino, (C$_1$-C$_4$)alkylamino, (C$_1$-C$_4$)dialkylamino, (C$_1$-C$_4$)alkoxycarbonyl and CO$_2$H,
or are (C$_1$-C$_4$)alkyl, (C$_2$-C$_4$)alkenyl, (C$_2$-C$_4$)alkynyl, (C$_3$-C$_6$)cycloalkyl, (C$_3$-C$_6$)cycloalkyl-(C$_1$-C$_4$)alkyl-, (C$_1$-C$_4$)alkoxy, (C$_2$-C$_4$)alkenyloxy, (C$_2$-C$_4$)alkynyloxy, (C$_1$-C$_4$)alkyl-C(=O)O—, (C$_1$-C$_4$)alkyl-S(O)$_n$—, (C$_1$-C$_4$)alkylamino, (C$_1$-C$_4$)dialkylamino, (C$_1$-C$_4$)alkoxycarbonyl, (C$_1$-C$_4$)alkylcarbonyl, (C$_1$-C$_4$)alkylcarbamoyl, (C$_1$-C$_4$)dialkylcarbamoyl, (C$_1$-C$_4$)alkylsulfamoyl or (C$_1$-C$_4$)dialkylsulfamoyl, where each of the 18 last-mentioned radicals is unsubstituted or substituted by one or more radicals selected from the group consisting of halogen, OH, (C$_1$-C$_4$)alkoxy, (C$_1$-C$_4$)alkyl-S(O)$_n$— and in the case of cyclic radicals also (C$_1$-C$_6$)alkyl and (C$_1$-C$_6$)haloalkyl.

4. The method as claimed in claim 1, wherein X is N or CR$^7$ wherein R$^7$ is H, halogen, nitro, cyano, S(O)$_n$R$^{10}$, S(O)$_n$CH$_2$CO$_2$R$^{11}$, S(O)$_n$CH$_2$CONR$^{12}$R$^{13}$, S(O)$_n$CH$_2$CONR$^{14}$NR$^{15}$, formyl, carbamoyl, OH, SH, R$^{10}$, NR$^{16}$R$^{17}$, 1,3-dioxolan-2-yl, (C$_1$-C$_4$)alkyl, (C$_3$-C$_6$)cycloalkyl, (C$_2$-C$_4$)alkenyl, (C$_2$-C$_4$)alkynyl, (C$_1$-C$_4$)alkoxy, (C$_1$-C$_4$)alkyl-S(O)$_n$—, (C$_1$-C$_4$)alkoxycarbonyl, (C$_1$-C$_4$)alkylcarbonyl, (C$_1$-C$_4$)alkylcarbamoyl, (C$_1$-C$_4$)dialkylcarbamoyl, where each of the 10 last-mentioned radicals is unsubstituted or substituted by one or more radicals selected from the group consisting of halogen, OH, (C$_1$-C$_4$)alkoxy and (C$_1$-C$_4$)alkyl-S(O)$_n$—; in which
R$^{10}$ is (CH$_2$)$_m$phenyl unsubstituted or substituted by one or more radicals selected from the group consisting of halogen, (C$_1$-C$_4$)alkyl, (C$_1$-C$_4$)haloalkyl, (C$_1$-C$_4$)alkoxy, (C$_1$-C$_4$)haloalkoxy, nitro, cyano, (C$_1$-C$_4$)alkyl-S(O)$_n$—, (C$_1$-C$_4$)haloalkyl-S(O)$_n$—, amino, (C$_1$-C$_4$)alkylamino, (C$_1$-C$_4$)dialkylamino, (C$_1$-C$_4$)

alkylcarbonyl, carbamoyl, (C$_1$-C$_4$)alkylcarbamoyl, (C$_1$-C$_4$)dialkylcarbamoyl, sulfamoyl, (C$_1$-C$_4$)alkylsulfamoyl and (C$_1$-C$_4$)dialkylsulfamoyl;

R$^{11}$ is H or (C$_1$-C$_4$)alkyl;

R$^{12}$ and R$^{13}$, or R$^{16}$ and R$^{17}$ are each independently H, (C$_1$-C$_4$)alkyl or R$^{10}$; or R$^{12}$ and R$^{13}$, or R$^{16}$ and R$^{17}$ together with the respective attached N atom form a five- or six-membered saturated ring which optionally contains an additional hetero atom in the ring which is selected from O,S and N, the ring being unsubstituted or substituted by one or more radicals selected from halogen, (C$_1$-C$_4$)alkyl and (C$_1$-C$_4$)haloalkyl; and R$^{14}$ and R$^{15}$ are each independently H or (C$_1$-C$_4$)alkyl.

5. The method as claimed in claim 1 wherein Y and Z are each N.

6. The method as claimed in claim 1 wherein:

A-W is N=N, N$^+$(O$^-$)=N or NH—NH;

R$^1$, R$^2$, R$^3$ and R$^4$ are each independently H, OH, halogen, nitro, cyano, formyl, amino, carbamoyl, CO$_2$H or sulfamoyl, or benzyl or phenoxy, where each of the latter two radicals is unsubstituted or substituted by one or more radicals selected from the group consisting of (C$_1$-C$_4$)alkyl, (C$_1$-C$_4$)haloalkyl, halogen, OH, (C$_1$-C$_4$)alkoxy, (C$_1$-C$_4$)haloalkoxy, (C$_1$-C$_4$)alkyl-S(O)$_n$—, nitro, cyano, amino, (C$_1$-C$_4$)alkylamino, (C$_1$-C$_4$)dialkylamino, (C$_1$-C$_4$)alkoxycarbonyl and CO$_2$H, or are (C$_1$-C$_4$)alkyl, (C$_2$-C$_4$)alkenyl, (C$_2$-C$_4$)alkynyl, (C$_3$-C$_6$)cycloalkyl, (C$_3$-C$_6$)cycloalkyl-(C$_1$-C$_4$)alkyl-, (C$_1$-C$_4$)alkoxy, (C$_2$-C$_4$)alkenyloxy, (C$_2$-C$_4$)alkynyloxy, (C$_1$-C$_4$)alkyl-C(=O)O—, (C$_1$-C$_4$)alkyl-S(O)$_n$—, (C$_1$-C$_4$)alkylamino, (C$_1$-C$_4$)dialkylamino, (C$_1$-C$_4$)alkoxycarbonyl, (C$_1$-C$_4$)alkylcarbonyl, (C$_1$-C$_4$)alkylcarbamoyl, (C$_1$-C$_4$)dialkylcarbamoyl, (C$_1$-C$_4$)alkylsulfamoyl or (C$_1$-C$_4$)dialkylsulfamoyl, where each of the 18 last-mentioned radicals is unsubstituted or substituted by one or more radicals selected from the group consisting of halogen, OH, (C$_1$-C$_4$)alkoxy, (C$_1$-C$_4$)alkyl-S(O)$_n$— and in the case of cyclic radicals also (C$_1$-C$_6$)alkyl and (C$_1$-C$_6$)haloalkyl;

X is N or CR$^7$;

R$^7$ is H, (C$_1$-C$_4$)alkyl, (C$_1$-C$_4$)haloalkyl, (C$_2$-C$_4$)alkenyl, (C$_2$-C$_4$)alkynyl, (C$_1$-C$_4$)alkoxy, (C$_1$-C$_4$)haloalkoxy, halogen, nitro, cyano, (C$_1$-C$_4$)alkyl-S(O)$_n$—, (C$_1$-C$_4$)haloalkyl-S(O)$_n$—, S(O)$_n$R$^{10}$, S(O)$_n$CH$_2$CO$_2$R$^{11}$, S(O)$_n$CH$_2$CO$_2$N[(C$_1$-C$_4$)alkyl]$_2$, S(O)$_n$CH$_2$CONR$^{12}$R$^{13}$, S(O)$_n$CH$_2$CONR$^{14}$NR$^{15}$, (C$_1$-C$_4$)alkoxycarbonyl, formyl, (C$_1$-C$_4$)alkylcarbonyl, (C$_1$-C$_4$)haloalkylcarbonyl, carbamoyl, (C$_1$-C$_4$)alkylcarbamoyl, (C$_1$-C$_4$)dialkylcarbamoyl, OH, SH, R$^{10}$, NR$^{16}$R$^{17}$ or 1,3-dioxolan-2-yl; in which R$^{10}$ is (CH$_2$)$_m$phenyl unsubstituted or substituted by one or more radicals selected from the group consisting of halogen, (C$_1$-C$_4$)alkyl, (C$_1$-C$_4$)haloalkyl, (C$_1$-C$_4$)alkoxy, (C$_1$-C$_4$)haloalkoxy, nitro, cyano, (C$_1$-C$_4$)alkyl-S(O)$_n$—, (C$_1$-C$_4$)haloalkyl-S(O)$_n$—, amino, (C$_1$-C$_4$)alkylamino, (C$_1$-C$_4$)dialkylamino, (C$_1$-C$_4$)alkylcarbonyl, carbamoyl, (C$_1$-C$_4$)alkylcarbamoyl, (C$_1$-C$_4$)dialkylcarbamoyl, sulfamoyl, (C$_1$-C$_4$)alkylsulfamoyl and (C$_1$-C$_4$)dialkylsulfamoyl;

R$^{11}$ is H or (C$_1$-C$_4$)alkyl;

R$^{12}$ and R$^{13}$, or R$^{16}$ and R$^{17}$ are each independently H, (C$_1$-C$_4$)alkyl or R$^{10}$; or R$^{12}$ and R$^{13}$, or R$^{16}$ and R$^{17}$ together with the respective attached N atom form a five- or six-membered saturated ring which optionally contains an additional hetero atom in the ring which is selected from O,S and N, the ring being unsubstituted or substituted by one or more radicals selected from halogen, (C$_1$-C$_4$)alkyl and (C$_1$-C$_4$)haloalkyl; and R$^{14}$ and R$^{15}$ are each independently H or (C$_1$-C$_4$)alkyl; and Y and Z are each N.

7. A compound of formula (Ii):

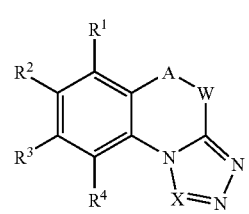

(Ii)

wherein:

A-W is N=N, N$^+$(O$^-$)=N or NH—NH, in which A represents the atom or substituted atom shown on the left side of the groups representing A-W;

X is N or CR$^7$;

R$^1$, R$^2$, R$^3$ and R$^4$ are each independently H, OH, halogen, nitro, cyano, formyl, amino, carbamoyl, CO$_2$H or sulfamoyl, or benzyl or phenoxy, where each of the latter two radicals is unsubstituted or substituted by one or more radicals selected from the group consisting of (C$_1$-C$_6$)alkyl, (C$_1$-C$_6$)haloalkyl, halogen, OH, (C$_1$-C$_6$)alkoxy, (C$_1$-C$_6$)haloalkoxy, (C$_1$-C$_6$)alkyl-S(O)$_n$—, nitro, cyano, amino, (C$_1$-C$_6$)alkylamino, (C$_1$-C$_6$)dialkylamino, (C$_1$-C$_6$)alkoxycarbonyl and CO$_2$H, or are (C$_1$-C$_6$)alkyl, (C$_2$-C$_6$)alkenyl, (C$_2$-C$_6$)alkynyl, (C$_3$-C$_6$)cycloalkyl, (C$_3$-C$_6$)cycloalkyl-(C$_1$-C$_6$)alkyl-, (C$_1$-C$_6$)alkoxy, (C$_2$-C$_6$)alkenyloxy, (C$_2$-C$_6$)alkynyloxy, (C$_1$-C$_6$)alkyl-C(=O)O—, (C$_1$-C$_6$)alkyl-S(O)$_n$—, (C$_1$-C$_6$)alkylamino, (C$_1$-C$_6$)dialkylamino, (C$_1$-C$_6$)alkoxycarbonyl, (C$_1$-C$_6$)alkylcarbonyl, (C$_1$-C$_6$)alkylcarbamoyl, (C$_1$-C$_6$)dialkylcarbamoyl, (C$_1$-C$_6$)alkylsulfamoyl or (C$_1$-C$_6$)dialkylsulfamoyl, where each of the 18 last-mentioned radicals is unsubstituted or substituted by one or more radicals selected from the group consisting of halogen, OH, (C$_1$-C$_6$)alkoxy, (C$_1$-C$_6$)alkyl-S(O)$_n$— and in the case of cyclic radicals also (C$_1$-C$_6$)alkyl and (C$_1$-C$_6$)haloalkyl;

R$^7$ is H, (C$_1$-C$_6$)alkyl, (C$_1$-C$_6$)haloalkyl, (C$_2$-C$_6$)alkenyl, (C$_2$-C$_6$)alkynyl, (C$_1$-C$_6$)alkoxy, (C$_1$-C$_6$)haloalkoxy, halogen, nitro, cyano, (C$_1$-C$_6$)alkyl-S(O)$_n$—, (C$_1$-C$_6$)haloalkyl-S(O)$_n$—, (C$_1$-C$_6$)alkoxycarbonyl, formyl, (C$_1$-C$_6$)alkylcarbonyl, (C$_1$-C$_6$)haloalkylcarbonyl, carbamoyl, (C$_1$-C$_6$)alkylcarbamoyl, (C$_1$-C$_6$)dialkylcarbamoyl, NR$^{16}$R$^{17}$ or 1,3-dioxolan-2-yl; and R$^{16}$ and R$^{17}$ are each independently H, (C$_1$-C$_6$)alkyl or R$^{10}$, wherein R$^{10}$ is (CH$_2$)$_m$phenyl unsubstituted or substituted by one or more radicals selected from the group consisting of halogen, (C$_1$-C$_6$)alkyl, (C$_1$-C$_6$)haloalkyl, (C$_1$-C$_6$)alkoxy, (C$_1$-C$_6$)haloalkoxy, nitro, cyano, (C$_1$-C$_6$)alkyl-S(O)$_n$—, (C$_1$-C$_6$)haloalkyl-S(O)$_n$—, amino, (C$_1$-C$_6$)alkylamino, (C$_1$-C$_6$)dialkylamino, (C$_1$-C$_6$)alkylcarbonyl, carbamoyl, (C$_1$-C$_6$)alkylcarbamoyl, (C$_1$-C$_6$)dialkylcarbamoyl, sulfamoyl, (C$_1$-C$_6$)alkylsulfamoyl and (C$_1$-C$_6$)dialkylsulfamoyl;

with the exclusion of compounds wherein:

i) A-W is N=N; R$^1$, R$^2$, R$^3$ and R$^4$ are each H; and X is C—Br, CSO$_2$Me, CSMe, CMe, CH, C-phenyl, C—SH, C—S—CH$_2$C$_6$H$_5$, C—S—CH$_2$COOH, C—S—

CH$_2$CO-morpholino, C—S—CH$_2$CO-piperidyl, C—(N-methyl-piperazino), C—S—CH$_2$CON(i-propyl)$_2$ or C—OH;

ii) A-W is N=N; R$^1$, R$^3$ and R$^4$ are each H; R$^2$ is Cl; and X is CH, C—SH, C—S—CH$_2$C$_6$H$_5$, C—S—CH$_2$COOC$_2$H$_5$, C—S—CH$_2$CO—NHNH$_2$ or C—OH;

iii) A-W is N=N; R$^2$, R$^3$ and R$^4$ are each H; R$^1$ is OH or OCH$_3$; and X is CH;

iv) A-W is N$^+$(O$^-$)=N; R$^1$, R$^2$, R$^3$ and R$^4$ are each H; and X is CH or C—SH;

v) A-W is NH—NH; R$^1$, R$^2$, R$^3$ and R$^4$ are each H; and X is C—OH, C—(morpholino), C—(N-methyl-piperazino), CSMe or CH;

vi) A-W is NH—NH; R$^1$, R$^3$ and R$^4$ are each H; R$^2$ is Me; and X is CH;

vii) A-W is N=N; R$^1$, R$^2$ and R$^4$ are each H; R$^3$ is OMe; and X is N;

viii) A-W is N=N; R$^1$, R$^3$ and R$^4$ are each H; R$^2$ is OMe, Me or H; and X is N;

ix) A-W is N=N; R$^1$ and R$^3$ are each H; R$^2$ and R$^4$ are each Me; and X is N;

x) A-W is N$^+$(O$^-$)=N; R$^1$, R$^3$ and R$^4$ are each H; R$^2$ is Me or OMe; and X is N;

xi) A-W is N$^+$(O$^-$)=N; R$^1$ and R$^3$ are each H; R$^2$ and R$^4$ are each Me; and X is N; and xii) A-W is NH—NH; R$^1$, R$^2$, R$^3$ and R$^4$ are each H; and X is N and xiii) A-W is —NH—NH—; R$^1$, R$^3$ and R$^4$ are each H; R$^2$ is Cl; and X is C—OH.

8. A process for the preparation of a compound of formula (Ii), or a salt thereof, as defined in claim 7 which comprises:

a) where A-W is N=N or N$^+$(O$^-$)=N, cyclodehydrating a compound of formula (II):

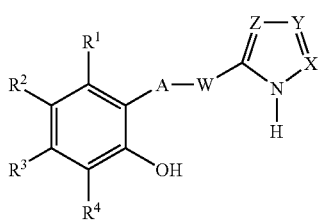

(II)

wherein A-W is N=N or N$^+$(O$^-$)=N, Y is N, Z is N and R$^1$, R$^2$, R$^3$, R$^4$, and are as defined in formula (Ii); or b) where A-W is N=N, and the other values are as defined above, coupling a diazonium salt of formula (III):

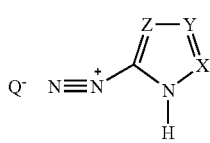

(III)

wherein Y is N, Z is N and X is as defined in formula (Ii) and Q is a chloride, sulfate or fluoroborate, with a compound of formula (IV):

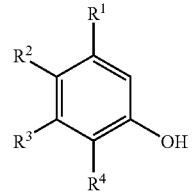

(IV)

wherein R$^1$, R$^2$, R$^3$ and R$^4$ are as defined in claim 1, to give an azo intermediate of formula (II) wherein A-W is N=N, and the other values are as defined in formula (Ii), followed by the above described cyclodehydration; or c) where A-W is NR$^5$-NR$^6$, R$^5$ and R$^6$ are each H, and the other values are as defined in formula (Ii), reducing the corresponding compound of formula (Ii) wherein A-W is N=N or N$^+$(O$^-$)=N; or d) where A-W is N=N, and the other values are as defined in formula (Ii), reducing the corresponding compound of formula (Ii) wherein A-W is N$^+$(O$^-$)=N; or e) where A-W is N=N or N$^+$(O$^-$)=N, X is CR$^7$, Y and Z are each N, and the other values are as defined in formula (Ii), reacting a compound of formula (VIII):

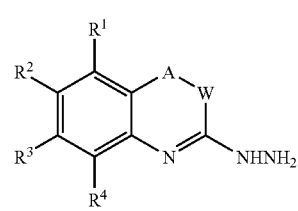

(VIII)

wherein A-W is N=N or N$^+$(O$^-$)=N, R$^7$ is H, (C$_1$-C$_6$)alkyl, (C$_1$-C$_6$)haloalkyl, (C$_2$-C$_6$)alkenyl, (C$_2$-C$_6$)alkynyl or R$^{10}$, and R$^1$, R$^2$, R$^3$ and R$^4$ are as defined in formula (Ii), with a carboxylic acid or an equivalent thereof of formula (IX) or (X):

R$^7$COL$^1$ (IX)

R$^7$C(OR)$_3$ (X)

wherein R$^7$ is H, (C$_1$-C$_6$)alkyl, (C$_1$-C$_6$)haloalkyl, (C$_2$-C$_6$)alkenyl, (C$_2$-C$_6$)alkynyl or R$^{10}$, and L$^1$ is H or a leaving group; or f) where A-W is N=N or N$^+$(O$^-$)=N, X is CR$^7$, Y and Z are each N, and the other values are as defined in formula (Ii), cyclising a compound of formula (XI):

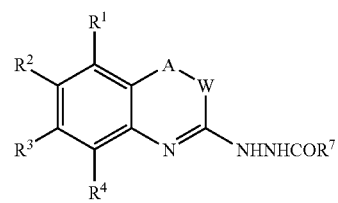

(XI)

wherein A-W is N=N or N$^+$(O$^-$)=N, R$^7$ is H, (C$_1$-C$_6$)alkyl, (C$_1$-C$_6$)haloalkyl, (C$_2$-C$_6$)alkenyl, (C$_2$-C$_6$)alkynyl or R$^{10}$, and R$^1$, R$^2$, R$^3$ and R$^4$ are as defined in formula (Ii), in the presence of a dehydrating agent or a halogenating agent; or g) where A-W is N=N or N⁺(O⁻)=N and $R^1$, $R^2$, $R^3$ and $R^4$ are as defined in formula (Ii), reacting a compound of formula (XII):

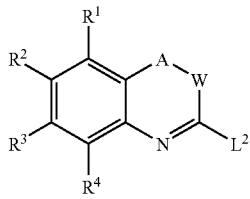

(XII)

wherein A-W is N=N or N⁺(O⁻)=N, $R^1$, $R^2$, $R^3$ and $R^4$ are as defined in formula (Ii), and $L^2$ is a leaving group, with a metal azide of formula (XIII):

 (XIII)

wherein M is an alkali metal; or h) where A-W is N⁺(O⁻)=N, and the other values are as defined in formula (Ii), oxidising the corresponding compound of formula (Ii)

wherein:

A-W is N=N.

9. A herbicidal or plant growth regulating composition characterised in that it comprises one or more compounds of the formula (Ii) or salts thereof as defined in claim 7 and formulation auxiliaries which are customary in crop protection.

10. The compound of claim 7, wherein X is N.

11. The compound of claim 7, wherein X is $CR^7$; $R^1$, $R^3$, and $R^4$ is hydrogen; and $R^2$ is hydrogen, halogen or $C_1$-$C_6$ alkyl.

12. The compound of claim 11, wherein $R^2$ is hydrogen, chloro, bromo or methyl.

13. The compound of claim 7, wherein A-W is N=N or N⁺(O⁻)=N.

14. The method of claim 5, wherein X is N.

15. The method of claim 5, wherein X is $CR^7$; $R^1$, $R^3$, and $R^4$ is hydrogen; and $R^2$ is hydrogen, halogen or $C_1$-$C_6$ alkyl.

16. The method of claim 15, wherein $R^2$ is hydrogen, chloro, bromo or methyl.

17. The method of claim 5, wherein A-W is N=N or N⁺(O⁻)=N.

* * * * *